US011478583B2

(12) United States Patent
Hooven et al.

(10) Patent No.: US 11,478,583 B2
(45) Date of Patent: Oct. 25, 2022

(54) MEDICAL FLUID TRANSFER AND INJECTION APPARATUS AND METHOD

(71) Applicant: Enable Injections, Inc., Cincinnati, OH (US)

(72) Inventors: Michael D. Hooven, Cincinnati, OH (US); Matthew J. Huddleston, Loveland, OH (US); Joetta Renee Palmer, Mason, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 779 days.

(21) Appl. No.: 15/471,631

(22) Filed: Mar. 28, 2017

(65) Prior Publication Data

US 2017/0196771 A1    Jul. 13, 2017

Related U.S. Application Data

(63) Continuation-in-part of application No. PCT/US2015/053539, filed on Oct. 1, 2015.
(Continued)

(51) Int. Cl.
*A61M 5/178* (2006.01)
*A61M 5/44* (2006.01)
(Continued)

(52) U.S. Cl.
CPC .......... *A61M 5/1782* (2013.01); *A61J 1/2075* (2015.05); *A61J 1/2096* (2013.01);
(Continued)

(58) Field of Classification Search
CPC .......... A61M 5/14224; A61M 5/14248; A61M 5/20; A61M 5/3287; A61M 5/42–425; A61M 2005/14252; A61M 2005/2033
See application file for complete search history.

(56) References Cited

U.S. PATENT DOCUMENTS 6,890,319 B1 * 5/2005 Crocker .................. A61M 5/46
                                                        604/131
10,589,076 B2 * 3/2020 Sumida .................. A61M 5/425
(Continued)

FOREIGN PATENT DOCUMENTS

EP          2535073 A1    12/2012
WO       03090509 A2    11/2003
(Continued)

OTHER PUBLICATIONS

International Search and Written Opinion from the International Search Authority for PCT Application No. PCT/US2018/034486, dated Oct. 17, 2018 (15 pages).
(Continued)

*Primary Examiner* — James D Ponton
*Assistant Examiner* — Neeraja Gollamudi
(74) *Attorney, Agent, or Firm* — Cook Alex Ltd.

(57) ABSTRACT

Drug delivery system, injection device, transfer apparatus, vial holder and method of administering and transferring are disclosed which provide for passive warming of chilled injectable transferred through the transfer apparatus and into the injection device. The injection device may include a skin-facing surface including a skin boundary displacement extension or structure around a needle injection site to create a high pressure zone in the tissue. Radio frequency tracking and monitoring features for tracking patient compliance also may be provided.

10 Claims, 58 Drawing Sheets

Related U.S. Application Data

(60) Provisional application No. 62/315,762, filed on Mar. 31, 2016, provisional application No. 62/314,729, filed on Mar. 29, 2016, provisional application No. 62/059,476, filed on Oct. 3, 2014.

(51) Int. Cl.
| | |
|---|---|
| *A61M 5/46* | (2006.01) |
| *A61J 1/20* | (2006.01) |
| *A61M 5/28* | (2006.01) |
| *A61M 5/00* | (2006.01) |
| *A61M 5/142* | (2006.01) |
| *G16H 40/67* | (2018.01) |
| *A61M 5/32* | (2006.01) |
| *G16H 20/17* | (2018.01) |

(52) U.S. Cl.
CPC ........ *A61M 5/002* (2013.01); *A61M 5/14244* (2013.01); *A61M 5/28* (2013.01); *G16H 40/67* (2018.01); *A61J 1/201* (2015.05); *A61J 1/2013* (2015.05); *A61J 2200/42* (2013.01); *A61M 5/3291* (2013.01); *A61M 5/44* (2013.01); *A61M 5/46* (2013.01); *A61M 2205/581* (2013.01); *A61M 2205/582* (2013.01); *A61M 2205/583* (2013.01); *G16H 20/17* (2018.01)

(56) References Cited

U.S. PATENT DOCUMENTS

| | | | | |
|---|---|---|---|---|
| 2003/0187423 | A1* | 10/2003 | Wilkinson | A61M 5/14248 |
| | | | | 604/506 |
| 2005/0033234 | A1* | 2/2005 | Sadowski | A61M 5/2033 |
| | | | | 604/140 |
| 2010/0160857 | A1 | 6/2010 | Pongpairchana et al. | |
| 2011/0275994 | A1* | 11/2011 | Iwase | A61M 5/425 |
| | | | | 604/117 |
| 2012/0136300 | A1* | 5/2012 | Schoonmaker | A61M 5/158 |
| | | | | 604/117 |
| 2012/0323208 | A1 | 12/2012 | Bochenko et al. | |
| 2016/0089056 | A1 | 3/2016 | Limaye et al. | |
| 2016/0296699 | A1 | 10/2016 | Cabiri | |
| 2017/0007772 | A1 | 1/2017 | Nemoto et al. | |

FOREIGN PATENT DOCUMENTS

| | | | | |
|---|---|---|---|---|
| WO | WO 2010/141632 A2 | 12/2010 | | |
| WO | WO-2011122395 A1 * | 10/2011 | ............ | A61M 5/283 |
| WO | WO 2012/019642 A1 | 2/2012 | | |
| WO | 2015187793 A1 | 12/2015 | | |
| WO | WO2016041875 A1 | 3/2016 | | |
| WO | 2016054404 A2 | 4/2016 | | |

OTHER PUBLICATIONS

Butz, Kent D., Adam J Griebel, Tyler Novak, Kevin Harris, Amy Komokovich, Michael F. Chiappetta and Corey P. Neu. "Prestress as an optimal biomechanical parameter for needle penetration." Journal of biomechanics 45 (2012): 1176-9.

International Search Report for International Application No. PCT/US2015/053539 dated Jun. 30, 2016.

International Preliminary Report on Patentability and Written Opinion of the International Search Authority for IA No. PCT/US2015/053539 dated Jun. 30, 2016.

Extended European Search Report Issued By The European Patent Office For European Application No. 18806106.3, dated Dec. 15, 2020 (4 Pages Total).

Notification of Reasons for Refusal, counterpart Japanese App. No. 2019-564830, with English translation (dated Jul. 9, 2021) (15 pages).

* cited by examiner

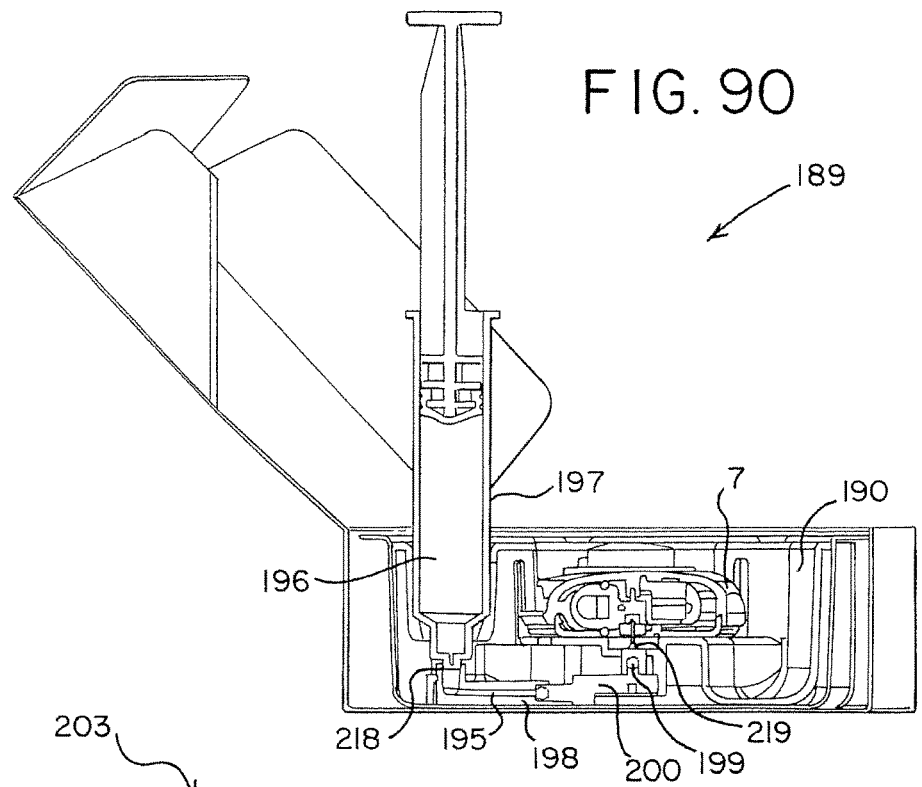
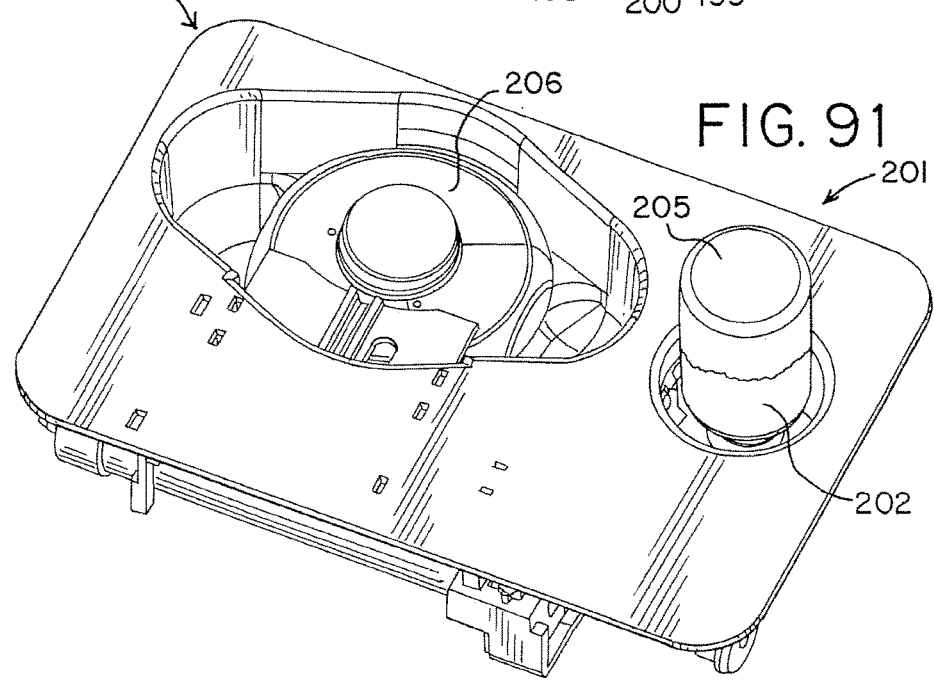

MEDICAL FLUID TRANSFER AND INJECTION APPARATUS AND METHOD

The present application is a continuation-in-part of International Application No. PCT/US15/53539, filed Oct. 1, 2015, which claims the benefit of Unites States Provisional Patent Application Ser. No. 62/059,476, filed Oct. 3, 2014. The present application also claims priority to and the benefit of U.S. Provisional Patent Application Ser. No. 62/314,729, filed Mar. 29, 2016, and U.S. Provisional Patent Application Ser. No. 62/315,762, filed Mar. 31, 2016. This application hereby incorporates by reference the entire specification, drawings and claims of each of the above applications as if they have been fully repeated herein.

The present subject matter generally relates to devices and methods for administering the contents of vials and more specifically to a disposable one-time use apparatus and method that transfers and mixes the contents of one or more vials into a disposable injection device for administration into a subject such as a human being.

BACKGROUND

Vials are one of the preferred container closure systems used by the pharmaceutical industry due to their extensive clinical history and record of long term stability with a wide variety of drugs. Pharmaceutical drugs including biologics standard containers such as vials. Additionally the industry has made a significant investment in capital equipment for aseptic vial filling. However, vials require the transfer of the contained drug from the vial to an injection device for delivery to the patient. New container closure systems such as prefilled syringes and cartridges have been introduced that allow direct transfer of the drug from the syringe or cartridge to the patient. Injection devices such as autoinjection devices and pens have been developed to utilize these newer forms of container closure. Because of uncertainty about long-term drug stability, and the extensive manufacturing resources already in place, devices that incorporate standard container closure systems such as vials, prefilled syringes or cartridges are greatly preferred by the pharmaceutical industry over devices that require a custom form of drug containment.

However, vials, prefilled syringes and cartridges are not necessarily the optimum containers for a drug delivery device. This is especially true in the case of delivery devices that deliver relatively high volumes of drugs (2-50 cc) or high viscosity (over 15 cP and up to about 100 cP). Vials, prefilled syringes and cartridges are almost exclusively cylinders made of glass, which imposes design constraints on forces and geometries. Typical syringes and autoinjection devices are limited on the viscosities of drug that can be delivered as well as by the forces that can be applied to the glass container closure systems. New injection devices have been developed including pumps for the delivery of insulin that use custom container closures, but these systems are very expensive, cannot generate high forces or pressures and typically reusable and/or refillable.

Due to factors including stability and time to market, pharmaceutical drugs including biologics are often initially marketed in a lyophilized or powder form or in concentrated liquid form. Such drugs packaged in vials in both liquid and powder formulations can require significant preparation prior to administration. To facilitate the administration of liquid formulations in vials, drugs in vials are often packaged with an empty syringe and multiple needles for aspiration out of the vials and injection into the patient. In the case of powder formulations, an additional diluent or solution vial may be provided to allow for reconstituting the powder drug into solution available for injection.

The risks associated with the preparation and administration of these drug forms are significant. They include the potential for needle stick injury during the reconstitution and administration process as well as errors with improper mixing and inaccurate dose volume or concentration delivered. This presents a real challenge for both trained caregivers and patients preparing and receiving the medication. Similar issues of risk can also apply to the transfer of ready-to-inject drug that must be transferred from a vial to an injection device.

This transfer also involves removal of the drug from the vial, measurement of the proper dose, and injection into the patient using a syringe. Incomplete transfer of the full volume of the vial necessitates overfilling of the vial by some 25-30% and the associated waste. Contamination of the drug with non-sterile ambient air that is injected into the vial, or improper sterile technique can cause contamination of the injectable drug.

On body injection devices have, in particular, been the subject of continuing development in efforts to develop injection devices and methods that offer benefits such as greater comfort and less pain while providing effective subcutaneous injection.

Accordingly, there continues to exist a need for new and/or improved apparatus and methods for transfer, mixing and injection of medicament drugs from a source vial or vials to and into a subject.

DESCRIPTION

The description below is for purposes of illustration only and not limitation. The present subject matter may be employed in a variety of apparatus, systems and methods not depicted below.

SUMMARY

The present subject matter is directed, in part, to disposable, one-time-use apparatus, preferably on-body, and methods for preferably automatically mixing and/or transferring, upon user initiation, the injectable contents of one or more standard vials or syringes into an injection device and preferably simultaneously pressurizing the injection device for subsequent automated injection into a subject and methods for injecting medicament into a subject. The contents of the vial(s) may be any suitable injectable. For purposes of this description and claims, the terms medicament, drug, injectable, fluid, medicine, medication, medical, fluid and the like are used comprehensively and include without limitation drugs of any type, therapeutic or diagnostic, antibiotics, biologics, sedatives, sterile water and other injectable materials, either alone or in combination with one or more other injectables, and whether or not requiring reconstitution or concentration adjustment or other processing before injection.

The present subject matter includes a transfer device and/or an injection device of any suitable detailed construction, but transfer and injection devices that are particularly useful in combination with the apparatus here are described in U.S. patent application Ser. No. 61/326,492 filed Apr. 21, 2010; U.S. patent application Ser. No. 13/637,756, filed Sep. 27, 2012; and U.S. patent application No. 61/704,922, filed Sep. 24, 2012, all of which are hereby incorporated by reference herein.

In one aspect, a drug delivery system for the transfer and administration of an injectable liquid drug into a subject. The system includes a transfer apparatus including an injection device docking station, an injectable inlet for receiving a chilled injectable having a temperature in range of about 2° C.-about 8° C., a fluid passageway communicating between the injectable inlet and the injection device docking station. The system also includes an injection device comprising an expandable chamber including an inlet that is configured for placement into fluid communication with the transfer apparatus fluid passageway when the injection device is received in the injection device docking station. The transfer and injection device are configured such that when at ambient temperature of about 15° C.-about 32° C., the temperature of a single dose of chilled injectable that is transferred through the transfer apparatus into the injection device is passively increased by at least about 5° C.-about 25° C.

In another aspect of the present subject matter, a drug delivery system is provided for the transfer and administration of an injectable liquid drug into a subject, comprising a transfer apparatus and an injection device. The transfer apparatus includes an injection device docking station, an injectable inlet for receiving a chilled injectable having a temperature in range of about 2° C.-about 8° C., and a fluid passageway communicating between the injectable inlet and the injection device docking station. The injection device comprises an expandable chamber including an inlet that is configured for placement into fluid communication with the transfer apparatus fluid passageway when the injection device is received in the injection device docking station. The transfer and injection device are configured such that when at ambient temperature of about 15° C.-about 32° C., the temperature of a single dose of chilled injectable that is transferred through the transfer apparatus into the injection device is passively increased by at least about 5° C.-about 25° C. No battery or other electrical heating source is needed, and this warming occurs within a relatively limited amounted of time, particularly relative to the amount of time typically required for the usual technique of unaided warming—in others words, putting the chilled drug on the counter until it warms up. Various additional features of this aspect are set forth more fully below and in the claims.

In a related aspect, a method of warming a flowable injectable suitable for injection into a living subject is also provided. The method comprises flowing an injectable dose having an initial temperature in the range of about 2° C.-about 8° C. through a passageway in a transfer apparatus and into an injection device, the transfer apparatus and injection apparatus being substantially at ambient temperature. The transfer apparatus and injection device are configured to passively raise the temperature of the injectable during flow through the transfer apparatus and into the injection apparatus by about 5° C.-about 25° C. Various additional features of this aspect are also set forth more fully below and in the claims.

In accordance with another aspect, to enhance monitoring of patient compliance, a drug injection device of the type including a housing containing an injectable reservoir and an injection needle is provided with radiofrequency tag containing data identifying such device. The tag may be an active tag or chip that signals compliance-related information such as activation of the injection device and/or completion of an injection. The following more detailed description and the claims set forth various additional features of this aspect.

In yet another aspect, a transfer apparatus for transferring an injectable from a syringe containing such injectable to an injection device, the transfer apparatus including a syringe docking station, an injection device docking station and a fluid passageway extending between a port associated with the syringe docking station and a port associated with the injection device docking station. Similarly, the following more detailed description and the claims also set forth various additional features of this aspect.

In another aspect, a medication injection device includes a housing having skin-facing surface that includes an injection needle aperture through which an injection needle may extend from the housing and a skin displacement structure extending from the skin facing surface around the needle aperture. The displacement structure serves to compress tissue around the injection aperture and thereby creates a tissue pressure zone around the injection aperture having higher pressure than in tissue outwardly of the tissue pressure zone.

In yet another aspect, the medication injection device may include an injection needle that is extendable through the aperture sufficiently to extend not more than about 5 mm into tissue when the skin-facing surface is placed in contact with tissue of a subject.

In yet another aspect, the medication injection device may include an injection needle that is extendable through the needle aperture sufficiently to extend a selected subcutaneous distance into tissue, the selected distance providing substantially similar medication bolus depth as an injection needle extending substantially twice the selected depth in the absence of a tissue displacement structure.

In yet another aspect, the medication injection device may include an injection needle extends to a subcutaneous depth of about 5 mm and generates a medication bolus depth of about 0.4 cm-about 0.45 cm.

In yet another aspect, the medication injection device may include an injection needle movable from an initial retracted position to an injection position, extending to a selected subcutaneous depth for injection, and back to a final retracted position after injection complete, the device being configured to maintain the tissue pressure zone after the needle returns to the retracted position.

In yet another aspect, the subject matter of this application may also include a method of medicament injection employing any of the injection devices set forth above.

In another aspect, a medicament delivery system for the transfer and administration of an injectable liquid drug into a subject includes a transfer apparatus and an injection device, where the transfer apparatus includes an injection device docking station. A wireless signal sending unit is carried by the transfer apparatus and/or the injection device.

In yet another aspect, the present subject matter, as explained more fully below, is directed to systems and methods for monitoring patient compliance.

In accordance with another aspect, to enhance monitoring of patient compliance, a drug injection device of the type including a housing containing an injectable reservoir and an injection needle is provided with radiofrequency tag containing data identifying such device. The tag may be an active tag or chip that signals compliance-related information such as activation of the injection device and/or completion of an injection. The following more detailed description and the claims set forth various additional features of this aspect.

In accordance with another aspect, a medicament delivery system for the transfer and administration of an injectable liquid drug into a subject may comprise a transfer apparatus and an injection device; the transfer apparatus including an injection device docking station; and a wireless signal sending unit carried by the transfer apparatus and/or the injection device.

In yet another aspect, the delivery system sending unit may comprise a radiofrequency tag containing data identifying such system. The radiofrequency tag may be an active radiofrequency tag configured to signal activation of the injection device. The active radiofrequency tag may also be configured to signal completion of injection by the injection device. Further, the active radiofrequency tag may be configured to transmit to signal activation of the injection device and to cease transmitting to signal completion of injection by the injection device.

In yet another aspect, the delivery system includes a patient module and includes an active radiofrequency tag configured to transmit a signal containing at least injection device information to a patient module remote from the injection device for receiving such signal and for storing data associated with injection device and use thereof.

In yet another aspect, the patient module may be configured to transmit to a remote computer or network, information regarding the injection device and use thereof together with unique patient information.

In yet another aspect, a medicament injection device may comprise a housing containing an injectable reservoir and an injection needle, the device further comprising a wireless signal sending unit. The sending unit may include an active radiofrequency tag configured to signal activation of the injection device. The active radiofrequency tag may be configured to signal completion of injection by the injection device. Further, the active radiofrequency tag may be configured to transmit to signal activation of the injection device and to cease transmitting to signal completion of injection by the injection device.

In yet another aspect, the above device may include a patient module that may be remotely located, and the device sending unit or active radiofrequency tag is configured to transmit a signal containing at least injection device information to the patient module, the patient module being configured to receive such signal and store data associated with injection device and use thereof. The patient module may be configured to transmit to a remote computer or network, information regarding the injection device and use thereof together with unique patient information.

In yet another aspect, the medicament delivery system or device may include a sending unit that employs Bluetooth wireless technology.

In yet another aspect, the medicament delivery system and/or device may include a sending unit configured for removal from the device for disposal.

In yet another aspect, the medicament delivery system and/or may include a sending unit configured for removal to allow most of the delivery device to be recycled. The sending unit may be configured for removal from the transfer apparatus and/or injection device, and configured for removal from the transfer apparatus and/or injection device to allow most of the apparatus and/or device to be recycled.

Turning now to a more detailed description of the subject matter of the application and its various aspects and features, reference is first made to the accompanying drawings as briefly identified below.

BRIEF DESCRIPTION OF DRAWINGS

Examples of the subject matter of this patent application are shown for purposes of illustration only, and not limitation, in the attached drawings, of which:

FIG. 90 is a vertical cross-sectional view take through the transfer and injection device with the syringe located in a docking station on the transfer device, with the plane of the cross sectional at a different position than in FIG. 89.

FIG. 91 is a perspective view of the top or exposed side of a transfer device and associated injection device for transferring the contents of a pre-filled vial, such as was shown in earlier figures.

DETAILED DESCRIPTION

Figure 1:
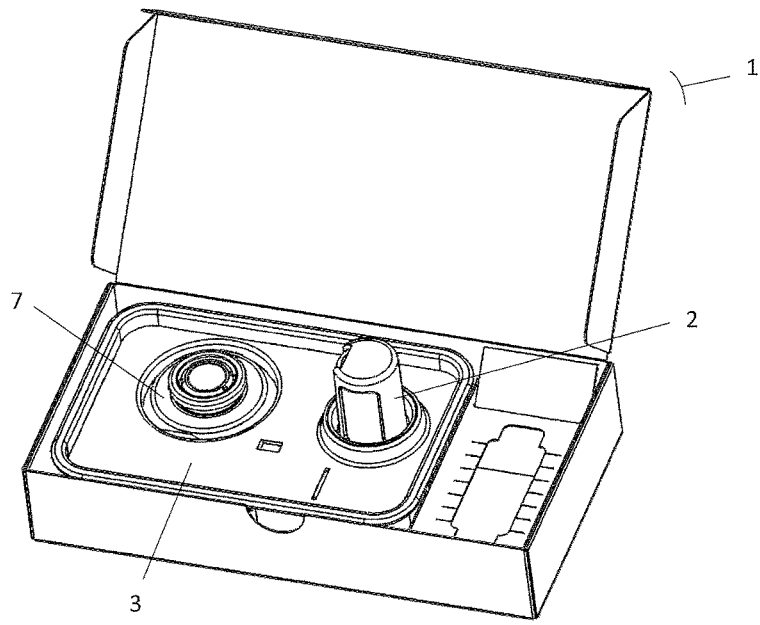
FIG. 1 is a perspective view of a single-vial system including the single vial holder, transfer apparatus and injection device system embodying the present subject matter.
Figure 2:
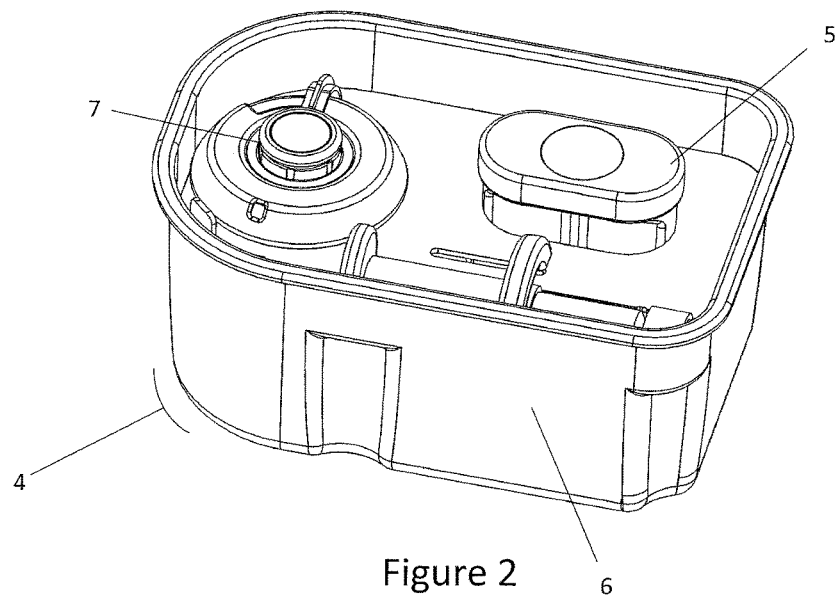
FIG. 2 is a perspective view of a dual vial system including the dual vial holder, transfer apparatus and injection device system embodying the present subject matter.

Referring to FIGS. 1 and 2, as set forth in more detail below, the disposable, one-time use, single vial transfer and injection system 1 shown in FIG. 1 may comprise a single vial holder 2, transfer apparatus 3 and injection device 7. A disposable, one-time use, dual vial mixing, transfer and injection system 4 shown in FIG. 2 may comprise a dual vial holder 5, transfer apparatus 6 and injection device 7. As mentioned earlier, each of these aspects has separate utility and may be claimed separately and/or in combination or sub-combination.

Figure 3:
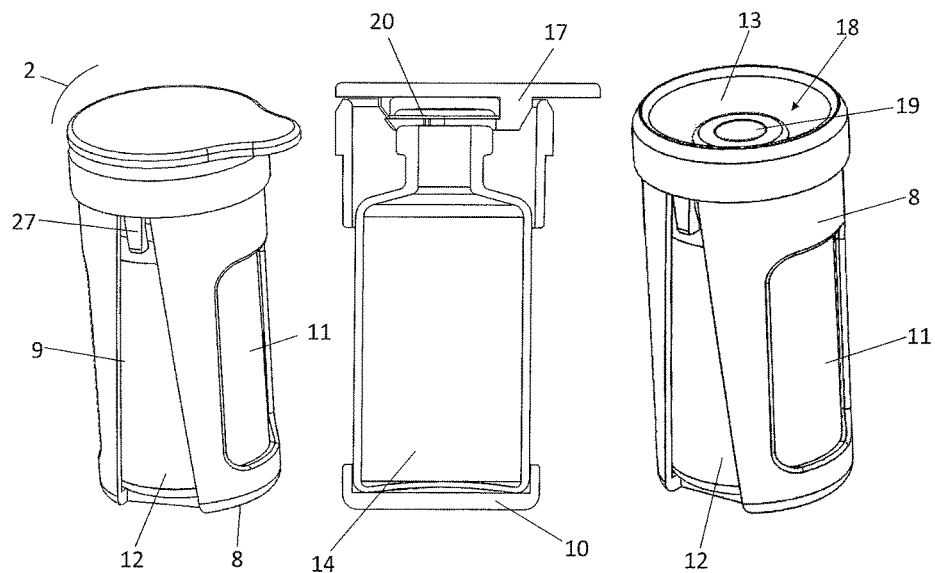
FIG. 3 includes a perspective view of a single vial holder with the removable top included, a cross-section of the single vial holder with removable top included and a perspective view of the single vial holder with the removable top and vial cap removed.
Figure 4:
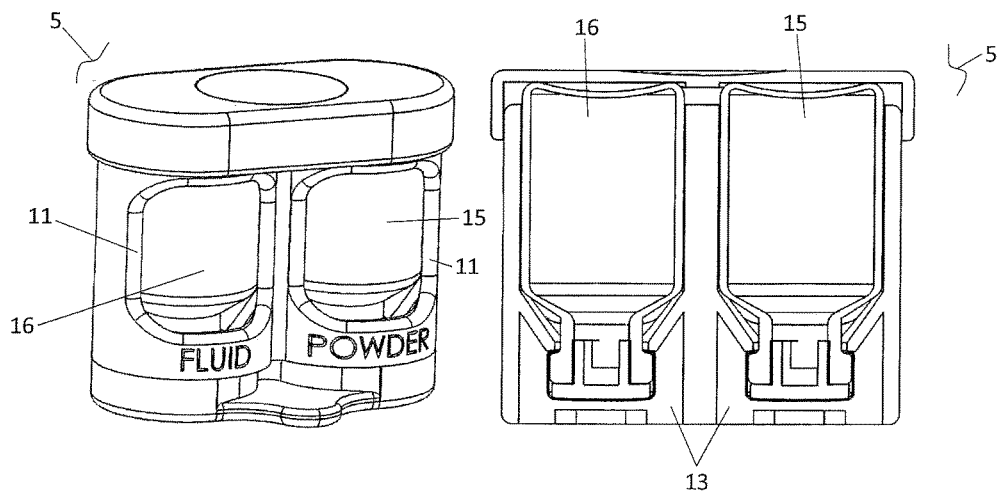
FIG. 4 includes a perspective view with removable top included and a cross-section of the dual vial holder with removable top and vial caps removed.

Referring to FIGS. 3 and 4, the single vial holder 2 shown includes a housing 8 that includes a side wall 9, end wall 10 and apertures or viewing windows 11. Alternatively the vial holder 2 material may be transparent to allow for visualization of the contents of the vial 12. The housing 8 is shaped to define at least one or two or more vial-receiving cavities 13 or zones for securely holding a vial 12 in each zone 13 as shown in FIG. 4. The cavities 13 in the vial holder 5 may be sized for receiving standard injectable vial 12 of different sizes such as from 1 to 30 ml. The vial 12 may be of the same size or different sizes and may contain any desired injectable 14. In the dual vial holder 5 illustrated in FIG. 4, the vials may include one vial of powdered, lyophilized or liquid drug 15 and one vial of liquid or diluent 16. The vial holder 5 may have the vials prepackaged and assembled therein by, for example, a drug manufacturer, or the vials may be inserted into the vial holder 5 by the end user or by a medical professional such as a pharmacist or nurse. The vial holder 5 may have appropriate markings and/or features to only allow for the assembly of certain vials in certain cavities 13. For example, the powdered drug vial 15 may be inserted into a specific cavity 13 of the vial holder 5 and diluent vial 16 in another cavity 13 of the vial holder 5. The apertures or viewing windows 11 in the vial holder 5 allow for direct visualization of the contents 14 of the vials.

Referring to FIGS. 3 and 4, as a further alternative, the vial holder 5 may be an assembly of individual vial holders 2, each of which holds a single vial 12. For example, the injectable manufacturer may preassemble a vial 12 in an individual vial holder 2 which can then be joined with the vial holder 2 of another vial 12, if needed, at the time of injection. For example, a drug manufacturer may provide a lyophilized drug 15 in its own vial holder 2 and the diluent 16, such as sterile water or saline, in a separate vial holder 2. The user or medical professional can then, as needed, join the individual vial holders 2 to form the vial holder assembly 5 for connection to the transfer apparatus 6 shown in FIG. 2.

Referring back to FIG. 3, the vial holder 2 may include a removable cover 17 that normally covers and protects the end of the vial 18 during shipping and storage. Typical standard commercial vials 12 include a pierceable septum 19 located in the vial neck for accessing the vial contents 14, which is covered by a removable vial cap or closure 20. The removable cover 17 may be configured to engage the vial cap 20 so that removal of the cover simultaneously removes vial cap 20 and exposes the vial septum 19 for accessing the contents 14 after any antiseptic swabbing of the septum 19 that may be deemed necessary by the user. The vial holder 2 may recess the vial 12 therein such that after the vial cap 20 is removed by the cover 17, the pierceable septums 19 are recessed within the vial holder 2 to reduce the chance of contamination by the user prior to insertion of the vial holder 2 into the transfer apparatus 3 as shown in FIG. 1. This system is applicable to both single vial holders 2 and dual vial holders 5.

Referring to FIG. 3, the vial holder 2 may include interlocks 27 to prevent the vial 12 from being removed once the vial 12 is inserted into the vial holder 2. This helps prevent the vial 12 from falling out or being inadvertently removed during handling.

Figure 5:
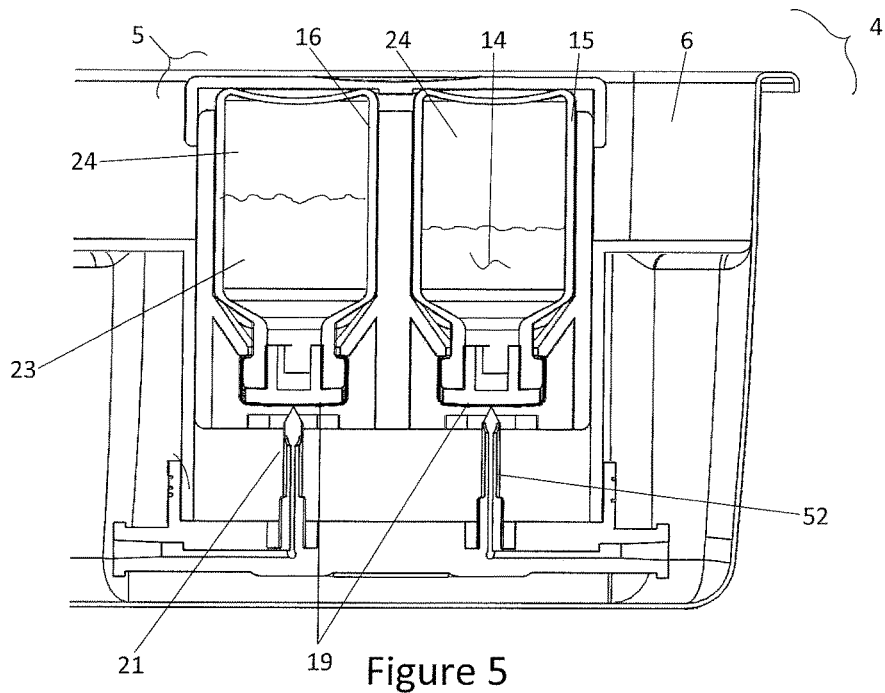
FIG. 5 is a cross-section of FIG. 2 in the area of the vial holder showing the position of the vial access members relative to the septums of the vials.

Referring to FIG. 5, the vial holder 5 may be assembled to the transfer apparatus 6 with the vial caps removed and the vials 15, 16 installed into the vial holder 5 by the device manufacturer. The exposed vial septums 19 are held in close proximity to the vial access members 21, 52 prior to activation. This configuration provides convenience by eliminating the need for the user to remove the vial caps, swab the vial tops 19 and assemble the vial holder 5 to the transfer apparatus 6 prior to use of the system 4.

Figure 6:
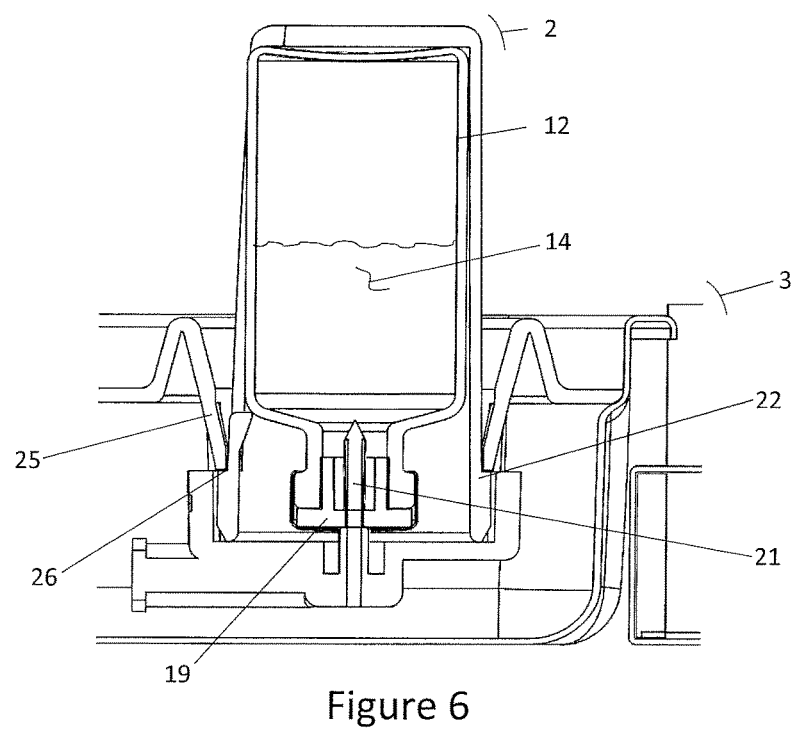
FIG. 6 is a cross-section of FIG. 1 in the area of the vial holder showing the vial access member pierced through the septum of the vial.

Referring to FIG. 6, the vial holder 2 may be packaged separately from the transfer apparatus 3. In this case, the user would remove the vial cap with the removable cover 17, swab the vial top 19 (if necessary) and assemble the vial holder 2 into the transfer apparatus 3. As shown in FIG. 6, the vial holder 2 may include lock-out features 22 that interact with the transfer apparatus 3 to prevent the vial holder 2 from being inadvertently pulled out of the transfer apparatus 3 after activation by the user.

Referring to FIG. 5, the vial holder 5 preferably is assembled to the transfer apparatus 6 to configure the vials 15, 16 upside down in a vertical position. This allows any liquid 23 in the vials to be in direct communication with the vial access members 21, 52 after insertion of the vial holder 5. This also forces the air 24 to the top of the vial in this orientation. To encourage the septums 19 to remain uncontaminated after removal of the vial caps and before insertion of the vial holder 5, the exposed vial septums 19 may be recessed into the vial holder 5 to prevent inadvertent contact as shown in FIG. 4. This configuration is applicable to single vial holder and dual vial holder configurations.

Referring to FIG. 6, the vial holder 2 preferably is mechanically configured with insertion features 25 in the transfer apparatus 3 to actuate like an on/off switch, i.e., to only have two states, open and closed such as a light switch. This may prevent the user from pushing the vial holder 2 into the transfer apparatus 3 half way and not allowing the vial access member 21 to pierce the septum 19 and allow communication between the contents 14 of the vial 12 and the transfer apparatus 3. Additionally, the vial holder 2 may interface with an interlock 26 in the transfer apparatus 3 to lock the vial holder 2 in the closed position after full insertion of the vial holder 2 to prevent the vial holder 2 from being removed from the transfer apparatus 3 after insertion.

Figure 7:
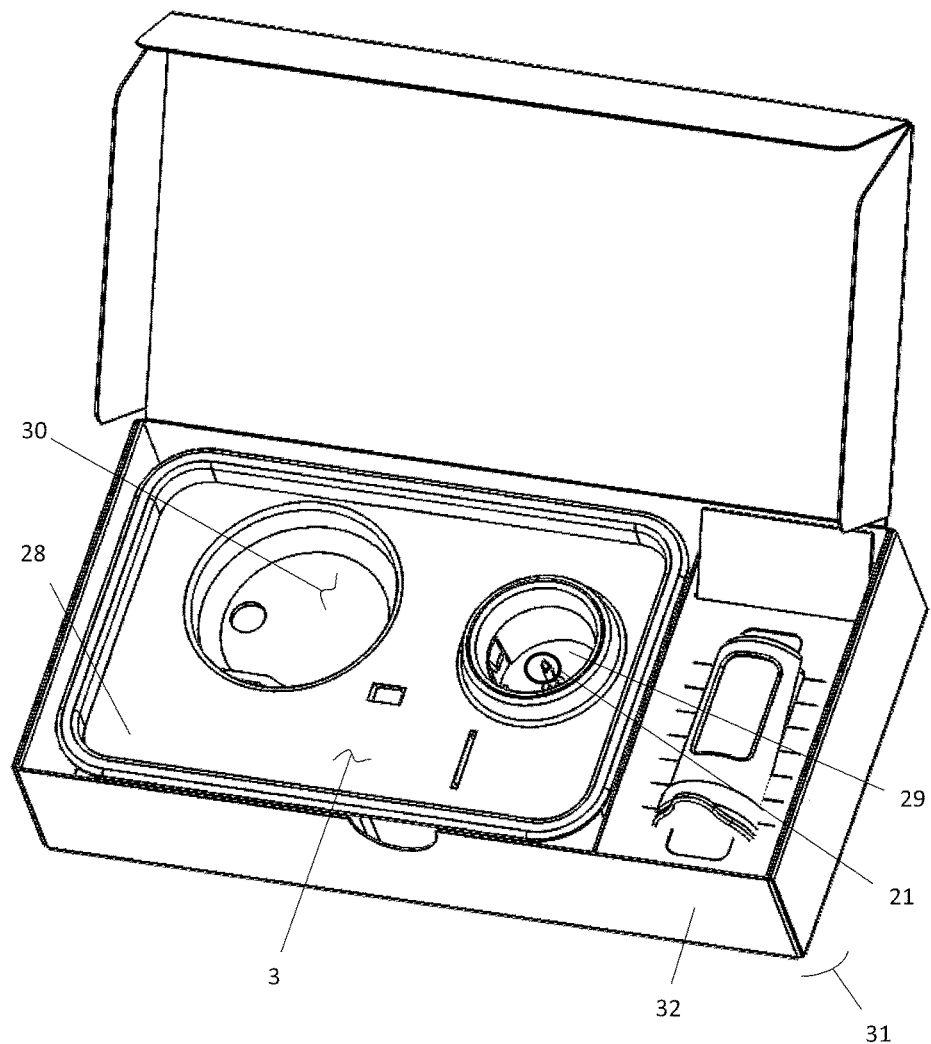
FIG. 7 is a perspective view of the transfer apparatus shown in FIG. 1 showing the vial holder and injection device receiving areas.

Referring to FIG. 7, the transfer apparatus 3 comprises an outer housing 28 and defines a vial holder docking area or first receiving station 29 and an injection device docking station or second receiving station 30 (for removable injection devices). In the illustrated structure, the vial holder docking station 29 and injection device docking station 30 are at opposite ends of the transfer apparatus housing 28.

Referring to FIG. 7, the transfer apparatus 3 may have an outer housing 28 that is integrated into the packaging 31 of the system. The outer packaging 31 may essentially form the bottom and side walls of the transfer apparatus outer housing 28. All of the operational steps in using the system up to the point of removal of the injection device may occur in this packaging 31. This may provide cost reduction and increase ease of use for the user. Additionally, incorporating the entire transfer apparatus 3 into the packaging 31 eliminates the possible user error that could occur if the user was required to remove the transfer apparatus 3 from the package 31. The packaging 31 could include a plastic tub or tray that contains the system. Furthermore, the packaging 31 could include everything within a shipping carton 32 that houses the entire system.

Figure 8:
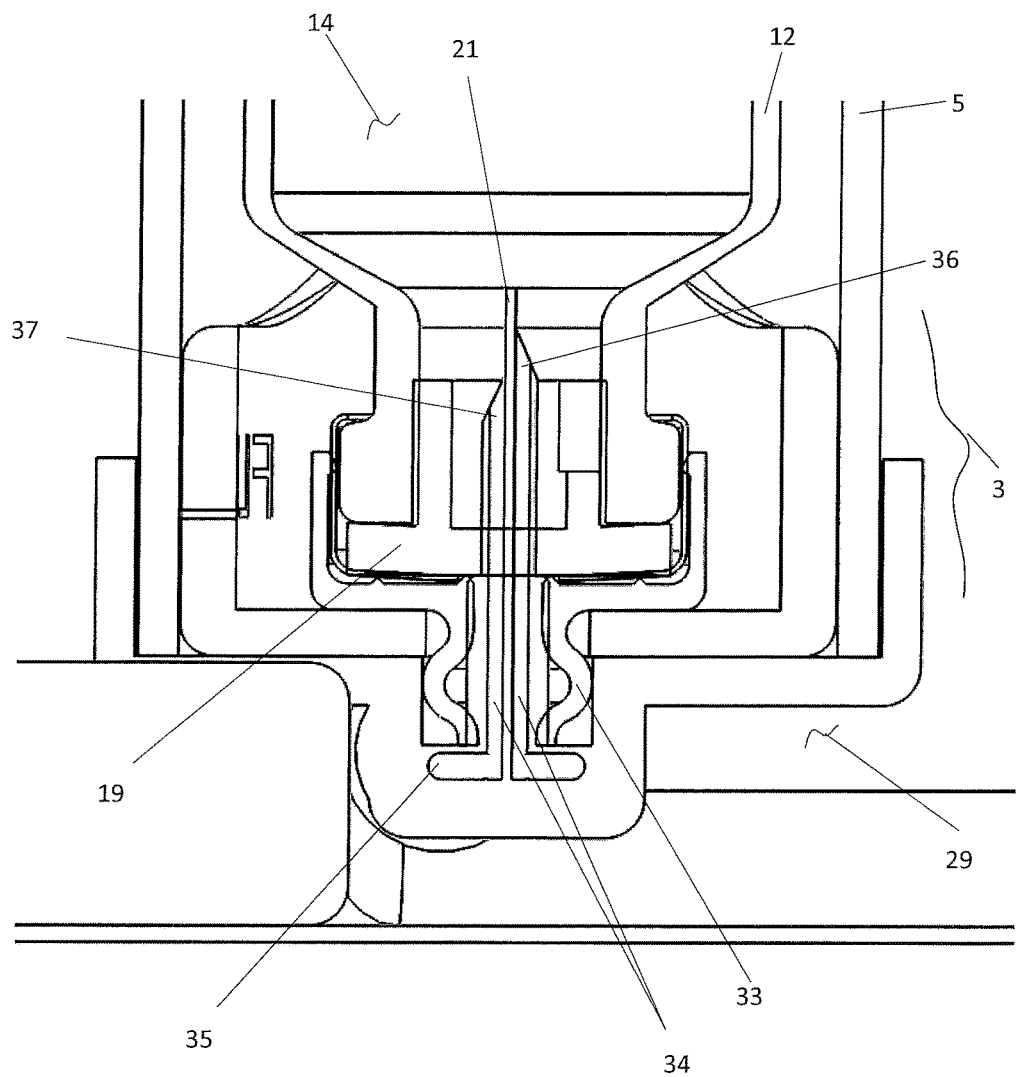
FIG. 8 is a close up of FIG. 5 illustrating the vial access member piercing the septum of the vial with the collapsible vial access member shield.

Referring to FIG. 7, the transfer apparatus 3 comprises a vial holder docking area 29 that may include elongated a vial access member or piercing member 21. This access member or piercing member 21 could be configured as pointed or blunt cannulas or needles. Referring to FIG. 8, the vial holder 5 with attached vial 12 is shown inserted into the vial docking station 29 and the vial access member 21 piercing the vial septum 19 allowing access to the contents 14 of the vial 12. The vial access member 21 may include a collapsible seal 33 to maintain sterility of the vial access member 21 and fluid path prior to activation. The collapsible seal 33 may also attach and seal on the outside of the vial 12 relative to the vial access member 21 to maintain sterility prior to activation.

Referring to FIG. 8, the vial access member 21 of the transfer apparatus 3 may comprise of multi-lumen tubes 34 to communicate with the internal fluid pathways 35 of the transfer apparatus 3. The vial access member 21 preferably comprises one inlet tube 36 allowing air or fluid to enter the vial 12 and one outlet tube 37 allowing for air or fluid to exit the vial 12. These inlet 36 and outlet 37 tubes may be separate and distinct and communicate with different fluid pathways in the transfer apparatus 3. Because of the vertical orientation of the vial 12 in the upside-down position, the lumen openings 38 in the vial access member 21 can be oriented so the inlet tube opening 36 is above the output tube opening 37. This orientation allows for introduction of pressurized air or liquid through the upper inlet tube 36 and output of the vial contents 14 through the lower output tube 37. Further, the outlet opening 37 may be positioned near the bottom of the vial 12, adjacent to the septum 19 to encourage the entire contents 14 of the vial 12 to enter the outlet port 37 and be removed from the vial 12.

Figure 9:
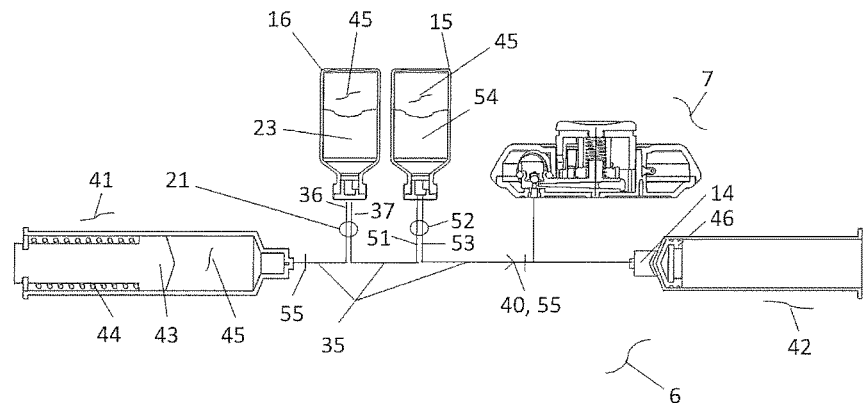
FIG. 9 is a schematic of the dual vial transfer system in FIG. 2 with a first vial, a second vial, a transfer apparatus with a first and second variable pressure chambers and injection device including the fluid pathways.
Figure 10:
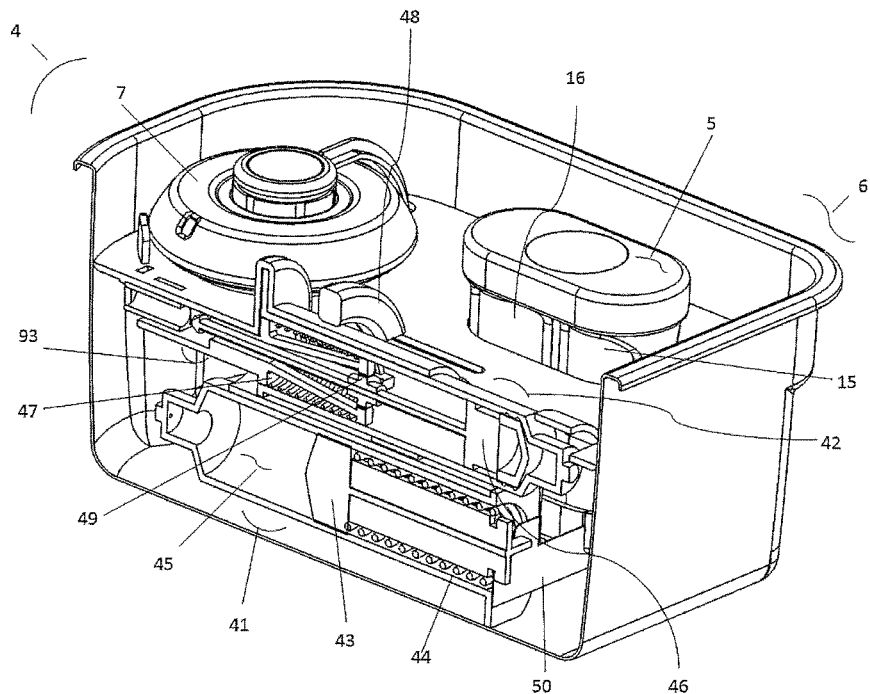
FIG. 10 is a cross-section of FIG. 2 in a pre-fire position.

Referring to FIGS. 9 and 10, the transfer apparatus 6 is configured to carry out all of the necessary steps to transfer and reconstitute (if necessary) injectable 14 contained within the vials 15,16 and transfer the mixture to the injection device 7 preferably automatically after user initiation of the process. The transfer apparatus 6 is configured and preferably includes a propulsion system or systems, such as electrically (e.g., battery powered) or mechanically (e.g., spring loaded) actuated pumps, to direct diluent from the diluent vial 16 into the injectable powder vial 15 and to direct the injectable 14 through the transfer apparatus 6 into the injection device 7.

Referring to FIGS. 9 and 10, the transfer apparatus 6 may also include an array of internal fluid pathways 35, as required to perform any transfer, reconstitution, mixing, dilution or other processing of the injectable 14 and transferring it from the vials 15, 16 in the vial holder 5 to the injection device 7. The fluid pathways 35 may include flexible or rigid conduits or tubes. These fluid pathways 35 may also include check valves, filters, flow restrictors or other means 40 to direct the drug from the vials 15, 16 through transfer apparatus 6, into the injection device 7.

Referring to FIGS. 9 and 10, the transfer apparatus 6 may include variable volume pressure chambers or cylinders that have movable spring-loaded pistons therein and directly communicate with the internal fluid pathways 35. The chamber capacity for each variable volume chamber may be defined by chamber diameter and location of the piston within the chamber. The first pressure chamber 41 in transfer apparatus 6 may preferably have an initial volume set by the manufacturer in the range of 1 to 30 milliliters. The initial contents of the first pressure chamber 41 may preferably include air 45. The piston 43 may be driven by a compression spring 44 in the first pressure chamber 41 whose volume is defined and set by the manufacturer. The spring-loaded piston 43 may be of adequate size and configuration to produce 1 to 50 psi of static air pressure in the first pressure chamber 41. The volume of air 45 will depend on the diameter of the chamber 41 and stroke position of the piston 43 during operation. This pressure will depend on the relative volume of air 45 displaced by the piston 43 and the force exerted by the spring 44. In other words, the force exerted by the spring 44 multiplied by the area of the piston 43 inside the chamber 41 will determine the static pressure within the chamber 41. The force exerted by the spring 44 at its solid height or the beginning of the stroke may be much higher than the force exerted by the spring 44 at end of its travel. The spring 44 may be appropriately sized to control the rate at which air 45 is expelled out of the pressure chamber 41 and thus the speed of the fluid transfer in the transfer apparatus 6. The first pressure chamber 41 is preferably configured to expel all of the air 45 out of the first pressure chamber 41. Alternatively, a flow restrictor 55 in the output path 35 of the pressure chamber 41 could be used to control the rate at which air 45 is expelled out of the pressure chamber 41.

Referring to FIGS. 9 and 10, the chamber volume for the second pressure chamber 42 may be set by the manufacturer. Alternatively, the filled chamber volume for the second pressure chamber 42 may be set by the user at time of use using a dose selector or volume controller 48 in the range of 0.5 to 30 milliliters. The spring-loaded piston 46 in the second pressure chamber 42 may be of adequate size and configuration to produce 1 to 200 psi of pressure in the second pressure chamber 42. A dose selector or volume controller 48 permits the user to select a prescribed dosage to be injected by the injection device 7 by setting the filled volume of chamber 42. The dose selector 48 may be of any suitable configuration. The dose selector 48 may be directly coupled to the pressure plunger assembly chamber 93 which is moveable inside the pressure chamber 42. A trigger 49 within the pressure plunger assembly 93 releases the piston 46 in the second pressure chamber 42 once the piston has reached a position corresponding to the filled volume setting. The user selects the desired dosage positions in the second pressure chamber 42 by moving the dose selector 48 which positions the pressure chamber plunger assembly 93 to define a filled chamber volume equal to the desired injection dosage. Alternatively, the position of the pressure plunger assembly 93 may already be set by the manufacture corresponding to the delivery dose and the user operates the device without making a dose adjustment.

Referring to FIGS. 9 and 10, the transfer apparatus 6 for a dual vial system 4 that provides for mixing and transfer includes a vial holder 5 with a first vial 16 and second vial 15, a first variable volume pressure chamber 41, a second variable volume dose pressure chamber 42, fluid pathways 35, and check valves 40 to direct air from the first pressure chamber 41 into the first vial 16 and the contents 23 of the first vial 16 into the second vial 15 and the resulting mixture 14 in the second vial 15 into the second pressure chamber 42 which is then transferred into the injection device 7.

Referring to FIG. 8, upon complete insertion of the vial holder 5 into the transfer apparatus 6 and the subsequent introduction of the vial access members 21 through the septums 19 and into the vial chambers 12 by the user allows for the release of the pressure chamber trigger 50 shown in FIG. 10.

Referring to FIGS. 9 and 10, release of the trigger 50 then releases the first pressure chamber spring 44 allowing the advance of the first pressure chamber piston 43 in the first pressure chamber 41 causing the air 45 in the first pressure chamber 41 to be forced through the inlet tube 36 of the first vial access member 21 and into the first vial 16 through internal passage ways 35 in the transfer apparatus 6. As more air 45 is forced out of the first pressure chamber 41 and into the first vial 16 through the inlet tube 36, the air 45 rises to the top of the first vial 16 due to its vertical orientation within the vial holder 5. The increasing air pressure in the first vial 16 causes the fluid 23 in the vial 16 to be expelled through the outlet tube 37 of the first vial access member 21 and through the inlet tube 51 of the second vial access member 52. The fluid 23 from the first vial 16 entering the second vial 15 mixes with the contents 54 of the second vial 15 containing the liquid or powdered drug and exits though the outlet tube 53 of the second vial access member 52 and into the second pressure chamber 42. In the same manner within the reconstitution configuration, the advancing plunger 43 in the first pressure chamber 41 continues to push a first fluid 23 then air 45 mixture through the first vial 16 into the second vial 15. The increasing air pressure in the top of the second vial 15 causes the reconstituted mixture 14 in the bottom of the second vial 15 to be expelled out into the second pressure chamber 42. A 'popoff' or check valve 40 or other type of valve may be present on the outlet tube 53 of the second vial access member 52 to encourage all of the contents 23 of the first vial 16 to enter the second vial 15 before the contents 14 of the second vial 15 are expelled out into the second pressure chamber 42. The valve would not open until the pressure corresponding to the plunger 43 pushing substantially all the air 45 out of the first pressure chamber 41. This ensures that the contents 54 of the second vial 15 may be thoroughly mixed with the contents 23 of the first vial 16 before the mixture 14 exits the second vial 15 and into the second pressure chamber 42. Alternatively, a flow restrictor 55 may be used in the fluid pathway 35 to delay the transfer and increase the mixing time.

Referring to FIGS. 9 and 10, injectable drug 14 flows from the second vial 15 after reconstitution, into the second pressure chamber 42, filling the chamber 42 to the extent permitted by the piston 46 position as selected using the dose indicator 48 by the user or manufacturer, which corresponds to the desired dosage. When the desired volume of the second pressure chamber 42 has been achieved, the second pressure chamber trigger 49 releases the spring 47 and forces the piston 46 forward, expelling the selected dosage of injectable drug 14 under pressure into the injection device 7. Calibration of the dose volume shown on the dose selector 48 and the actual dose received by the user may be required to account for fluid loss in the internal pathways 35 of the transfer apparatus 6. The injection device 7 is now full and ready to remove from the transfer apparatus 6.

Figure 11:
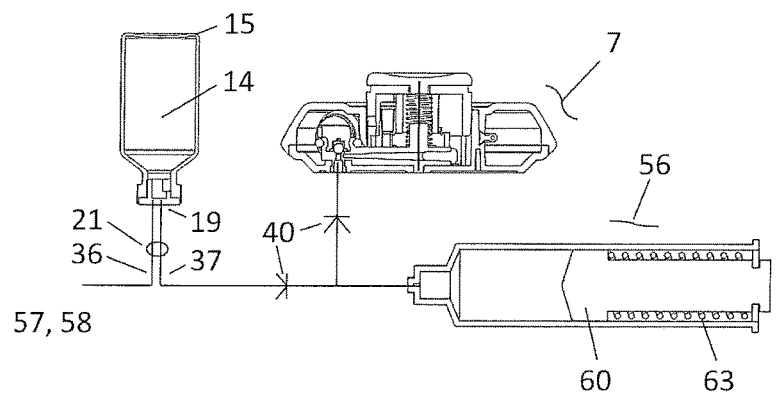
FIG. 11 is a schematic of the single vial transfer system in FIG. 1 with a drug vial, a transfer apparatus with a first variable pressure chamber and injection device including the fluid pathways.
Figure 12:
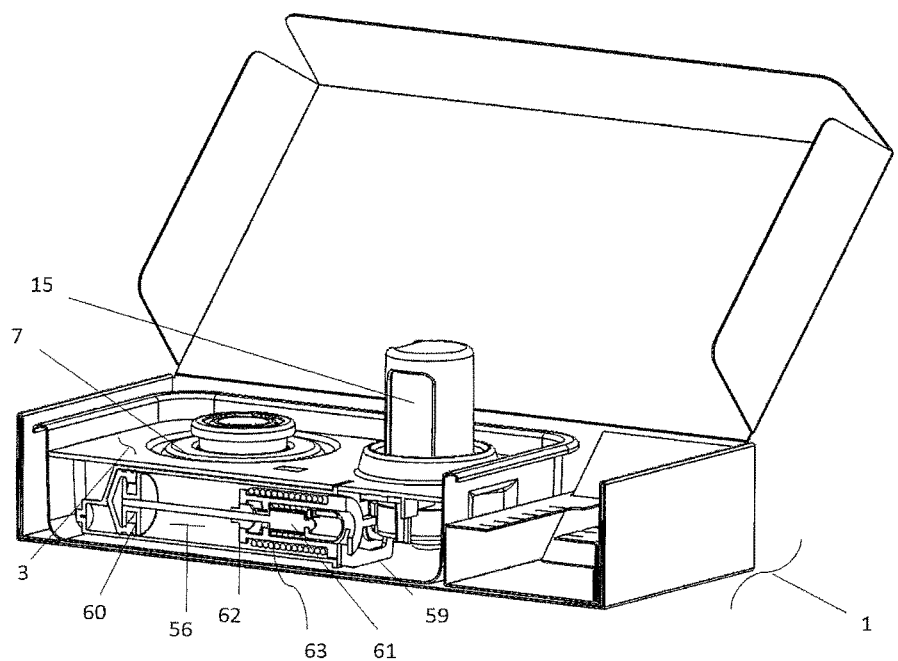
FIG. 12 is a cross-section of FIG. 1.

Referring to FIGS. 11 and 12, an alternative transfer apparatus 3 within a single vial system 1 that does not perform mixing but only transfers fluid 14 from a single vial 15 to the injection device 7 is provided. This alternative transfer apparatus 3 includes a vial holder 2 with single vial 15, a variable volume pressure chamber 56, fluid pathways 35, and check valves 40 to direct the contents 14 from the vial 15 into the injection device 7. The inlet tube 36 of the vial access member 21 is vented to the environment 57 to allow air 58 to enter the vial 1. The outlet tube 37 of the vial access member 21 is connected to the pressure chamber 56.

Referring to FIGS. 11 and 12, the full insertion of the vial holder 2 into the transfer apparatus 3 by the user causes the introduction of the vial access member 21 through the septum 19 of the vial 15 to access the contents 14 of the vial 15. This also triggers the release of the pressure chamber trigger 59. The pressure release trigger 59 releases the plunger 60 within the pressure chamber 56 connected to a withdraw spring 61. The withdraw spring 61 forces the plunger 60 to retract and withdraw fluid 14 from the vial 15 and fill the pressure chamber 56. A specified amount of fluid 14 withdrawn by the chamber 56 could be set by the manufacturer by limiting the retraction of the plunger 60. Additionally, the chamber 56 can be configured to withdraw all of the fluid 14 from the vial 15 by retracting the plunger 60 to its full travel. Once the plunger 60 reaches a set position within the pressure chamber 56, it interacts with a dispense trigger 62 that releases a dispense spring 63 to force the liquid 14 out of the pressure chamber 56 into the injection device 7. Check valves 40 could be employed to prevent fluid 14 from going back into the vial 15.

Figure 13:
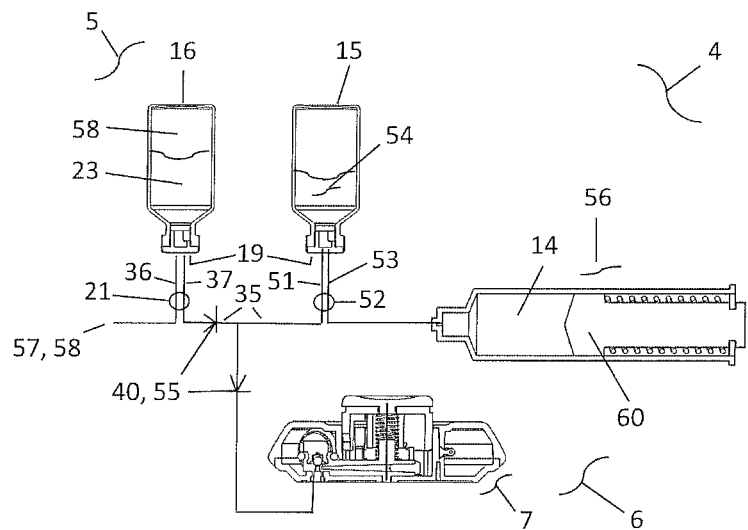
FIG. 13 is a schematic of an alternative embodiment for the dual vial transfer system in FIG. 2 with a first vial, a second vial, a transfer apparatus with a first pressure chamber and injection device including the fluid pathways.

Referring to FIG. 13, an alternative transfer apparatus 6 for a dual vial system 4 that provides for mixing and transfer includes a vial holder 5 with a first vial 16 and second vial 15, a variable volume pressure chamber 56, fluid pathways 35, and check valves 40 to direct the contents 23 of the first vial 16 into the second vial 15 and the resulting mixture 14 into the pressure chamber 56. This mixture 14 is then transferred back into the second vial 15 and then transferred into the injection device 7. In this embodiment, the inlet tube 36 of the first vial access member 21 is vented to the environment 57 to allow air 58 to enter the vial 16. The outlet tube 37 of the first vial access member 21 is connected to the inlet tube 51 of the second vial access member 52. The outlet tube 53 of the second vial access member 52 is connected to the variable volume pressure chamber 56. A fluid pathway 35 includes check valves 40 that are located between the first vial access member 21, the second vial access member 52 and the injection device 7.

Referring to FIG. 13, the full insertion of the vial holder 5 into the transfer apparatus 6 by the user causes the introduction of the vial access members 21, 52 through the septums 19 of the vials 15, 16 to access the contents 23, 54 of each vial 15, 16. This also triggers the release of the pressure chamber trigger. The pressure chamber trigger releases the plunger 60 within the pressure chamber 56 connected to a withdraw spring. The withdraw spring forces the plunger 60 to retract and withdraw fluid 23 from the first vial 16 which fills the second vial 15. This filling also results in mixing of the fluid 23 from the first vial 16 and the contents 54 of the second vial 15. The resulting mixture 14 from the second vial 15 fills the pressure chamber 56 until all of the fluid 23 is removed from the first vial 16. The rate at which the first vial 16 fills the second vial 15 can be controlled with check valves 40 or flow restrictors 55. The amount of fluid 23 withdrawn from the first vial 16 can be set in the chamber 56 by the manufacturer. Once the plunger 60 in the chamber 56 reaches a set position within the pressure chamber 56, it interacts with a dispense trigger that releases a dispense spring to force the liquid 14 out of the pressure chamber 56 back into the second vial 15. This has an advantage to allow for additional mixing of the fluid 23 from the first vial 16 and the contents 14 of the second vial 15. Once all of the fluid 14 from the chamber 56 is dispensed back to the second vial 15, the solution 14 is transferred to the injection device 7. The volume of the pressure chamber 56 could be set to be larger than the total fluid volume so that additional air 58 is drawn into chamber 56. This additional air 58 could be helpful in insuring that all of the liquid 14 is transferred into the injection device 7 that may otherwise have resided in the fluid pathways 35. Check valves 40 could be employed anywhere in the fluid pathways 35 to prevent fluid 14 from going back into the first vial 16 during transfer of the mixture 14 from the second vial 15 to the injection device 7. Flow restrictors 55 could be employed anywhere in the fluid pathway 35 to control the amount of mixing time of within the second vial 15 before transfer of the mixture 14 to the injection device 7.

Figure 14:
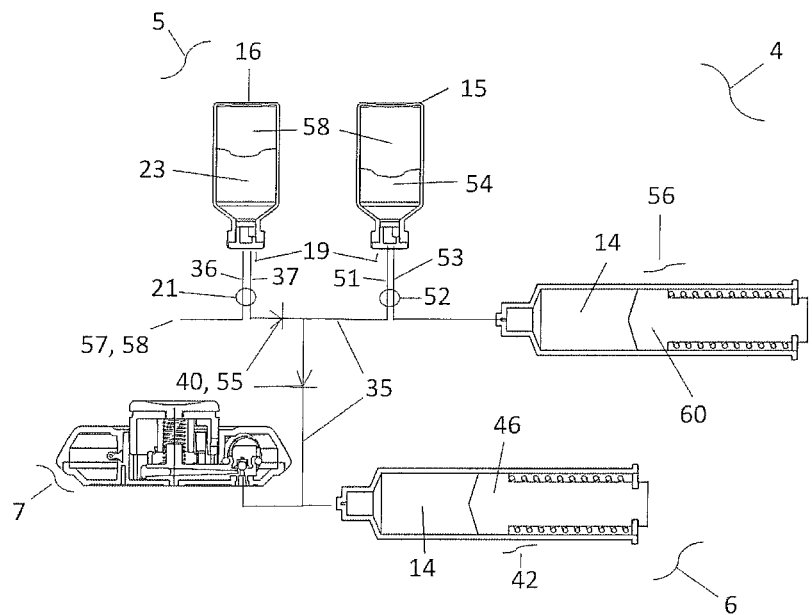
FIG. 14 is a schematic of an alternative embodiment of the dual vial transfer system in FIG. 2 with a first vial, a second vial, a transfer apparatus with a first and second variable pressure chamber and injection device including the fluid pathways.

Referring to FIG. 14, an alternative transfer apparatus 6 for a dual vial system 4 that provides for mixing and transfer includes a vial holder 5 with a first vial 16 and second vial 15, a first variable volume pressure chamber 56, a second variable volume pressure chamber 42, fluid pathways 35, and check valves 40 to direct the contents 23 of the first vial 16 into the second vial 15 and the resulting mixture 14 into the pressure chamber 56. This mixture 14 is then transferred from the first pressure chamber 56 to a second pressure chamber 42 and then transferred into the injection device 7. In this embodiment, the inlet tube 36 of the first vial access member 21 is vented to the environment 57 to allow air 58 to enter the vial 16. The outlet tube 37 of the first vial access member 21 is connected to the inlet tube 51 of the second vial access member 52. The outlet tube 53 of the second vial access member 52 is connected to the first variable volume pressure chamber 56. A fluid pathway 35 include a check valve 40 also exists between the first vial access member 21, the second vial access member 52 and the second pressure chamber 42 and the injection device 7.

Referring to FIG. 14, the full insertion of the vial holder 5 into the transfer apparatus 6 by the user causes the introduction of the vial access members 21, 52 through the septums 19 of the vials 15, 16 to access the contents 23, 54 of each vial 15, 16. This also triggers the release of the pressure chamber trigger. The pressure chamber trigger releases the plunger 60 within the pressure chamber 56 connected to a withdraw spring. The withdraw spring forces the plunger 60 to retract and withdraw fluid 23 from the first vial 16 which fills the second vial 15. This filling also results in mixing of the fluid 23 from the first vial 16 and the contents 54 of the second vial 15. The resulting mixture 14 from the second vial 15 fills the pressure chamber 56 until all of the fluid 23 is removed from the first vial 16. The rate at which the first vial 16 fills the second vial 15 can be controlled with check valves 40 or flow restrictors 55. The amount of fluid 23 withdrawn from the first vial 16 can be set in the chamber 56 by the manufacturer. Once the plunger 60 in the chamber 56 reaches a set position within the pressure chamber 56, it interacts with a dispense trigger that releases a dispense spring to force the liquid 14 out of the pressure chamber 56 back into the second vial 15. Once all of the fluid 14 from the chamber 56 is dispensed back to the second vial 15, the solution 14 is transferred into the second pressure chamber 42, filling the chamber 42 to the extent permitted by the piston 46 position as selected using the dose indicator by the user or manufacturer, which corresponds to the desired dosage. When the desired volume of the second pressure chamber 42 has been achieved, the second pressure chamber trigger releases the second pressure chamber spring and forces the piston 46 forward, expelling the selected dosage of injectable drug 14 under pressure into the injection device 7. Check valves 40 could be employed anywhere in the fluid pathway 35 to prevent fluid 14 from going back into the first vial 16 during transfer of the mixture 14 from the second vial 15 to the second pressure chamber 42 and to the injection device 7. Flow restrictors 55 could be employed anywhere in the fluid pathway 35 to control the amount of mixing time of within the second vial 15 before transfer of the mixture 14 to the second pressure chamber 42.

Figure 15:
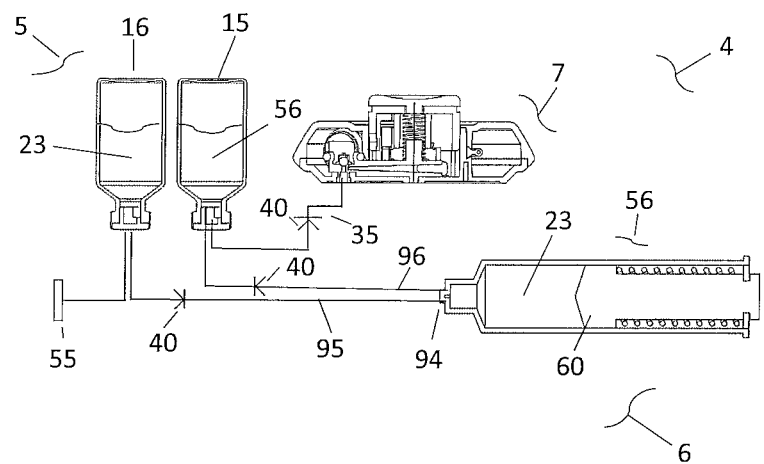
FIG. 15 is a schematic of an alternative embodiment of the dual vial transfer system in FIG. 2 with a first vial, a second vial, a transfer apparatus with a first pressure chamber, a dual lumen connector and injection device including the fluid pathways.

Referring to FIG. 15, an alternative transfer apparatus 6 for a dual vial system 4 that provides for mixing and transfer includes a vial holder 5 with a first vial 16 and second vial 15, a variable volume pressure chamber 56, a dual lumen connector 94, inlet fluid pathway 95, outlet fluid pathway 96 and check valves 40 to direct the contents 23 of the first vial 16 into the pressure chamber 56 through the inlet line 95 during retraction of the plunger 60 within the pressure chamber 56. The advancement of the plunger 60 after full retraction within the pressure chamber 56 causes the fluid contents 23 to flow from the pressure chamber 56 into the second vial 15, mix with the contents 56 of the second vial 15 and the resulting mixture 14 flows into the injection device 7. A check valve 40 in the outlet fluid pathway 96 would prevent the contents 56 of the second vial 15 from being pulled into the pressure chamber 56 during the retraction phase. A check valve 40 in the inlet fluid pathway 95 would prevent the fluid contents 23 in the pressure chamber 56 from being transferred back to the first vial 16 during advancement of the plunger 60. A check valve in the fluid pathway 35 from the second vial 15 and the injection device 7 prevents the mixture from being transferred back from the injection device 7 to the second vial 15. Flow restrictions 55 could be employed anywhere in the fluid pathways 35, 95, 96 to control the rate of fluid transfer. Alternatively, the use of the dual lumen connector 94 could also be used for a single vial transfer system 1 in the same manner to remove and advance fluid in different fluid pathways.

Figure 16:
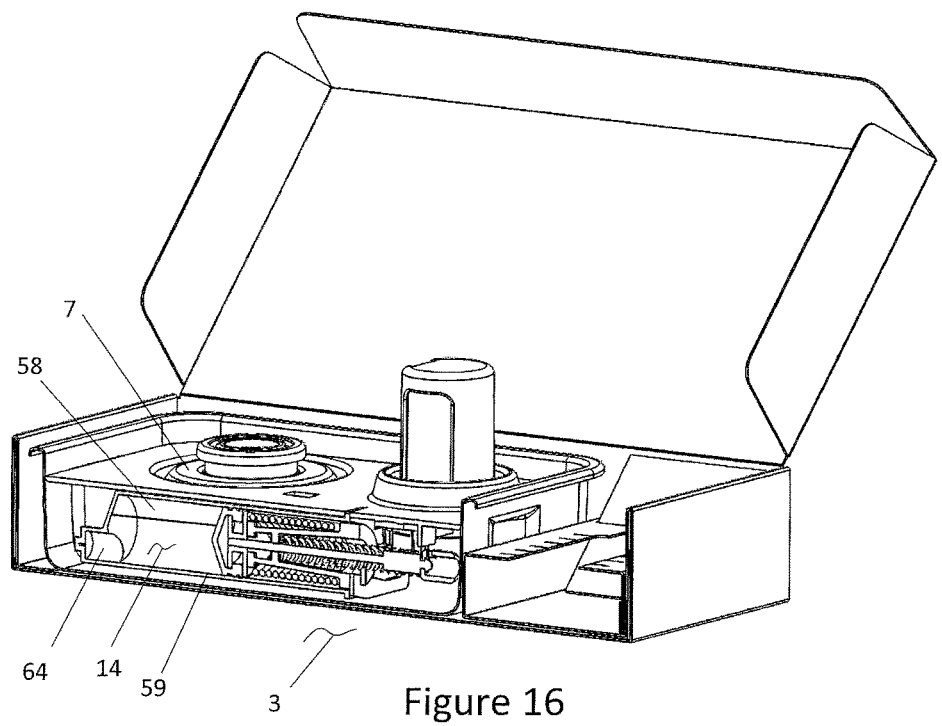
FIG. 16 is a cross-section of FIG. 1.

Referring to FIG. 16, the pressure chambers in the abovementioned embodiments may be configured with an outlet port 64 that is biased or off-center compared to a normal syringe to take advantage of gravity. When the pressure chamber 59 is filled with liquid 14 during a transfer process, there may be some air 58 that is introduced into the chamber 59 in addition to liquid 14. During the process of expelling the liquid 14 from the pressure chamber 59, it may be advantageous to control the order of when air 58 or liquid 14 is expelled from the pressure chamber 59. For example, if the outlet port 64 of the pressure chamber 59 is oriented down, during the process of expelling the liquid 14 from the pressure chamber 59, all of the liquid 14 is expelled first then the remaining air 58 is expelled last since the air bubble is oriented to the top of the pressure chamber 59. Conversely, if the outlet port 64 is oriented up, during the process of expelling the liquid 14 from the pressure chamber 59, all of the air 58 is expelled first then the remaining liquid 14 last. This has particular advantage when using hydrophobic or hydrophilic filters to remove unwanted air 58 from the lines during the transfer of liquid 14 to the injection device 7.

The transfer apparatus may employ a variety of devices or procedures to enhance mixing. For example, the transfer apparatus may inject the diluent into the drug-containing vial in a swirling manner to enhance mixing and/or may employ or introduce mixture-enhancing members such as dynamic or static mixers, e.g., mixing balls, augers or propellers, oscillating injection tubes, or the like. These techniques could be employed within the second vial or one of the syringes. Additionally, the transfer apparatus may have an intermediate chamber between the outlet tube of the second vial access member and the pressure chamber to allow for the abovementioned enhanced mixing techniques and procedures. The transfer apparatus also may be configured to move the injectable vial to induce turbulence and enhance mixing, such as by spinning the injectable vial. A flow restrictor may be used in the air or drug path to increase the transfer time to allow for greater mixing.

Figure 17:
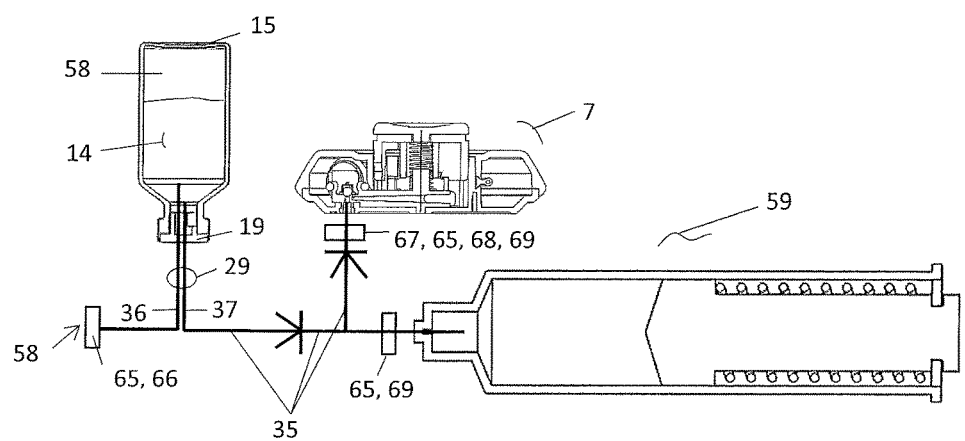
FIG. 17 is a schematic of an alternative embodiment of the single vial transfer system in FIG. 1 with a drug vial, a transfer apparatus with a first variable pressure chamber, an injection device including the fluid pathways with check valves and flow restrictors.

Referring to FIGS. 16 and 17, another optional feature of the transfer apparatus 3 is a filter 65 in the injectable fluid pathway 35 for filtering the injectable 14 to remove particulate before it is introduced into the injection device 7. The filter 65 may be a membrane, depth filter or other suitable filtration media that is of sufficiently small pore size or effective pore size to remove objectionable particulate, which may include but not be limited to undissolved injectable 14 in those situations where the injectable 14 is reconstituted by the transfer apparatus 3.

Referring to FIGS. 16 and 17, withdrawing injectable from the vial 15 may require or be enhanced by the introduction of displacement air 58 into the vial 15. In another aspect of the present subject matter, the transfer apparatus 3 may include a displacement air pathway or vent 66 that communicates with the interior of the vial(s) to allow displacement air 58 to enter the vial 15 as the injectable 14 is withdrawn. As previously discussed, the vial access member 29 for piercing the vial septum 19 may have inlet 36 and outlet 37 tubes, one for injectable 14 flowing from the vial 15 and one for displacement air 58 flowing into the vial 15. The displacement air 58 flow pathway 35 in the transfer apparatus 3 may include a sterile filter 65 such as membrane or depth filter 65 having an actual or effective pore size of about 0.22 microns or smaller for filtering the displacement air 58. Such a pore size is sufficiently small to prevent introduction of pathogens into the vial 15 with the displacement air 58, reducing the risk of contamination of the injectable 14.

Referring to FIGS. 16 and 17, the transfer apparatus 3 may include an air remover 67 in communication with injectable 14 fluid pathway 35 leading from the vial 15 to the injection device 7. Such an air remover 67 may include a bubble trap, air gap of other configuration in the injectable 14 fluid pathway 35 that removes air 58 from the injectable 14 fluid pathway 35 before it is introduced into the injection device 7. This air remover 67 may be configured with a hydrophobic filter 65 or a combination of hydrophobic 68 and hydrophilic 69 filters. A hydrophobic filter 68 would allow for the venting of air from the transfer apparatus 3 but not the passage of liquid 14. A hydrophilic filter 69 would allow the passage of liquid 14 but not the passage of particulate or air 58. The combination and position of the filter 69 in the fluid pathway 35 is preferable in removing all of the air 58 during the transfer process.

Figure 18:
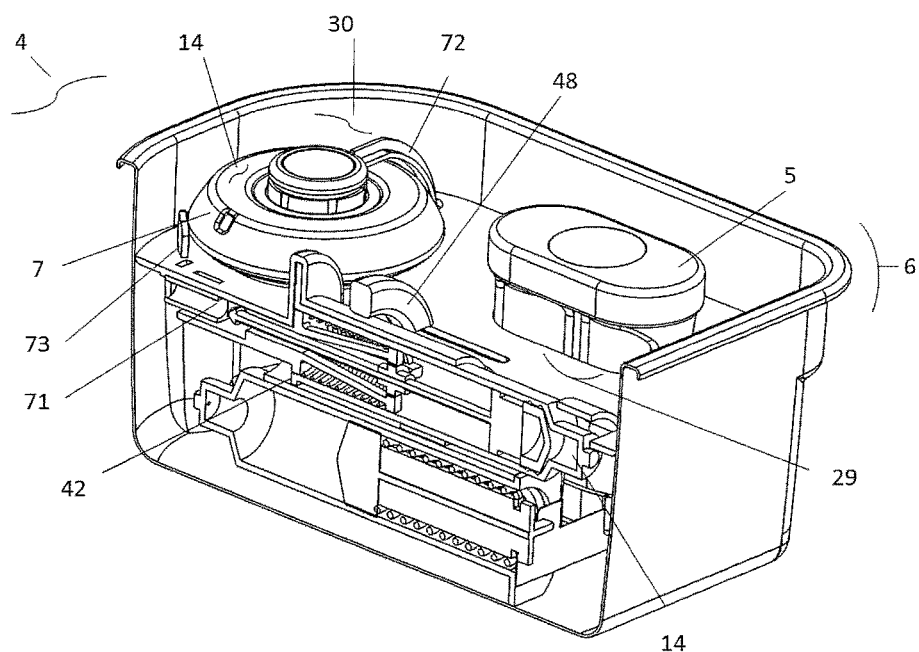
FIG. 18 is a cross-section of FIG. 2.
Figure 19:
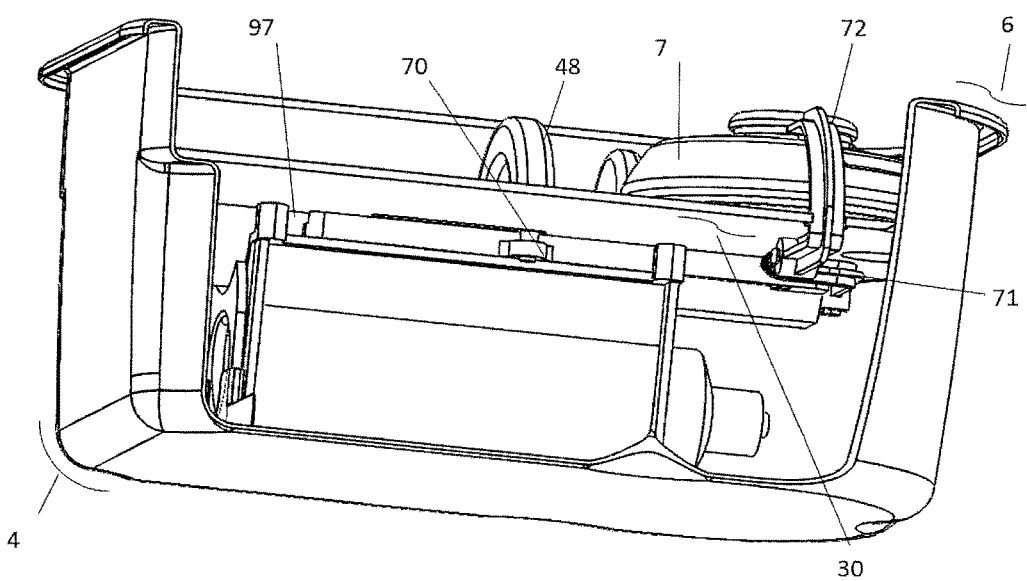
FIG. 19 is a cross-section of FIG. 2.

Referring to FIGS. 18 and 19, the transfer apparatus 6 may also have additional features as well as those described above. One such feature is an interlock 70 between the dose selector 48 and the vial docking station 29. This can be, for example, a mechanical interference member 97 that prevents the user from loading vials into the docking station 29 until a dosage has been selected. Mechanically, the dosage selector 48 may be linked to an interference member 97 at the docking station 29 which normally resides in a load-prevention position to prevents insertion of the vial holder 5 into the vial holder station 29 unless moved to a load-permitting position when the dosage member 48 is moved to a dosage selected position. Of course, for administering injectable from a vial that contains a single dose of injectable or a single vial, all of which is to be injected, the transfer apparatus need not include a dose selection capability.

Referring to FIGS. 18 and 19, the transfer apparatus 6 may include an interlock 71 between the transfer apparatus 6 and the injection device 7 to prevent the injection device from being removed prior to filling and indicate when the injection device 7 is ready for removal from the transfer apparatus 6. Mechanically, a locking pin 72 may be linked to the injection device 7 to prevent removal prior to the injection device 7 being completely filled by the transfer apparatus 6. The locking pin 72 may be part of the transfer apparatus 6 and communicate with piston in the pressure chamber 42. When the pressure chamber 42 has expelled all of the injectable 14, this may mechanically trigger the locking pin 72 to move away from the injection device 7, allow for removal of the injection device 7 from the transfer apparatus 6 by the user.

Referring to FIG. 18, the transfer apparatus 6 may include an interlock between the transfer apparatus 6 and the injection device 7 to control how the injection device 7 is removed from the transfer apparatus 6. Mechanically, a flange or other protrusion 73 on the injection device 7 may mechanically interface with an undercut in the transfer apparatus 6. This configuration may allow for one-way rotation of the injection device 7 relative to the transfer apparatus 6 for removal by the user.

Referring to FIGS. 18 and 19, the transfer apparatus 6 may include a locking feature that prevents the injection device 7 from being activated while docked on the transfer apparatus 6. For example, a mechanical interference member such as a locking pin, arch or other means 72 could extend out of the transfer apparatus 6 and mechanically lock the injection device 7 at the actuator or button in the up position. Alternatively, the mechanical interference member 72 could be a shield that covers the entire injection device 7 to prevent access to the injection device 7 while on the transfer apparatus 6. The arch or shield 72 may be part of the transfer apparatus 6 and communicate with the pressure chamber 42. When the pressure chamber 42 has expelled all of the injectable 14 into the injection device 7, this may mechanically trigger the arch or shield 72 to unlock and move away from the injection device 7. This allows access to the injection device 7 and removal from the transfer apparatus 6 by the user.

Another optional feature on the transfer apparatus is a quick release filling port or access member feature between the transfer apparatus and the injection device to allow for the quick release of the injection device from the transfer apparatus and to prevent the injection device from being reattached to the transfer apparatus. After the injection device is filled and ready to remove from the transfer apparatus, the user may remove the injection device. The filling tube or access member 83 of the transfer apparatus may be spring loaded such that when the injection device is removed from the transfer apparatus, the filling tube 83 springs down into the transfer apparatus. This allows for quick release of the tube 83 from the filling port 81 of the injection device preventing inadvertent leaking of the injection device at the filling port 81. This also makes the filling tube 83 inaccessible to the user, thus preventing reattachment of the injection device onto the transfer apparatus.

Referring to FIG. 18, the injection device 7 and transfer apparatus 6 are preferably configured for removable attachment of the injection device 7. In the current embodiment, after transfer of the injectable fluid 14 from the second pressure chamber 42 within the transfer apparatus 6 into the injection device 7 and release of the interlock 71 on the transfer apparatus 6, the injection device 7 is ready to be separated from injection device docking station 30 of the transfer apparatus 6 for application to the skin of a subject. As previously mentioned, alternative embodiments described herein include the transfer of the injectable fluid from a single pressure chamber directly to the injection device.

Figure 20:
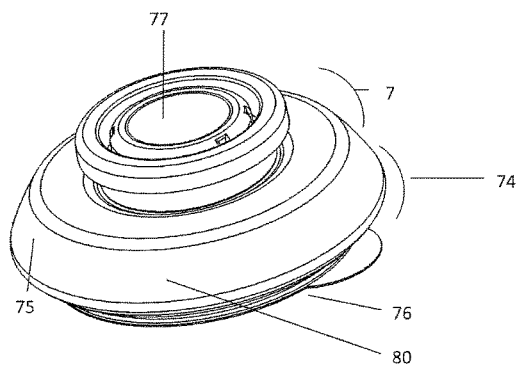
FIG. 20 is a perspective view of the injection device.

Referring to FIG. 20, the injection device 7 may be of any suitable configuration. As explained earlier, the injection device may advantageously employ one or more of the features of the injection devices described in U.S. patent application Ser. No. 61/326,492 filed Apr. 21, 2010; U.S. patent application Ser. No. 13/637,756, filed Sep. 27, 2012; and U.S. patent application No. 61/704,922, filed Sep. 24, 2012, which are all hereby incorporated by reference herein.

Figure 21:
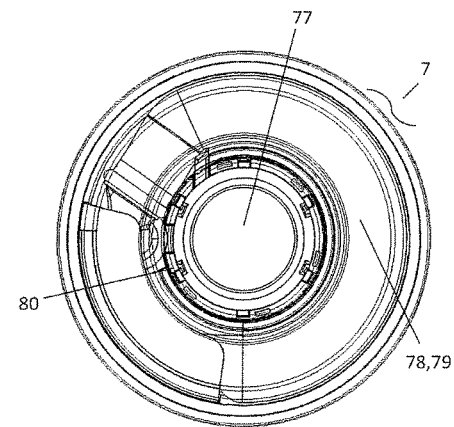
FIG. 21 is a top view of a filled injection device showing the delivery indicator in a full state.
Figure 22:
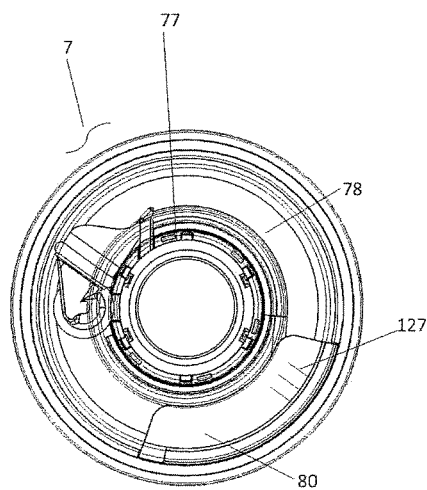
FIG. 22 is top view of a filled injection device showing the delivery indicator in an empty state.

Referring to FIGS. 20-22, the injection device 7 has a generally low-profile, disc shaped outer housing 74 with an upper surface 75 and a lower surface 76, through which an injection needle or cannula protrudes when actuated by the user. The upper surface 75 has an actuator or button 77 to start the injection and a clear section 80 of the housing 74 that allows the subject or medical professional to view the expandable member 78 to ascertain the amount of injectable fluid 79 in the device 7. For example, the user could determine whether the injection has commenced or concluded. More preferably, the expandable member 78 and/or the clear section 80 of the housing 74 may be graduated, such as by line markings 127 or the like, so that the patient or medical professional can visually determine the amount of injectable fluid 79 remaining with greater precision— such as, for example, about 50% complete or about 75% complete. In addition, the expandable member 78 may itself include or interact with a feature on the outer housing 74 to show the amount of injectable fluid 79 remaining. For example, when the injection device 7 is full of drug 79, the clear section 80 may show one color such as but not limited to green. When the injection device 7 is empty of drug 79, the clear section 80 may show a different color such as but not limited to red. In the middle of dispense, the clear section 80 could show a combination of colors.

Figure 23:
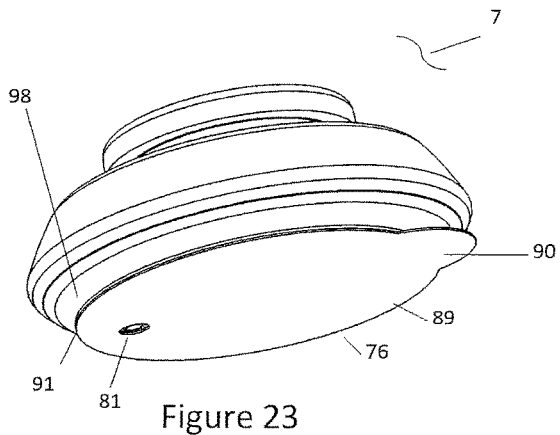
FIG. 23 is a perspective view showing the underside of the injection device with attached tape and fill port.
Figure 24:
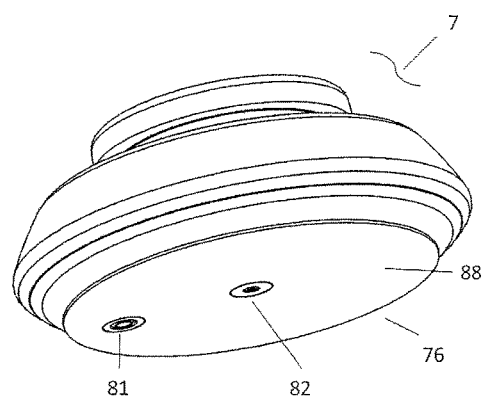
FIG. 24 is a perspective view showing the underside of the injection device with tape detached and the fill and dispense ports exposed.
Figure 25:
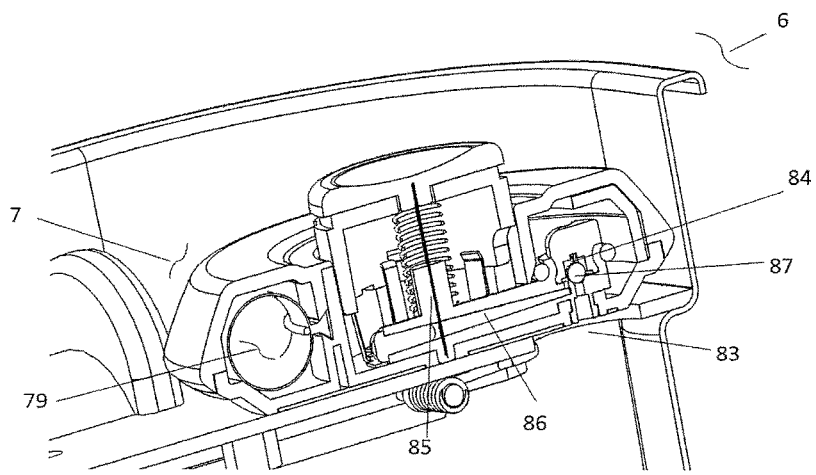
FIG. 25 is a cross-section of the injection device on the transfer apparatus.

Referring to FIGS. 23-25, the undersurface 76 of the injection device 7 includes a filling port 81 and a dispense port 82. The filling port 81 is the interface that allows the transfer apparatus filling tube 83 to transfer liquid 79 to the injection device 7. The dispense port 82 also contains an internal pathway 84 between the expelled injectable 79 from the expandable member 78 and the needle 85. The filling port 81 and dispense port 79 may be in direct fluid communication through internal pathways 86, or they may be combined into a single port.

Referring to FIGS. 23-25, the injection device may preferably include a filling port 81 that includes a check valve 87 to prevent pressurized injectable 79 from leaking out of the injection device 7 when the injection device 7 is removed from the transfer apparatus 6 and the filling port 81 is removed from the filling tube 83.

Referring to FIGS. 23-25, the injection device 7 may also have a filling port 81 that is configured to accept the insertion of a syringe. This syringe may be configured with a luer fitting or a needle. This filling port 81 configuration allows for the manual filling of the injection device by the user. The transfer apparatus 6 may still be used but would not be required in this configuration.

Referring to FIGS. 23-25, the injection device 7 may also have a dispense port 82 that is configured to directly connect to an intravenous cannula via attached tubing or a standard needle port.

Referring to FIGS. 23-25, the undersurface 76 of the injection device 7 carries an adhesive 88 for securing the injection device 7 temporarily to the skin of a subject until the injection is complete. During removal of the injection device 7, an adhesive tape liner 89 may be removed automatically exposing an adhesive surface 88 on the undersurface 76 of the injection device 7 that may be used to adhere the injection device 7 to the patient's skin. Alternatively, the tape liner 89 may have a tab 90 that the user pulls to manually remove before adhering the injection device 7 to the skin. Alternatively this tab may be attached to the surface of the transfer device 4 so that the tape liner is automatically removed upon removal of the injection device 7.

Referring to FIGS. 23-25, the injection device 7 may have an adhesive tape flange 91 that extends beyond the undersurface base 76. This flange 91 of adhesive tape 88 can act as a strain relief between the injection device 7 and skin surface, reducing the risk of accidentally dislodging the injection device 7 from the skin. In other words, similar to a tapered strain relief on a wire where it enters into a connector, the extended adhesive flange 91 acts to distribute the load on both sides of the connection point between the adhesive tape 88 and the undersurface base 76 of the injection device 7 to reduce any stress risers at the adhesive tape 88 and skin interface.

Referring to FIGS. 23-25, the injection device 7 may be configured with a tapered underside surface 98 that presses on the adhesive flange 91 to securely attach the adhesive tape 88 to the skin as the user is securing the injection device 7 to the skin without additional user intervention. By using the compliance of a person's skin when pressing the injection device 7 against the skin, the tapered underside surface 98 of the injection device 7 effectively presses the flange 91 of the adhesive tape 88 against the skin but the upper exposed surface of the flange 91 portion does not have exposed adhesive and therefore is not attached to that portion of the tapered underside surface 98. The user is not required to run their finger around the flange 91 to secure the injection device 7 to the skin making it a much simpler method of adhesive tape 88 attachment.

Referring to FIGS. 23-25, the injection device 7 may have an underside surface 76 that is flexible or compliant in lieu of being rigid to allow for improved attachment by conforming of the injection device 7 to the skin during application.

Figure 26:
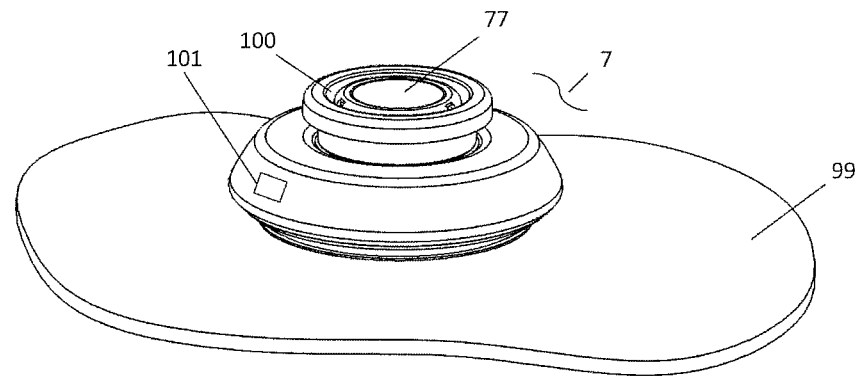
FIG. 26 is a perspective view of the injection device attached to the skin with the safety device installed.
Figure 27:
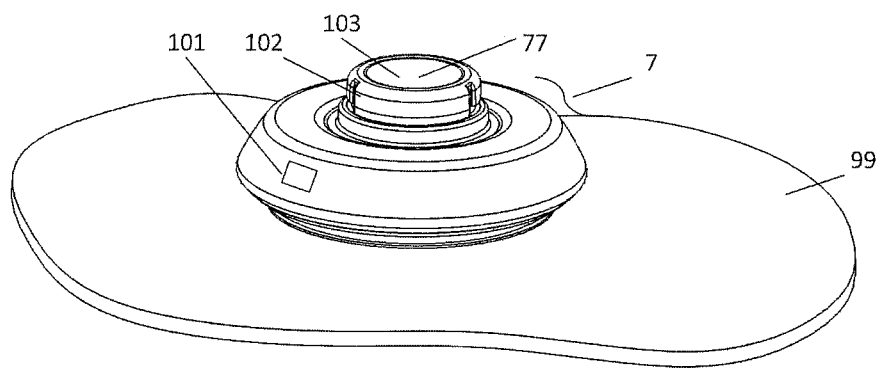
FIG. 27 is a perspective view of the injection device attached to the skin with the safety device removed and the button up in a pre-fire state.
Figure 28:
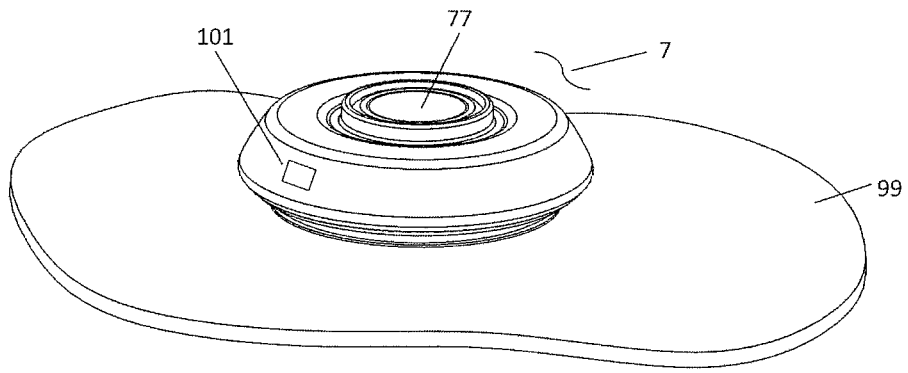
FIG. 28 is a perspective view of the injection device attached to the skin with the safety device removed and the button down in a fired state.

Referring to FIGS. 26-28, after the injection device 7 is placed against or adhered to the skin 99, a safety mechanism or lock-out mechanism may be automatically released and the injection device 7 is ready to fire (inject). In other words, the injection device 7 is prevented from being actuated (it is locked out) until it is placed against the skin. Alternatively, the user may manually remove a safety 100 such as a safety pin, safety sleeve, or collar to release the injection device to be ready to fire (inject). The injection device 7 preferably cannot be fired until the safety mechanism 100 is released. The safety mechanism 100 may be passive or active and manually triggered by the user or automatically triggered by the injection device 7.

Referring to FIGS. 26-28, the injection device 7 may use an actuator or button 77 and a visual indicator 101 in combination to define the state of the injection device 7 after it has been removed from the transfer apparatus. For example, when the button 77 is in the up position and the indicator 101 has one color such as but not limited to green, this may indicate that the injection device 7 is ready to start the injection. Additionally, the button 77 may have a side wall 102 that is a different color from its top 103. When the button 77 is depressed, the user cannot see the sidewall 102 of the button 77; this may indicate that the injection device 7 is in use. The injection device 7 may alert the user when the injection of the drug is completed. This alert could be in the form of visual indicators, audible sounds, mechanical movements or a combination. The button 77 is ideally designed to give the user audible, visual and tactile feedback when the button 77 'pops up' into the locked-out position. The injection device 7 may indicate to the user that it is has completed dispensing and the full dose has been delivered to the patient with the button 77 in the up position and indicator window 101 showing the injection device is empty. For example, when the button 77 is in the up position and indicator 101 shows a different color such as but not limited to red, this may indicate that the injection device 7 has completed the injection.

Figure 29:
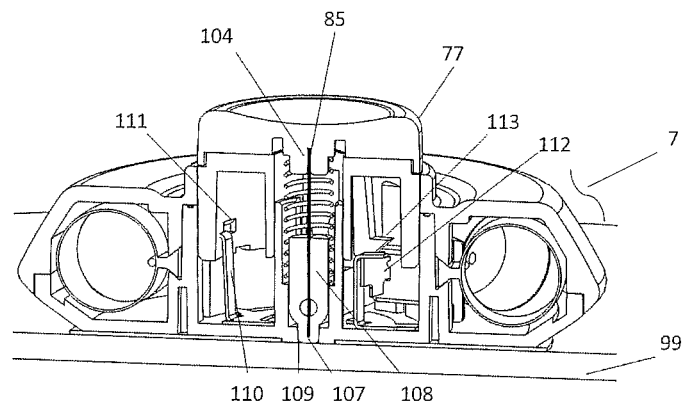
FIG. 29 is a cross-section view of the injection device attached to the skin with the button up in a pre-fire state.
Figure 30:
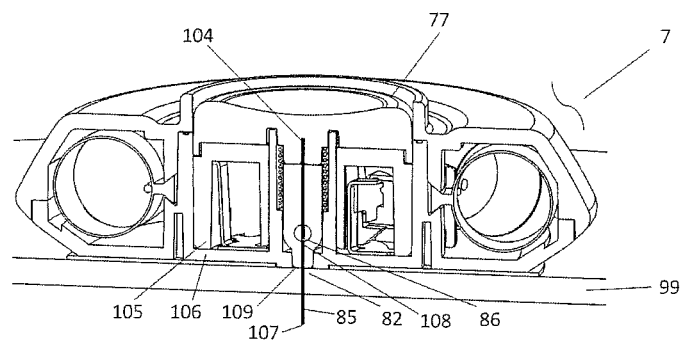
FIG. 30 is a cross-section view of the injection device attached to the skin with button down in a first fired state.
Figure 31:
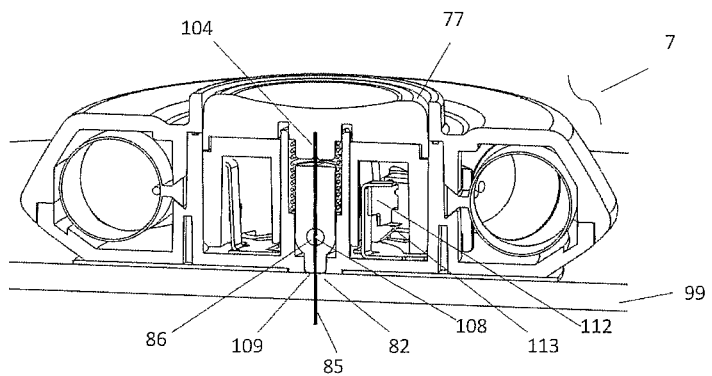
FIG. 31 is a cross-section view of the injection device attached to the skin with button down in a dispense state.

Referring to FIGS. 29-31, the injection device 7 may have an actuator or button 77 that the user depresses on the injection device 7 to start the injection. The button 77 may be configured to be an on/off switch, i.e., to only have two states, open and closed such as a light switch. This may prevent the user from pushing the button 77 half way and not actuating the injection device 7. Once activated, this 'light switch' type button 77 would insert the needle 85 rapidly into the skin 99, independent of the user manipulation of the button 77. Alternatively, the button 77 could have a continuous motion, allowing the user to slowly insert the needle 85 into skin 99. The button 77 may preferably be directly coupled to the needle 85 by using adhesive 104 creating a button 77 and needle 85.

Referring to FIGS. 29-31, the injection device 7 may have a needle 85 travel into the skin 99, upon actuation of the button 77 that initially goes to a first position or depth as shown in FIG. 30 and retracts slightly to a second position of depth preferably automatically as shown in FIG. 31. The first depth shown in FIG. 30 is achieved from over travel of the button 77 during actuation. The first depth may be controlled by features 105 in the button 77 in direct contact with the base 106 of the injection device 7. The final depth of the needle 85 is suitable for subcutaneous injections. Alternatively, the final depth of the needle 85 may be reduced for intradermal injections. Alternatively, the final depth of the needle 85 may be increased for intramuscular injections. Upon reaching the first depth, the needle 85 retracts back to a second depth as shown in FIG. 31. The retraction distance of the needle to the second depth is in the range of 0.1-2 mm. This retraction feature is preferable to prevent the needle 85 from being blocked by tissue during the initial insertion process. This tissue blockage could require a very high pressure to overcome and prevent the injection device 7 from delivering the drug. The retraction of the needle 85 from the first position to a second position creates an open pocket ahead of the needle tip 107 allowing reduced pressure for initiation of flow of drug from the needle 85. This reduced pressure for initiation of the flow of drug from the needle is preferable for the injection device 7 to maintain a relatively constant pressure during injection.

Referring to FIGS. 29-31, the injection device 7 may include a needle 85 with a side hole 108. As shown in FIG. 31, once the button 77 on the injection device 7 is fully depressed, the needle 85 will be fully inserted into the skin 99 through the dispense port 82 and the injection device 7 will begin dispensing of the injectable. Until the button 77 is fully depressed, the side-hole 108 and therefore the internal lumen of the needle 85 is not in communication with the fluid channel 86 of the dispense port 82. Both the side-hole 108 and needle-tip 107 are retained within a septum 109. With the side-hole 108 and needle-tip 107 being retained within the septum 109, the entire drug path is kept sterile until the time of use. When the button 77 is fully depressed and the needle 85 is in the dispense position, a side hole 108 in the needle 85 is in communication with the fluid channel 86 of the dispense port 82 and the injection of the liquid begins.

Referring to FIGS. 29-31, the septum 109 provides the advantage of sealing the needle tip 107 as well as the side hole 108 from the injectable before and after dispense. Sealing the needle tip 107 and the side hole 108 of the needle 85 at the end of the injection has a particular advantage to prevent dripping of injectable from the injection device 7 after end of dispense and/or after it is removed from the skin surface. It also prevents contaminates from entering the hollow needle prior to being actuated into the skin. The septum 109 may be made of any suitable material to allow for sealing once the needle 85 has punctured it. The material composition of septum 109 may preferably be silicone. Alternatively, the material composition of the septum may also be a blend of different materials including but not limited to bromobutyl, chlorobutyl, isoprene, polyisoprene, SBR, polybudtadiene, EPDM, natural rubber and silicone. Alternatively, the fluid pathway 86 including the dispense port 82 could be a rigid plastic with a silicone injected overmold to produce the septum previously described.

Referring to FIGS. 29-31, the septum 109 at the dispense port 82 could protrude slightly from the underneath surface into the skin surface 99 of the injection device 7 to provide for pressure on the skin surface 99 at the injection site. This pressure on the skin surface 99 by the dispense port 82 after the needle is retracted could eliminate injectable from coming out of the injection site commonly referred to as blow-back.

Referring to FIGS. 29-31, the injection device 7 may include a set of spring tabs 110 that interface with the button 77 to perform locking functions. A spring tab 110 is biased to lock into an undercut 111 in the button 77 to keep the button 77 in a first up position or pre-fire position as shown in FIG. 29. The geometry of the undercut 111 and spring tab 110 help to produce the light switch actuation force described previously. This light switch actuation is accomplished by the translation of the button 77 relative to the spring tab 110 and the geometry of the mating undercut 111 surfaces.

Referring to FIGS. 29-31, the injection device 7 may include a spring tab 112 that interact with the button 77 in the injection device 7 to perform locking functions such that when the button 77 is actuated to the first depth and retracts slightly back to the second depth or dispense position, undercut features 113 in the button 77 allow a spring tab 112 to hold the button 77 in the dispense position until the injection device 7 has completed dispensing.

Figure 32:
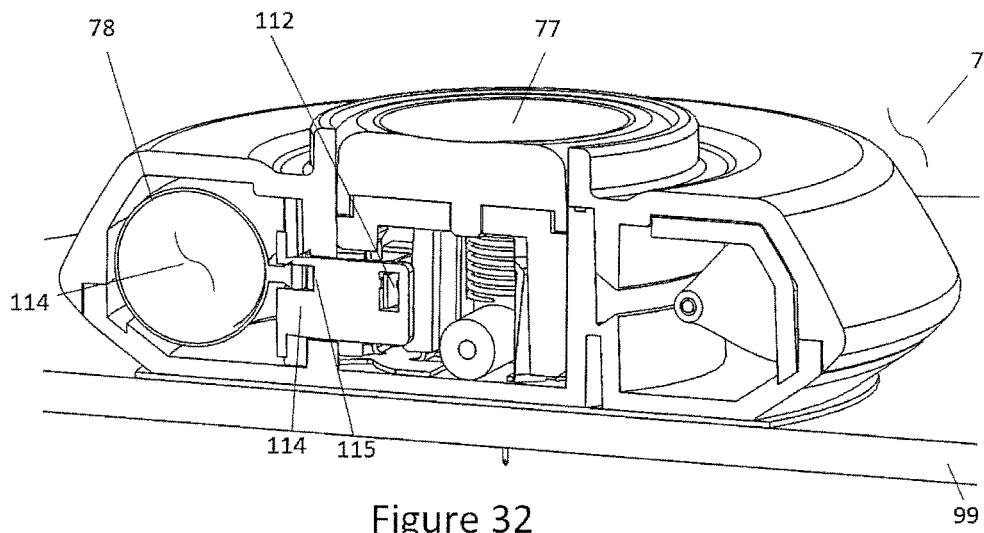
FIG. 32 is a cross-section view of the injection device attached to the skin showing the end of delivery indicator not triggered.
Figure 33:
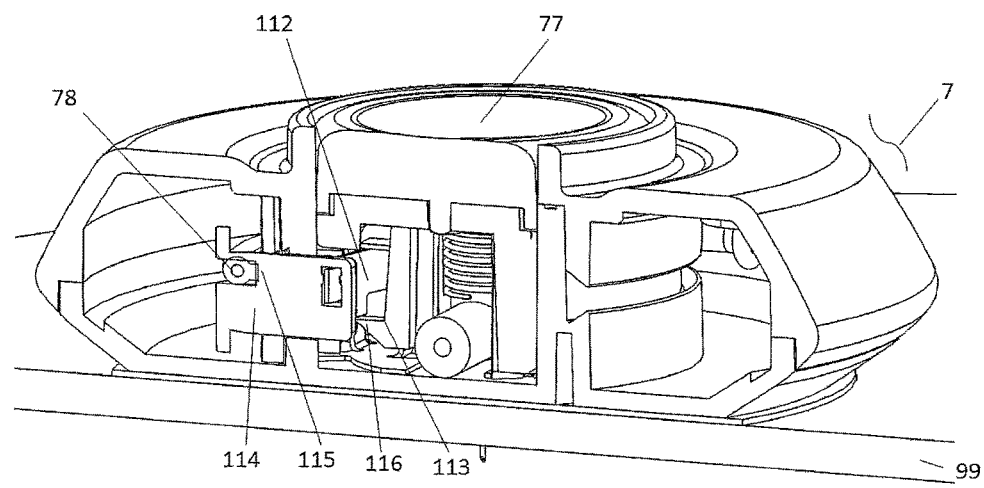
FIG. 33 is a cross-section view of the injection device attached to the skin showing the end of delivery indicator triggered.

Referring to FIGS. 32-33, the injection device 7 may include an end of delivery indication or empty indicator 114 to sense when all of the fluid 79 has been expelled from the expandable member 78 and the injection device 7 has completed dispensing. The empty indicator 114 may be configured with a slot or other opening 115 to slide over the expandable member 78 at the exit port when the expandable member 78 is in a deflated state after all of the fluid has been expelled. There may be two states of the empty indicator. As shown in FIG. 32, the empty indicator may be in a first position or deflected-out state when the expandable member 78 is full with fluid 79 at that section and is not contained within the slot or opening 115. This first position would translate to a non-empty state of the expandable member 78 when the diameter of the expandable member 78 is larger than its minimum due to residual fluid 79 contained within. As shown in FIG. 33, the empty indicator 114 may be in a second position or deflected-in state when the expandable member 78 is partially or fully contained within the slot or opening 115. This second position would translate to an empty state of the expandable member 78 when the diameter is at a minimum.

Referring to FIGS. 32-33, the injection device 7 may include an automatic needle retraction mechanism at the end of dispense. This mechanism includes a direct coupling between a spring tab 112, button undercut feature 113 and the empty indicator 114, all previously mentioned. When the expandable member 78 is filled with injectable 79 and the button 77 is depressed from a first pre-fire position to a second dispense position as shown in FIG. 33, undercut features 113 in the button 77 allow a spring tab 112 to hold the button 77 in the dispense position until the injection device 7 has completed dispensing. This spring tab 112 may also be directly coupled to the empty indicator 114 which is naturally in the first position or deflected-out state. The motion of depressing the button 77 to a second position or dispense position allows a post feature 116 in the button 77 to provide a bias or pre-tension on the spring tab 112 to urge the empty indicator 114 to its second position or deflected-in state. However, since the expandable member 78 is initially full with injectable 79 at a large diameter, the empty indicator 114 cannot move to the second position or deflected-in state as shown in FIG. 32. After the button 77 is depressed, the fluid 79 starts to expel out of the expandable member 78 through the needle as previously mentioned. Once the expandable member 78 has expelled all of the fluid 79 and is at a minimum diameter, the empty indicator 114 (under pretension from the spring tab 112) will move to the second position or deflected-in state as shown in FIG. 33. The spring tab 112 directly coupled to the empty indicator 114 also moves with the empty indicator 114. This movement releases the spring tab 112 from the undercut feature 113 in the button 77 to allow the button 77 (and needle) to move up to a final position or post fire position after the dispense is completed as shown in FIG. 34.

Figure 34:
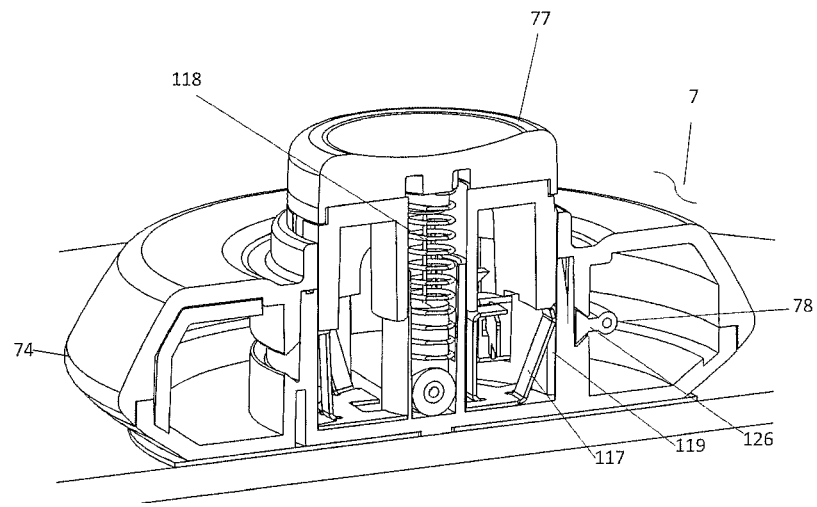
FIG. 34 is a cross-section view of the injection device attached to the skin with button locked up in a post-fired state.

Referring to FIG. 34, lock out spring tabs 117 may also interact with the button 77 in the injection device 7 to perform locking functions such that when the injection is complete the button 77 is released, and the button 77 is urged up by the return spring 118 to a final up position or post-fire position. The button height 77 relative to the top of the injection device 7 in the final up position or post-fire position (shown in FIG. 34) may be higher than the pre-firing position (shown in FIG. 29). The end of the lock out spring tabs 117 move out to the outer diameter surface 119 of the button 77 within the outer housing 74 to lock the button 77 in the up position or post-fire position and prevent the button 77 from being actuated again.

Referring to FIG. 34, the injection device 7 may include a return spring 118 that interacts with the button 77 to provide a bias to the button 77 into a first up position or pre-fire position. When the button is actuated down to a second depth or dispense position, the return spring 118 is compressed causing more of a bias or preload. At the end of the dispense period, the button 77 is unlocked from the second depth or dispense position (shown in FIG. 31) to move up to a final position or post fire position after the dispense is completed as previously mentioned. It is the bias of the return spring 118 that forces the button 77 up to a final position or post-fire position.

Figure 35:
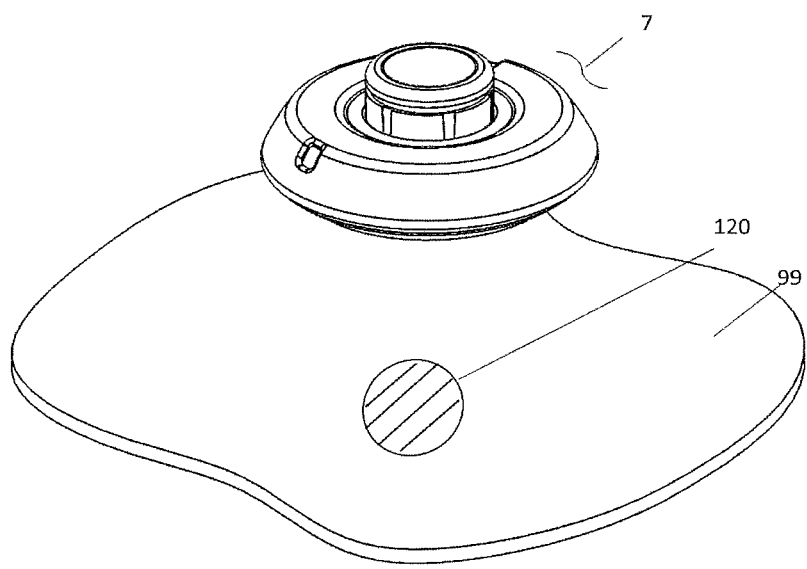
FIG. 35 is a perspective view of the injection device removed from the skin with the bandage remaining on the skin.

Referring to FIG. 34-35, upon removal of the injection device 7 from the skin 99, the injection device 7 will preferably be locked out, preventing non-destructive access to the needle or reuse of the injection device 7. The injection device 7 may indicate to the user that the full dose has been delivered. This indication could be in the form of a visual indictor, audible sound, mechanical movement or a combination.

Referring to FIG. 35, upon removal of the injection device 7 from the skin 35, a bandage 120 may release from the injection device 7 and remain on the skin surface 35. This can be affected by using an adhesive on the bandage portion that more strongly attaches the bandage to the skin than the adhesive that attaches the bandage to the injection device 7. Thus when the housing is lifted from the skin, the bandage 120 remains in place over the injection site as described in U.S. Pat. No. 7,637,891 and U.S. patent application Ser. No. 12/630,996, filed Dec. 4, 2009 incorporated by reference herein.

Referring to FIGS. 36-39, the injection device 7 may preferably include a manifold 121 that assembles to both the expandable member 78 and the filling port 81 and dispensing ports 82, and provides direct fluid communication between the expandable member 78 and the filling 81 and dispensing 82 ports of the injection device 7. The manifold 121 may be configured on the end that assembles to the expandable member 78 to be large in diameter to facilitate filling and expelling all of the fluid 79 out of the expandable member 78 as previously discussed. The manifold 121 may preferably include internal passageways 122 to allow for fluid flow in and out of the expandable member 78. The manifold 121 may be configured with a filter 123 in the injectable fluid pathway 122 for filtering the injectable 79 to remove particulate before and after it is introduced into the expandable member 78. The filter 123 may be a membrane, depth filter or other suitable filtration media that is of sufficiently small pore size or effective pore size to remove objectionable particulate, which may include but not be limited to undissolved injectable 79 in those situations where the injectable 79 is reconstituted by the transfer apparatus. The manifold 121 may also be configured with a filter 123 for the removal or air. Such an air remover filter 123 may include a bubble trap, air gap of other configuration in the injectable fluid pathway 122 that removes air from the injectable fluid pathway 122 before it is introduced into the expandable member 78. This air remover filter 123 may be configured with a hydrophobic filter or a combination of hydrophobic and hydrophilic filters. A hydrophobic filter would allow for the venting of air from the transfer apparatus but not the passage of liquid. A hydrophilic filter would allow the passage of liquid but not the passage of particulate or air. The air remover filter 123 may also have check valves to allow for venting of trapped air. Alternately, the air remover and filters 123 may be located at any point in the fluid pathway from the filling port 81 to the needle 85. For example, the most downstream point in the fluid pathway is the distal end 128 of the expandable member 78. An internal mandrel 124 may be connected to distal end 128 of the expandable member 78. An air remover or filter 123 may be integrated into this downstream point to allow for venting of trapped air during filling of the injection device 7. Furthermore, the mandrel 124 could include a slot along its length that is in communication with the downstream filter 123 to aid in the venting of air during the filling process.

Referring to FIGS. 36-39, the injection device 7 may include a resilient expandable member 78 such as an elastomeric balloon or bladder. The material composition of expandable member 78 may preferably be silicone. Alternatively, the material composition of the expandable member 78 may also be a blend of different materials including but not limited to bromobutyl, chlorobutyl, isoprene, polyisoprene, SBR, polybudtadiene, EPDM, natural rubber and silicone. In addition, the expandable member 78 may be coated to improve their surface properties. Coatings may include parylene, silicone, Teflon and fluorine gas treatments. Alternatively, the expandable member 78 may be made from a thermoplastic elastomer.

Referring to FIGS. 36-39, the injection device 7 may include a resilient expandable member 78 which the injectable 79 is transferred under pressure. This causes the expandable member 78 to enlarge and the resilience of the expandable member 78 creates a pressure which tends to expel the injectable 79. The pressure chamber of the transfer apparatus described previously (or such other pump or pressurizing means as may be employed in the transfer apparatus) transfers the injectable 79 to the injection device 7 under pressure. Introducing the injectable 79 into the expandable member 78 under pressure causes it to stretch and expand both in diameter and length. An example of this would be blowing up a long, skinny balloon. The volume range of the injection device 7 may be 0.5 to 30 milliliter. When expanded, the resilient expandable member 78 exerts an expulsion pressure in the range of 1 to 200 psi on the injectable 79 contained in the expandable member 78 so that the injection device 7 is ready to administer the injectable 79 automatically when triggered by the user by depression of the button as previously described. Thus, the transfer apparatus as previously described operates not only to transfer a measured amount of injectable 79 (and if necessary mix, dilute and filter it) to the injection device 7, but also simultaneously charges or provides the motive pressure to the injection device 7 (by expanding the resilient expandable member 78) so that the injection device 7 is ready to automatically dispense the injectable 79 under the pressure exerted by the resilient expandable member 78 when actuated by the user.

This aspect of the transfer apparatus (simultaneous transferring and charging) is particularly beneficial. While the above applications show the injection device 7 in a pre-filled or charged condition for injection of the drug 79 when the injection device 7 is actuated, the present disclosure contemplates that the injection device 7 can remain empty and the expandable member 78 in a more relaxed and unfilled condition, i.e., in a non-charged or non-filled condition, until administration of the injectable 79 is required. Only then is the injectable 79 mixed or processed as necessary and introduced into the injection device 7, expanding the expandable member 78 to a filled (charged) condition. In the present disclosure, the drug is stored in its original container closure (vial) until the time of use. Because the injectable 79 will typically be injected within seconds to hours after transfer from the vial into injection device 7, shelf life and material compatibility of the drug with the materials in the fluid pathway within the injection device 7 are not significant issues. The challenges and expense of designing an injection device 7 and selecting materials for an extended shelf life of pre-filled injection device 7 are significantly reduced.

Referring to FIGS. 36-39, the present subject matter may use features of the injection device 7 described in the patent applications incorporated by reference herein as previously described. However, the expandable member 78 employed in the injection device 7 here may also preferably take the form of an elongated balloon or bladder arranged, for example, in a planar helical or spiral configuration as illustrated. As previously mentioned, the injection device 7 includes a circular shaped outer housing 74 that has a spiral slot or recess 125 formed therein. The elongated balloon or bladder 78 rests in the slot 125, with one end for communicating directly or indirectly with an injection needle 85 through fluid pathways 122 and the other end for communicating directly or indirectly with a dispense indicator 101. The elongated spiral configuration allows the balloon or bladder 78 to have substantial volume for such quantity of injectable 79 as may be desired, while also contributing to the low profile configuration of the injection device 7. In other words, by utilizing a relatively long expandable member 78 with a large length to diameter ratio, very high pressures and volumes can be achieve with a minimum of forces required. Additionally the volume of the expandable member 78 can be changed by changing the filling length, without significantly altering the pressure/volume curves of the expandable member 78.

Figure 36:
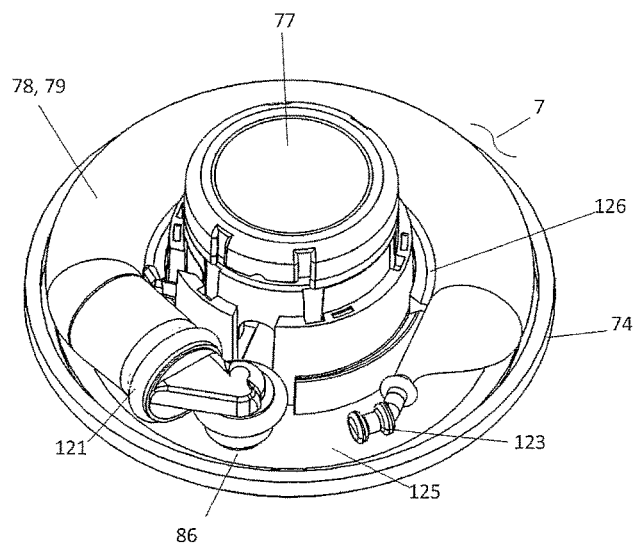
FIG. 36 is a perspective view of the injection device with the top housing removed in a filled state.
Figure 37:
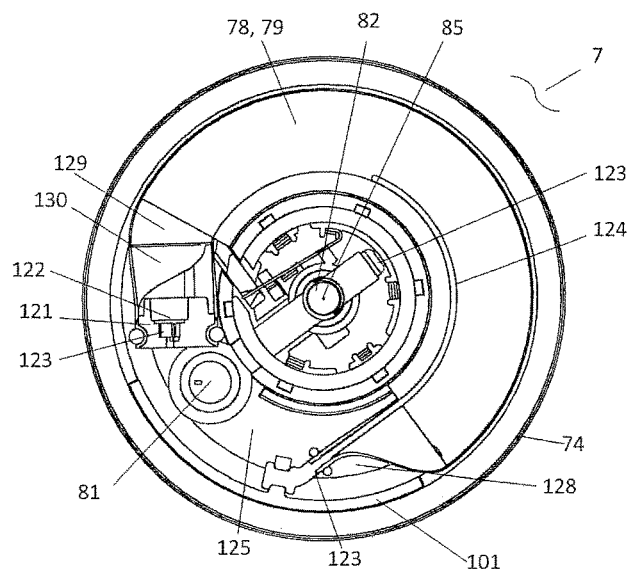
FIG. 37 is a top view of the injection device shown in FIG. 36.
Figure 38:
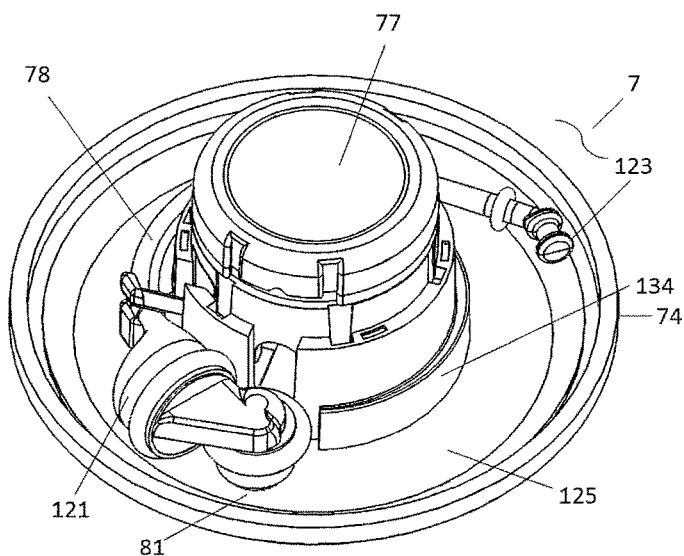
FIG. 38 is a perspective view of the injection device with the top housing removed in an empty state.
Figure 39:
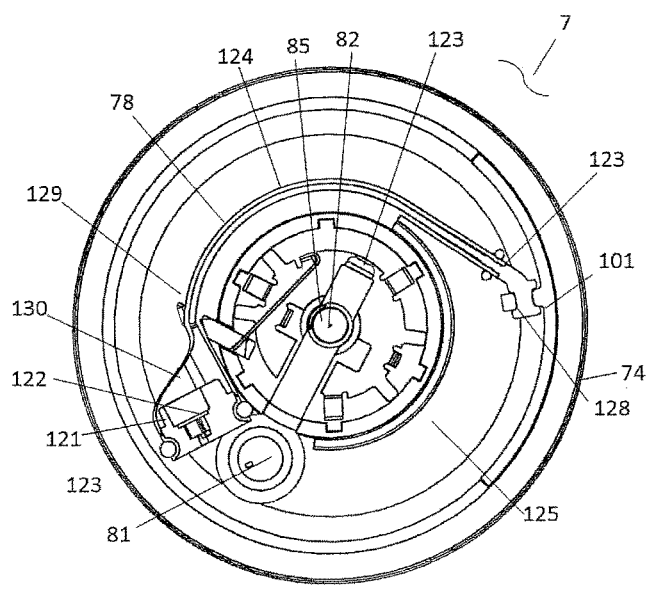
FIG. 39 is a top view of the injection device shown in FIG. 38.

Referring to FIGS. 36-39, one of the other aspects described in U.S. patent application No. 61/704,922, filed Sep. 24, 2012, that may be employed in the present subject matter is the use of an insert or plug or mandrel 124 within the expandable member 78 to pre-stress the expandable member 78 to a slightly expanded position when unfilled, so that when the expandable member 78 expels the injectable 79, it will contract or collapse to a condition where it is still stretched or stressed and continues to exert pressure on any fluid there within as shown in FIGS. 38 and 39. This better assures that all or substantially all of the injectable 79 is fully expelled from the injection device 7. The mandrel or shaft 124 could be a fluid filled expandable member if desired. This would allow for a variable size mandrel 124. Alternatively, the expandable member 78 could have a sufficiently small internal volume (small diameter) when unstressed so that virtually all the injectable 79 is expelled without the need for and internal mandrel or shaft 124. Additionally, the expandable member 78 could be flattened/stretched by 'wrapping' it around a surface within the injection device such as a cylindrical wall 134. The pre-stress created in the expandable member 78 would act to eliminate any residual fluid volume remaining within.

There are a number of different ways to cause an expandable member 78 to expand and/or contract in an arcuate manner as previously described. Referring back to FIG. 34, one way is to design the expandable member 78 with a thicker wall cross section 126 in one area around the circumference of the expandable member 78 that would cause the expandable member 78 to expand in a circular fashion. Alternatively, a separate element 126 could be affixed along the length of the expandable member 78 to effectively stiffen the expandable member 78 in that portion of the circumference that would cause the expandable member 78 to expand in an arcuate manner. Referring back to FIG. 36, another way is to use internal features such as slots or recesses 125 in the housing 74 of the injection device 7 to guide the expandable member 78 around a circular or spiral path. These features 125 could interact with the expandable member 78 in a number of ways, the simplest being the outer shape of the expandable member is constrained by a slot 125 in the housing 74 of the injection device 7. Friction between the expandable member 78 and the inner surfaces 125 of the housing 74 could be reduced by lubricating the outside surface of the expandable member 78, or by inserting the expandable member 78 within a low spring rate spring that would limit both the friction and outer diameter of the expandable member 78 while not constraining the length.

Referring to FIGS. 36-39, the elongated expandable member 78 may be preferably configured to expand along an arc with a predetermined tube diameter without the aid of walls or a guide within the injection device. Referring back to FIG. 34, looking at a cross-section of the elongated expandable member 78, a thicker wall area 126 in a small portion of the circumference of the expandable member 78 may be added to cause the elongated expandable member 78 to expand in an arc as previously described. The arcuate expandable member 78 grows in length due to increase in pressure and volume there within; the thicker section 126 deflects less than the thinner section.

Referring to FIG. 36, the arcuate expandable member 78 will expand in length in an arc shape as to orient its heavy wall thickness zone 126 or less deflecting zone to the inside of the circle. Increasing the wall thickness 126 of the expandable member 78 within the small zone 126 around the circumference will effectively continue to decrease the radius of the arc of the expandable member 78. The increase in wall thickness 126 may be achieved by molding or extruding it into the arcuate expandable member 78 or by bonding a strip of material to one side 126 of the expandable member to cause that portion of the wall 126 to lengthen at a slower rate, thereby causing the expandable member 78 to expand in an arc shape as previously discussed.

Referring to FIG. 37, the distal end of the expandable member 78 could be affixed an element such as an indicator 101, which is constrained to follow guide path within the inner surfaces 125 of the housing 74. Alternately, the expandable member 78 could be pre-stretched and flattened around a circular diameter inside the injection device 7 such as wall 134 so that there would be no change in expandable member length. Alternatively, a straight or curved mandrel 124 whose length is more than the unstressed expandable member could be used to stretch the expandable member into a circular shape within the injection device 7 prior to filling. Alternatively, the mandrel 124 could be used as a visual indicator to show the state of the injection device 7 and the progress of the injection. The mandrel 124 could be colored to allow it to be easily viewed through the housing.

Referring to FIGS. 36-39, the injectable 79 is injected into the expandable member 78 by the transfer apparatus and the expandable member 78 is expanded to a certain outer diameter controlled by the configuration of the inner surfaces 125 of the housing 74. In this way, the entire length of the expandable member 78 can be filled with a known volume of drug, and the outer diameter is known at each lengthwise location along the expandable member 78. It is desirable to have the expandable member 78 fill and empty along its length in a controlled way, from one end to the other to encourage the expandable member 78 to completely empty, and to allow the easy and accurate measurement of fluid 79 in the expandable member. To visually aid in determining how much fluid 79 is in the expandable member 78, graduated markings could be printed on the expandable member 78, like a syringe, to indicate the volume remaining in the expandable member 78. As previously described and referring to FIGS. 21-22, the expandable member 78 and housing 74 could be clear to allow the user to see the drug 74 and the volume remaining in the injection device 7. Alternatively, graduated markings 127 could be printed on the housing 74 to indicate the volume remaining in the expandable member 78.

Referring to FIGS. 36-39, in accordance with an aspect of this subject matter mentioned above, the injectable 79 is preferably expelled progressively from the distal end 128 of the elongated expandable member 78 toward the proximal end 129. The proximal end 129 of the expandable member is closest to the dispensing needle 82 or cannula. This allows the user to visually ascertain or approximate the injection status visually alone or with the aid of graduation markings 127 on the injection housing 74, the window 80 or the expandable member 78. Progressive expulsion may be achieved in a variety of ways. For example, the injectable 79 exits the expandable member 78 at the manifold 121 at the proximal exit port section 130 and is preferably located at the proximal end 129 of the elongated expandable member (e.g., balloon or bladder). The thickness of the wall of the expandable member 78 may be varied, uniformly or stepwise increased, along its length from the distal end 128 toward the proximal end 129. Due to restraint by the walls of the spiral channel 125 in which the expandable member 78 resides, the expandable member 78 would be inflated with injectable 79 to a substantially uniform diameter along its length. However, the thicker wall at the distal end 128 of the expandable member 78 would exert greater contraction force on the injectable 79 than the thinner wall at the proximal end 129 and thus collapse or contract in diameter first during expulsion of the injectable 79. The expandable member 78 would then collapse progressively from the distal end 128 toward the proximal end 129 as the wall of the expandable member 78 becomes thinner along its length in that direction. Because the thickness of the expandable member 78 preferably substantially uniformly increases from the proximal end 129 toward the distal or closed end 128, the contractive force of the expandable member 78 wall when expanded will increase substantially uniformly along the length of the elongated expandable member 78 from the proximal port end 129 to the distal or closed end 128. Thus, when the injectable 79 is expelled into the subject, the expandable member 78 will progressively collapse in diameter as well as shrink in length, which collapse in diameter and shrinkage in length is preferably viewable by the user as described above. The distal end 128 of the elongated expandable member may allow for the connection of a movable indicator component 101 in the injection device 7 which will follow the shrinkage in length of the elongated expandable member 78. This indicator 101 is preferably viewable by the user through the outer housing 74 and indicates the state of the injection device 7 and the progress of the injection. Alternatively, the expandable member 78 is configured with a constant wall thickness and could be prestressed in manufacturing to bias it to fill from the proximal end 129 to the distal end 128 and collapse or empty from the distal end 128 to the proximal end 129 in a progressive manner as previously discussed.

Referring to FIGS. 36-39, the elongated expandable member 78 of the injection device 7 may be configured to have a section 130 of the expandable member 7 adjacent to the proximal exit port end 130 that fills first and collapses last during filling and expulsion of the injectable 79 from the injection device 7. In other words, during filling of the injection device 7 by the transfer apparatus, it is advantageous to have the most proximal exit port section 130 of the expandable member 79 to fill with injectable first. Additionally, during dispense of the injectable 79 from the injection device 7, it is advantageous to have the last remaining volume of injectable 79 to be contained within the most proximal exit port section 130 the expandable member 79. There are several advantages to the abovementioned configuration. The proximal end section 130 of the expandable member 78 could have a thin wall that would cause it to remain inflated under a lower pressure than the rest of the expandable member 78. This would assure that the section 130 of the expandable member 78 would remain inflated until all injectable 79 had been expelled from the rest of the expandable member 78. As previously discussed, this section 130 may be directly coupled to an empty indicator to provide for full or empty indication. Additionally, as previously mentioned, this section 130 could be mechanically coupled to the empty indicator to allow for the automatic withdrawal of the button 77 and needle 82 upon complete expulsion of the injectable 79.

Referring to FIGS. 36-39, alternatively or in addition to varying the wall thickness 126 of the expandable member 78, an elongated internal mandrel or shaft 124 within the expandable member 78 may progressively (linearly or stepwise) decrease in cross-sectional size along the length of the expandable member 78 from proximal end (the exit port end) 129 toward the distal end (closed end) 128 of the expandable member 78. Additionally, the manifold 121 which allows for attachment of the expandable member 78 to the injection device 7 may also be configured with a large diameter section 130 at the proximal end 129 of the expandable member 78. A large diameter section 130 of the mandrel 124 or manifold 121 at the proximal end exit port 129 of the expandable member 78 insures that the expandable member 78 will fill with injectable 79 in this area 129 first. In other words, the expandable member 78 is being held at nearly a fill diameter at the proximal end exit port 129 by the large diameter section 130 of the mandrel 120 or manifold 121. As fluid 79 first starts to fill the expandable member 78, it reaches a fill diameter first in the large diameter section 130 then fills progressively along the length of the expandable member 78 from the proximal end 129 to the distal end 128 as previously discussed.

Referring to FIGS. 36-39, as previously discussed, during dispense of injectable 79 from the expandable member 78, the diameter of the expandable member 78 at its distal end continuously collapses in a progressive fashion (similar to deflating a long skinny balloon) from its distal 128 to proximal end 129 until all of the fluid is expelled from the expandable member 78. A large diameter section 130 of the mandrel 124 or manifold 121 at the proximal end exit port 129 of the expandable member 78 provides the same benefit (as previously described for filling) during dispense of the injectable 79. This large diameter section 130 insures that the last remaining fluid 79 in the expandable member 78 will be contained and dispensed from this area 130. As previously discussed, this section 130 may be directly coupled to an empty indicator to provide for full or empty indication as well as for the automatic withdrawal of the button 77 and needle 82 upon complete expulsion of the injectable 79.

Operation and Method

Figure 40:
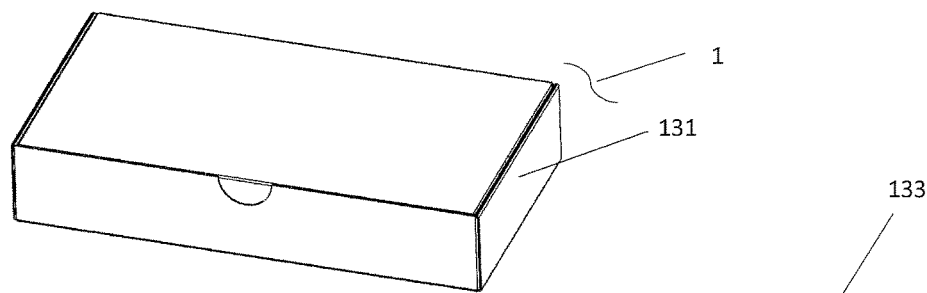
FIG. 40 is a perspective view of the single vial system in the packaging.
Figure 41:
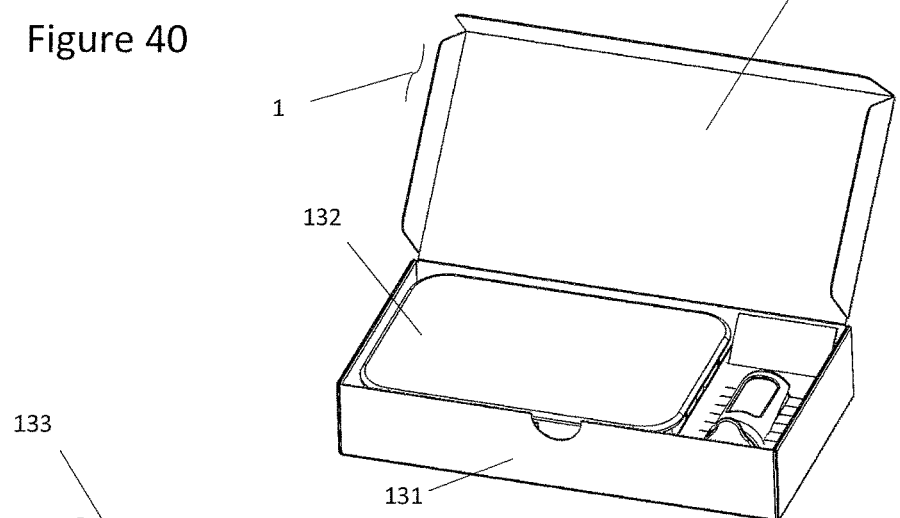
FIG. 41 is a perspective view of the single vial system in the packaging open.
Figure 42:
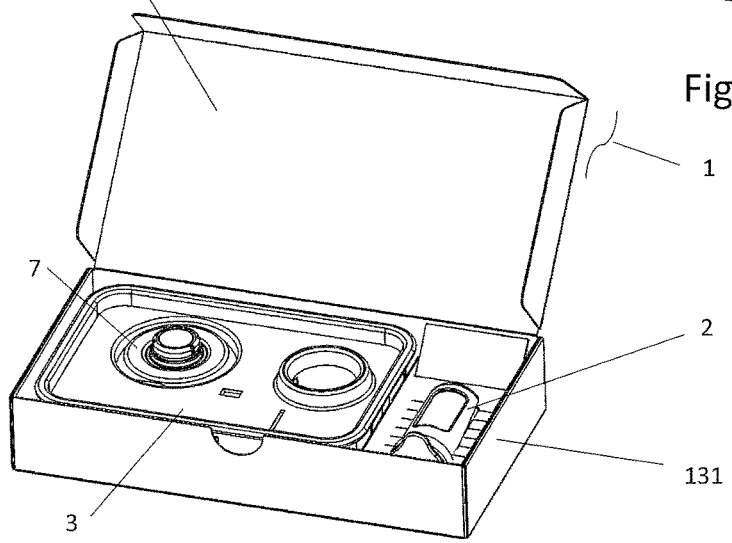
FIG. 42 is a perspective view of the single vial system in the packaging with the lid removed exposing the contents of the package.

Referring to FIGS. 40-42, the sterile injection device 7 is attached to the transfer apparatus 3 within a covered tray 132 and a separately packaged vial holder 2 with filled vial(s) is provided in a carton 131. The user places the carton 131 on a clean, flat surface. The user opens the lid 133 to the carton 131 to expose the transfer apparatus 3 and vial holder assembly 2. The user removes the cover 132 from the transfer apparatus tray 3 to expose the transfer apparatus 3 and injection device 7. The user is instructed to leave the transfer apparatus 3 in the carton 131 and only remove the injection device 7 when prompted.

Figure 43:
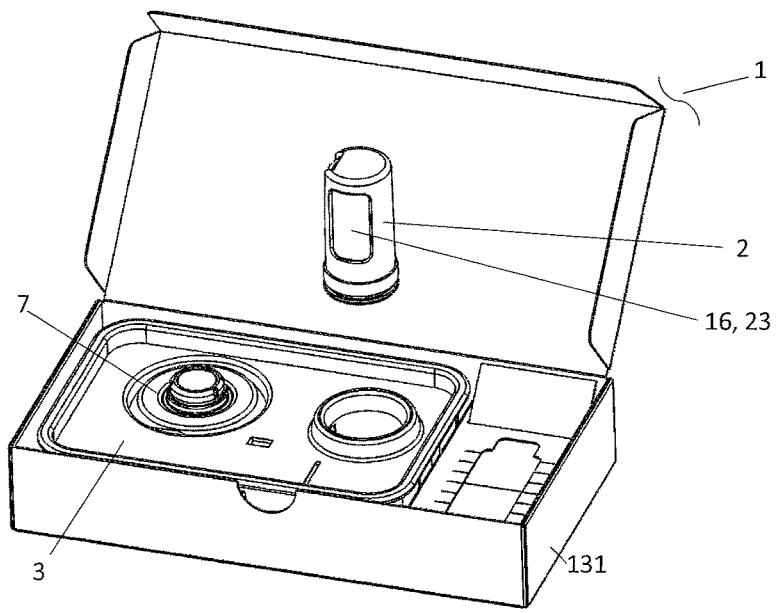
FIG. 43 is a perspective view of the single vial system with the vial holder removed from the package and the vial cap removed.
Figure 44:
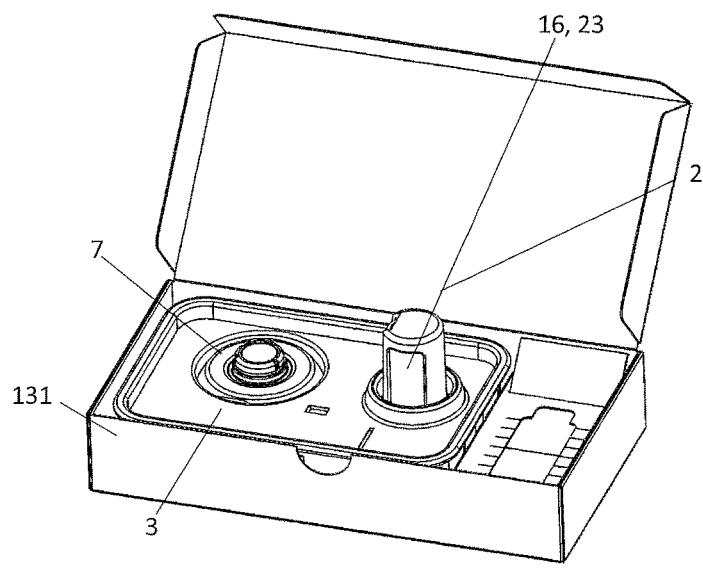
FIG. 44 is a perspective view of the single vial system with the vial holder fully inserted into the transfer apparatus.

Referring to FIG. 43-44, at the time of use, the user will remove the vial holder assembly 2 from the carton 131. The user will then remove the vial cap from the vial using the attached cap remover. The user will insert the vial holder 2 into the transfer apparatus 3. The user will push the vial holder 2 with attached vial 16 into the transfer apparatus 3 to actuate the system 1. This will do three things in the illustrated embodiment. First it will lock the vial holder 2 with attached vial 16 into a down position within the transfer apparatus 3. Then it will automatically initiate fluid communication between the contents 23 of the vial 16 and the transfer apparatus 3 by introducing an access member through the septum of the vial. Third it will initiate the mixing (if needed) and transfer sequence of the transfer apparatus 3. This sequence of events will occur automatically and require no additional input by the user to proceed.

Figure 45:
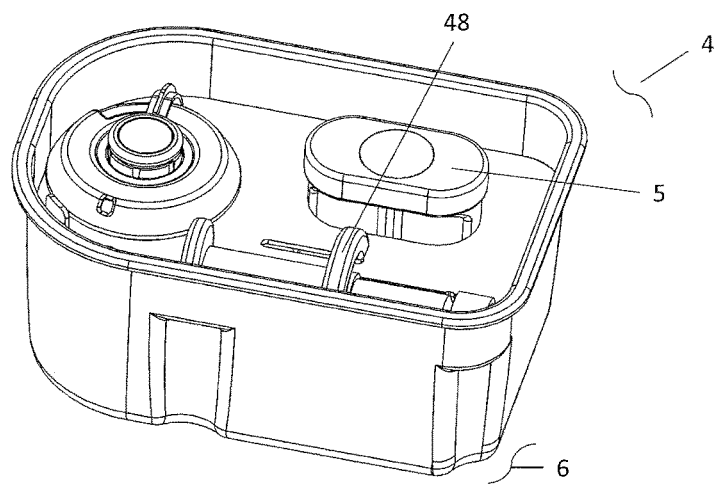
FIG. 45 is a perspective view of a dual vial system showing the vial holder installed.
Figure 46:
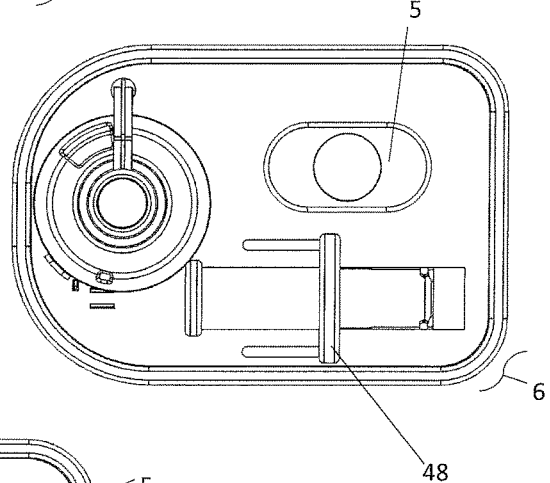
FIG. 46 is a top view of FIG. 45 showing the volume controller in a preset state.
Figure 47:
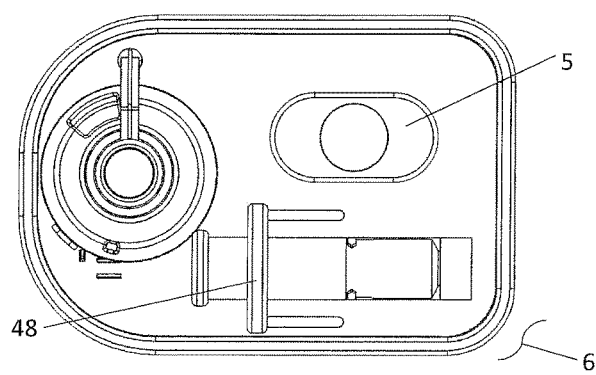
FIG. 47 is a top view of FIG. 45 showing the volume controller in a set state.

Referring to FIGS. 45-47, in a dual vial system 4 where mixing is required; the user may have the ability to adjust the delivery dose. A dose selector 48 is moved from an initial position shown in FIG. 46 to a final delivery volume position in FIG. 47. At this point, the vial holder 5 is free to depress by the user allow for the mixing and transfer to initiate. First, the diluent fluid is transferred from the diluent vial and introduced into the powdered lyophilized injectable vial. The fluid will be introduced into the powdered vial in such a way so that when the fluid is transferred from the vial, all the powder is removed as well. Mixing of the diluent and powder may occur completely in the powdered vial, or may be completed in the transfer apparatus. Static or dynamic mixing elements may be incorporated into the transfer apparatus or introduced into the powder vial by the transfer apparatus to allow for adequate mixing of the powered drug or other injectable and diluent. The mixing may take up to several minutes to complete. The mixing will be done in as gentle a way as possible to minimize bubbles/foaming and shear stresses in the mixture. The mixing also will be done in such a way to encourage the powder to be completely mixed, and no particles are present. In-line filters, valves or other means may be employed to remove particles or air. There may be an indicator on the transfer apparatus showing that mixing is progressing.

Referring to FIGS. 45-47, in a dual vial system 5, the reconstituted solution is mixed in the powdered vial or transfer apparatus 6, a set volume of solution prescribed by the manufacturer or set by the user is automatically transferred into the pressure dose chamber. This set volume is then automatically transferred to the injection device 7. The tubes, conduits valves and any other volume of the fluid path between the vials and transfer apparatus 6 will be minimized to encourage transfer of the maximum percentage of the drug to the injection device 7.

Figure 48:
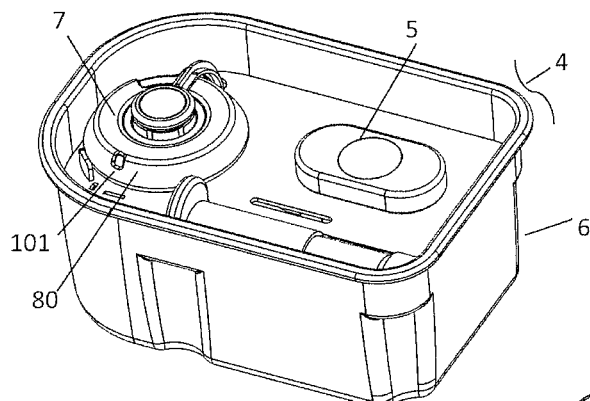
FIG. 48 is a perspective view of a dual vial system with the volume controller removed and the vial holder depressed into the transfer apparatus to start the mixing and transfer process.
Figure 49:
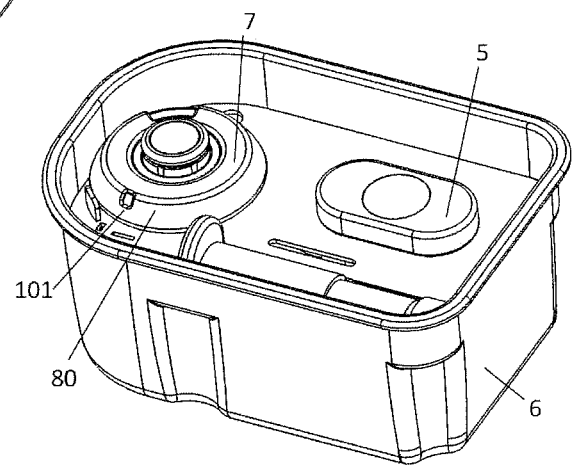
FIG. 49 is a perspective view of a dual vial system after completion of the mixing and transfer process, filling of the injection device and release of the injection device removal interlock.
Figure 50:
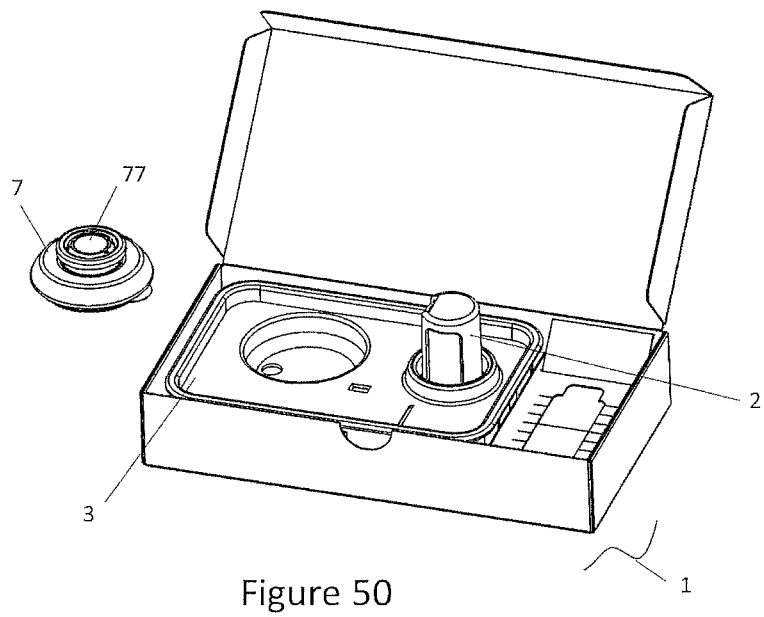
FIG. 50 is a perspective view of the single vial system with the injection device filled and removed from the package.

Referring to FIGS. 48-50, once the required dose volume has been delivered to the injection device 7, there is a clear area or other indicator 80, 101 in the injection device 7 to allow the user to view the mixed solution to verify complete mixing. Ideally, the user could view the entire drug volume within the injection device 7. There could also be an indicator 101, such a relative fill gage, to show that the correct dose had been delivered to the injection device 7. Completion of the mixing and transfer to the injection device 7 would then 'unlock' the injection device 7 and allow it to be removed from the transfer apparatus 3, 6 or injection device docking station. The injection device 7 may indicate to the user that it is in a ready state with the button 77 in the up or ready position and the indicator window 80, 101 showing the injection device is full.

Referring to FIG. 50, the user may disconnect the injection device 7 from the transfer apparatus 3 by twisting or pulling the injection device 7 off of the transfer apparatus 3. During removal of the injection device 7, an adhesive tape liner may be removed automatically exposing an adhesive surface on the bottom of the injection device that may be used to adhere the device to the patient's skin. Alternatively, the tape liner may have a tab that the user pulls to manually remove before adhering the device to the skin.

Figure 51:
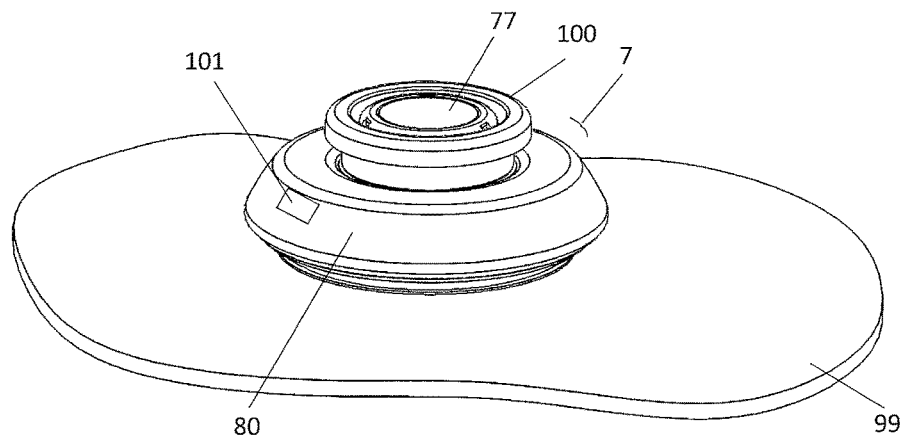
FIG. 51 is a perspective view of the injection device placed on the skin and the safety in place.

Referring to FIG. 51, the user attaches the injection device 7 to their skin 99. There may be an adhesive on the bottom of the injection device 7 that allows for adhesion to the skin 99 surface and hands-free operation. The adhesive may extend past the outline of the injection device to allow the user to firmly adhere the tape to the skin. Alternatively, the user may hold the injection device 7 against the skin 99 for the duration of the injection.

Figure 52:
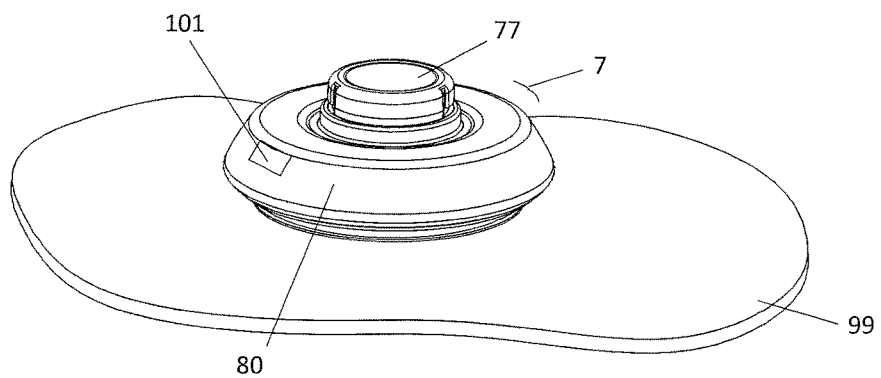
FIG. 52 is a perspective view of the injection device placed on the skin and the safety removed.
Figure 53:
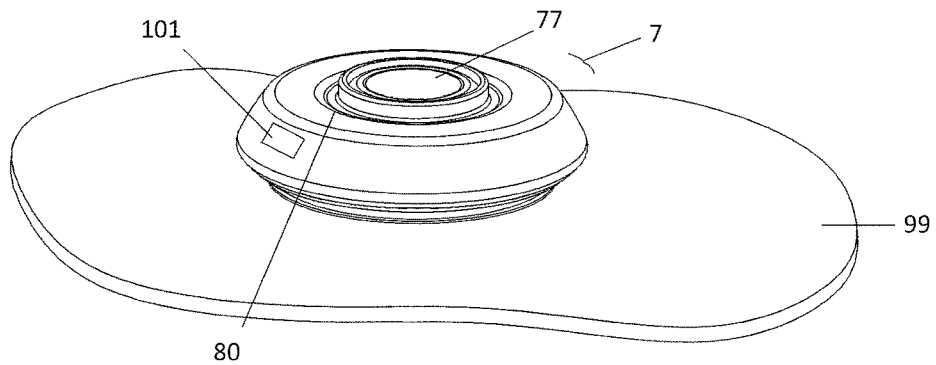
FIG. 53 is a perspective view of the injection device placed on the skin and the button depressed to fire start the injection.

Referring to FIGS. 51-53, the user removes the safety 100 and depresses the button 77 on the injection device 7 to start the injection. Once the button 77 on the injection device 7 is fully depressed, it is locked into place and the needle will be fully inserted into the patient and the injection device 7 will begin dispensing the injectable drug. The injection device 7 may alert the user that injection of the drug has started. This alert could be in the form of visual indictors, audible sounds, mechanical movements or a combination. The time of the injection could be in a range of a few seconds to several hours. The injection device 7 may indicate to the user that it is dispensing with the button 77 locked in the down position and indicator window 101 showing the injection device 7 is less than full. The injection device 7 preferably has a clear section 80 that allows the user to easily determine the amount of drug remaining in the injection device 7.

Figure 54:
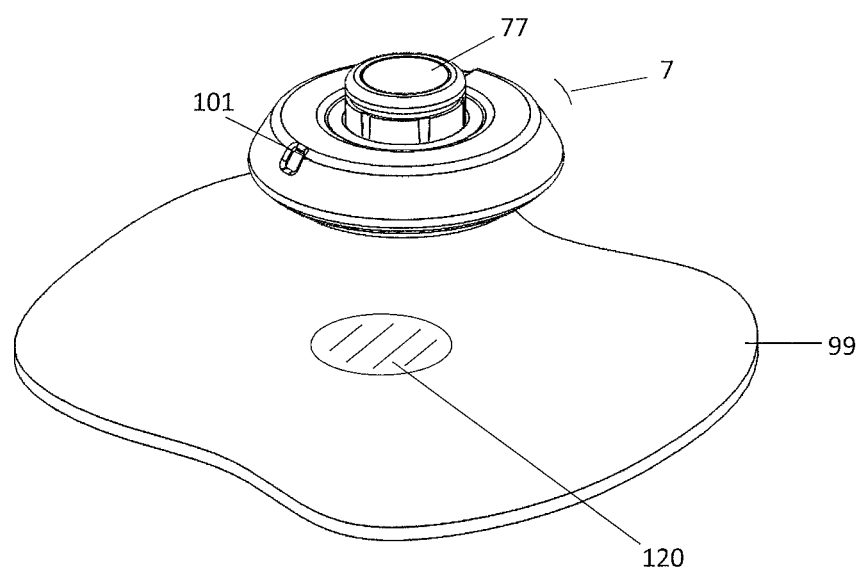
FIG. 54 is a perspective view of the injection device removed from the skin after the injection with the button in a locked up position and a bandage remaining on the skin.

Referring to FIG. 54, the user will be alerted when the injection of the drug is completed. This alert could be in the form of visual indicators, audible sounds, mechanical movements or a combination. The injection device 7 may indicate to the user that it is has completed dispensing with the button 77 moving to a locked up position with tactile and audible sounds and indicator window 101 showing the injection device is empty. At the end of the dispense, the needle will automatically retract into a locked position within the injection device 7.

Referring to FIG. 54, upon removal of the injection device 7 from the skin 99, a bandage 120 could release from the injection device 7 and remain on the skin surface 99. Upon removal from the skin 99, the injection device 7 will preferably be locked out, preventing non-destructive access to the needle or reuse of the injection device 7. The injection device 7 may indicate to the user that the full dose has been delivered. This indication could be in the form of a visual indictor, audible sound, mechanical movement or a combination.

In accordance with further aspects of the present subject matter, when administering an injection with a syringe and needle that is meant to be infused under the skin, it is desirable to know if the needle is properly placed within the skin or improperly placed within a blood vessel. It is common for a user performing an intradermal (ID), subcutaneous (SC) or intramuscular (IM) injection to aspirate the syringe by pulling back on the plunger to create a pressure drop within the syringe to see if any visible blood comes up the needle into the syringe. If blood is visualized, this means the tip of the needle is in a blood vessel. A number of injectable drugs meant for infusion under the skin specifically indicate not to inject into a blood vessel. Blood aspiration using a syringe and needle is a common technique and can be performed by anyone with adequate training. However, as more drugs are being presented in automatic injection devices, the ability to manual aspirate these types of systems does not exist. Once an injection device is placed on the skin and the needle is fired, there is no way for the user to know if the needle is properly placed within the skin or improperly placed within a blood vessel. Accordingly, there exists a need for a blood aspiration device and method within an automatic injection device.

Figure 55:
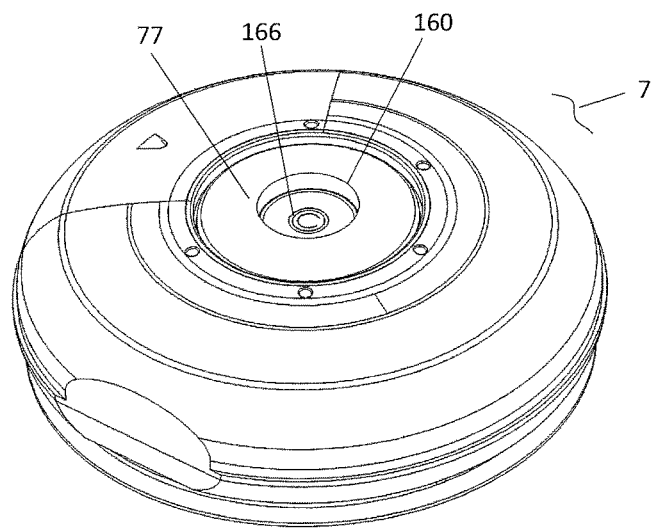
FIG. 55 is a perspective view of injection device embodying the present subject matter.
Figure 56:
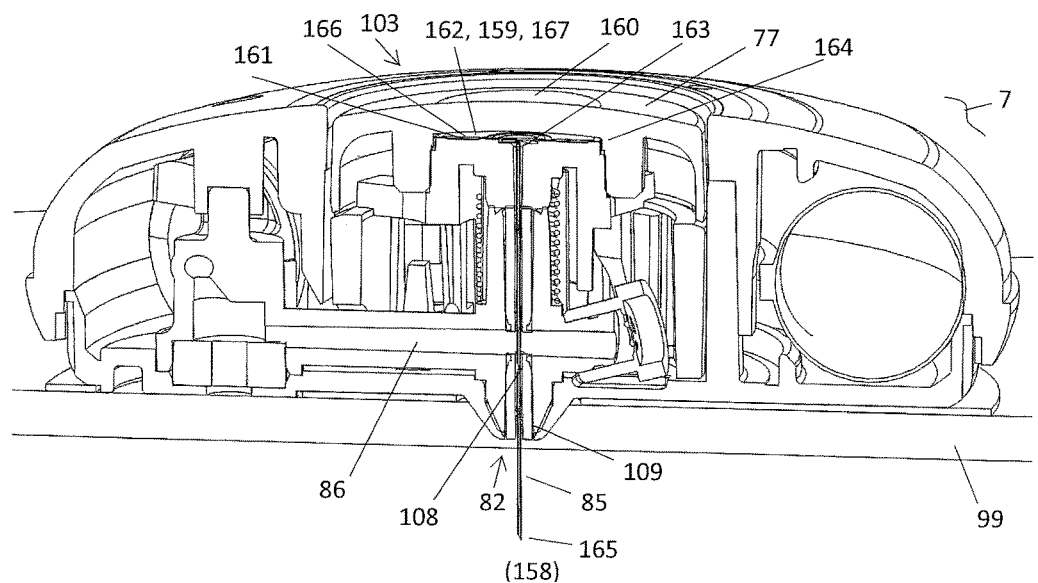
FIG. 56 is a cross-section of FIG. 55 showing the injection device with the button in the first position.

Referring to FIGS. 55-56, the injection device 7 may have a needle 85 with a side-hole 108 in operative engagement with the button 77 slidable within a septum 109 advancing into the skin 99. The button 77 may have a viewing window 160 on the button top 103 that is in fluid communication with the proximal end 161 of the needle 85. The button top 103 may include a cavity 162 for blood 159 to accumulate and be seen through the button window 160 by a user. The cavity 162 may include a center hole 163 that allows fluid communication with the proximal end 161 of the needle 85 via needle lumen 165. The outer walls 164 of the cavity 162 are formed by the button top 103. Additionally, a portion of the outer walls 164 may include a hydrophobic filter 166. In this configuration, the proximal end 161 of the needle 85 is at atmospheric pressure. If fluid 14 or blood 159 travel up the internal lumen 165 of the needle 85, it exits the proximal end 161 of the needle 85 and fills the cavity 162. The air 167 in the cavity 162 is easily displaced through the hydrophobic filter 166 until all of the air 167 has been displaced from the cavity 162 and it is full of fluid 14 or blood 159. At this point, the flow of fluid 14 or blood 159 stops as the fluid 14 or blood 159 cannot penetrate the hydrophobic filter 166 and can be easily viewed through the window 160 of the button top 103 by the user thus providing a method for determining if the injection device 7 needle 85 is in a blood vessel 158.

Figure 57:
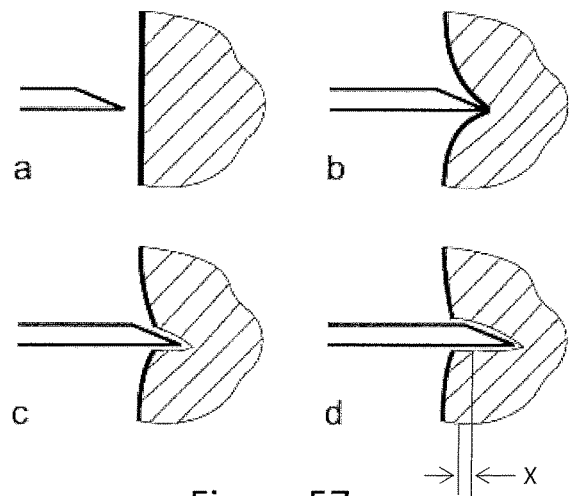
FIG. 57 is an illustration (Van Gerwen, D. J. *Needle-Tissue Interaction by Experiment*. Ph.D. Thesis, Delft University of Technology, 2013. ISBN 978-94-6186-238-9, pg. 11) showing four stages of needle penetration into tissue including a.) no contact, b.) boundary displacement, c.) tip insertion and d.) shaft insertion.

Referring to FIG. 57, needle insertion into tissue can be generally divided into four stages. These include no contact, boundary displacement, tip insertion and shaft insertion. During boundary displacement, the tissue boundary in the contact area deflects under the influence of the load applied by the needle tip, but the needle tip does not penetrate the tissue. The boundary of the skin follows the tip of the needle up to a maximum boundary displacement point in the contact area as the needle tip starts to penetrate the skin. After the needle tip penetrates the skin, the shaft is inserted into the tissue. Even after tip and shaft insertion, the boundary of the skin surface in the contact area does not return to its original no contact state but remains displaced by a distance x. The amount of boundary displacement x is a function of several parameters including but not limited to needle diameter, needle tip geometry, needle shaft friction, needle insertion speed and physical skin properties. Boundary displacement x of the skin in the contact area is characterized in needle-based injection devices because it effects how much of the needle penetrates the skin and therefore reduces the actual needle penetration depth by the amount of boundary displacement x. If the boundary displacement x could be intentionally induced by stretching or preloading such as pushing the skin out at the contact site prior to needle tip insertion, there would be no additional boundary displacement by the needle tip or shaft during insertion and the needle tip depth could be predictably defined. The advantage of this intentional displacement is the amount of needle penetration into tissue would not be affected by variations in the boundary displacement x. Without intentionally inducing boundary displacement at the skin surface prior to needle tip insertion, the actual needle penetration depth into the skin is not specifically known because some of the needle length (depending on the abovementioned parameters) is outside the skin due to the naturally occurring boundary displacement x shown in FIG. 57. On the other hand, if the maximum boundary displacement could be induced at the contact site, the actual needle penetration depth would not change with the variations in the abovementioned parameters including needle diameter, needle tip geometry, needle shaft friction, needle insertion speed and physical skin properties.

Figure 58:
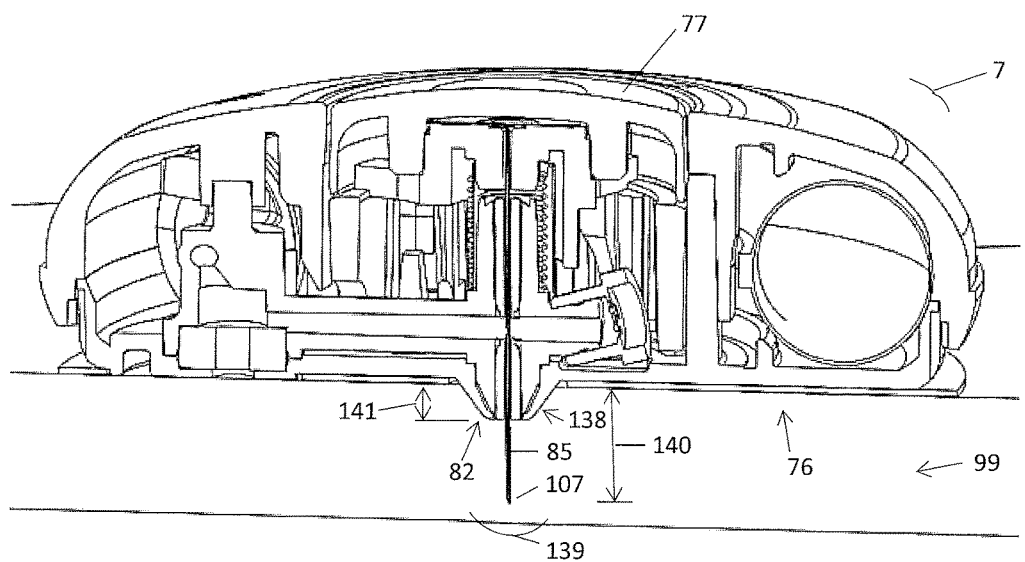
FIG. 58 is a cross-section of FIG. 55 showing an injection device with the button in a second position or dispense position.
Figure 103:
FIG. 103 is an ultrasound image showing the subcutaneous depth of a bolus injection employing a commercial infusion pump with a 9 mm subcutaneous needle depth.
Figure 104:
FIG. 104 is an ultrasound image showing the depth of a bolus injection employing injection device 7, similar to FIG. 56, with a 5 mm needle depth.
Figure 105:
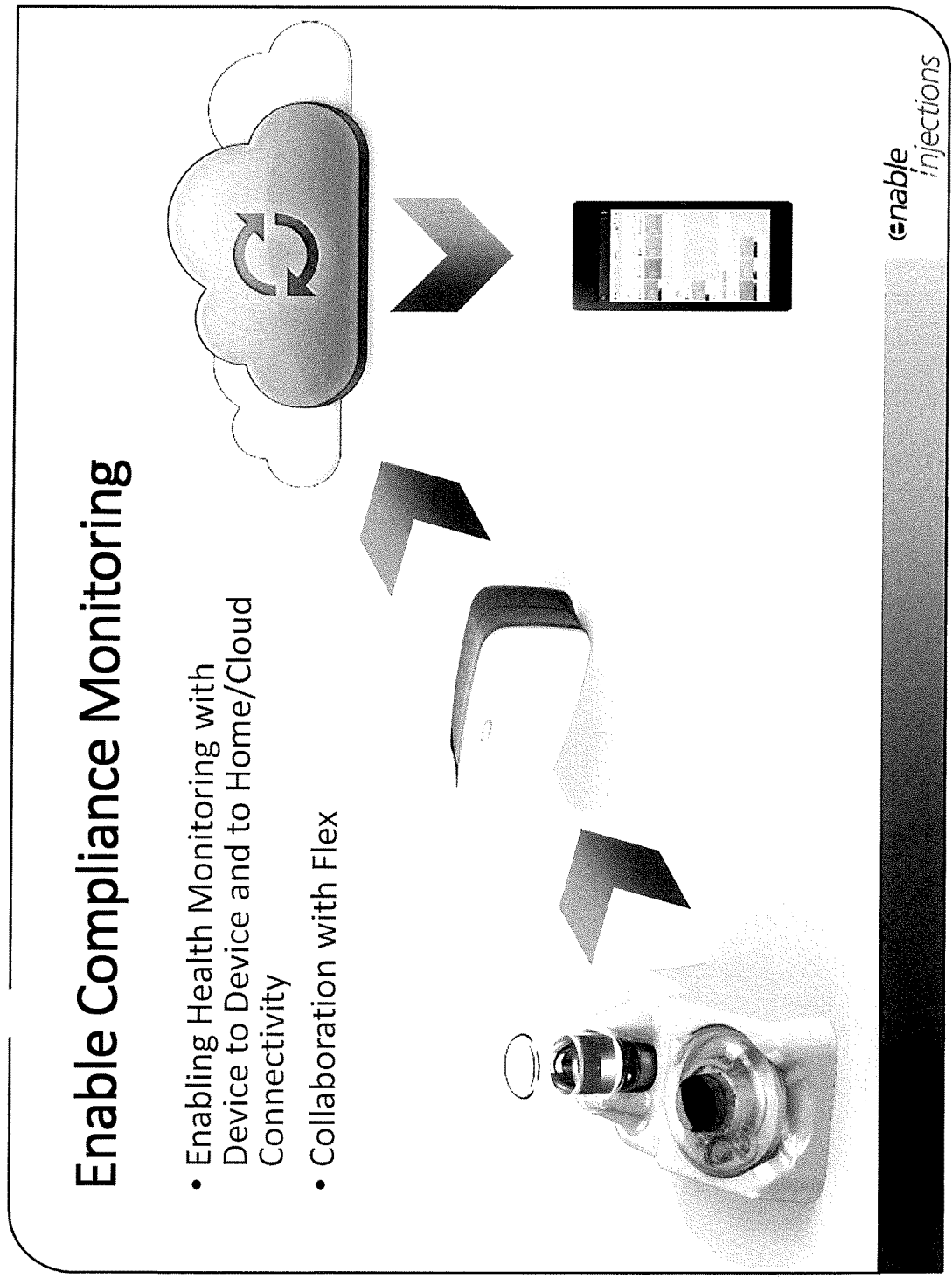
FIG. 105 depicts a compliance monitoring system.
Figure 106:
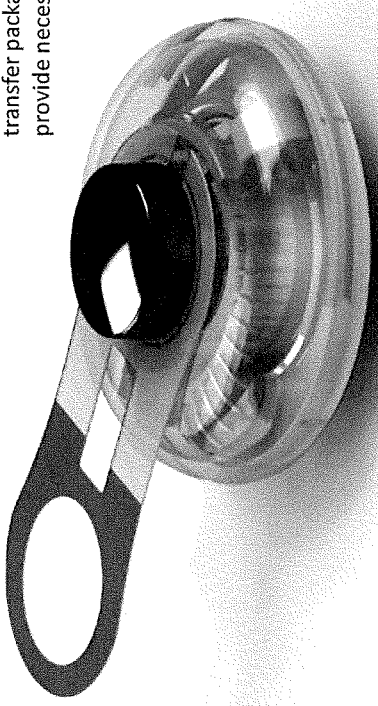
FIG. 106 further depicts a compliance monitoring system.
Figure 107:
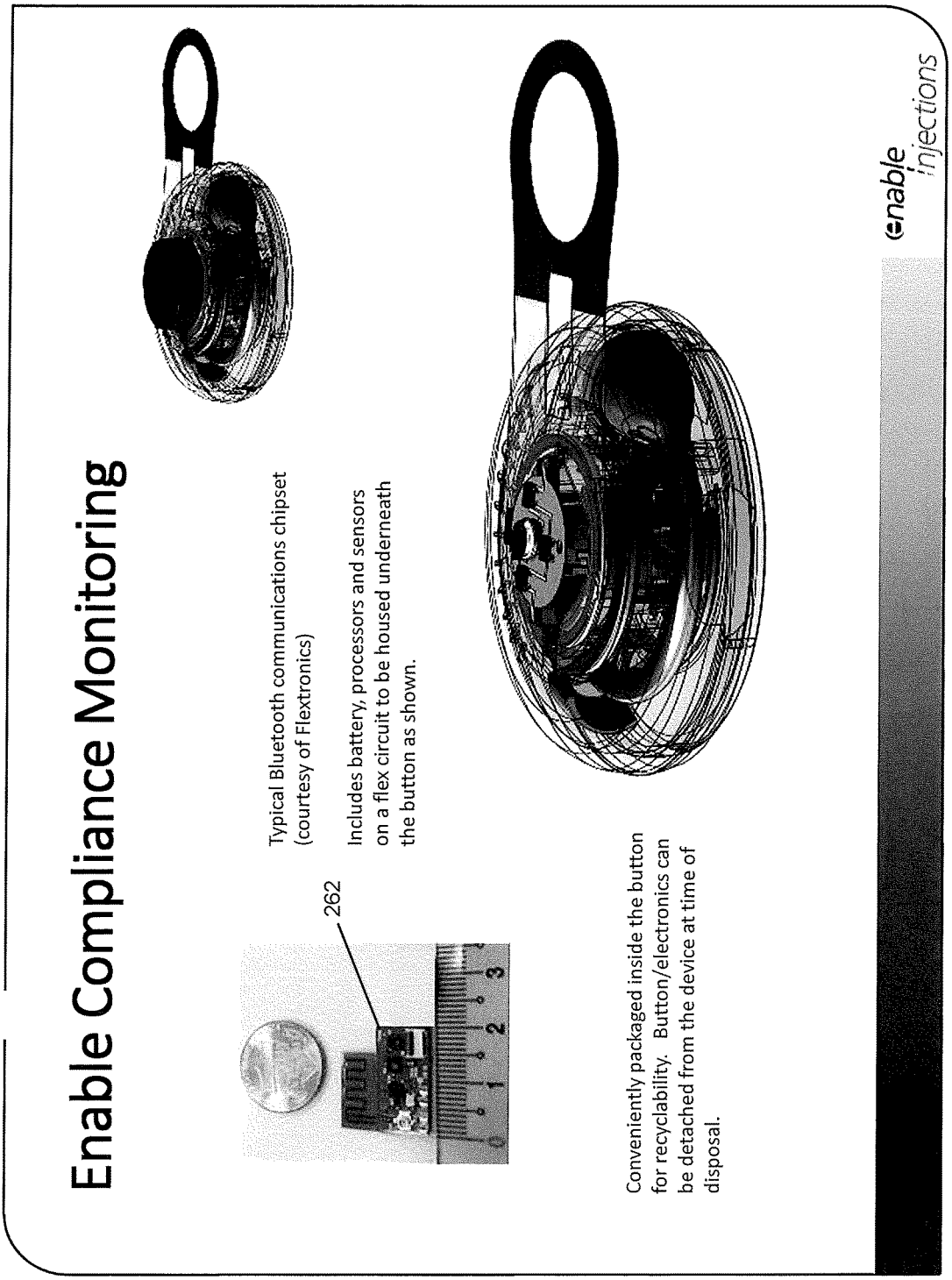
FIG. 107 shows additional aspects of a compliance monitoring with an injection device of the type described herein.

Referring to FIG. 58, the injection device 7 may have a skin boundary displacement extension or structure, such as an underside surface 76 that includes an extension 138 at or around the dispense port 82 or as part of the dispense port 82. The extension extends substantially normal to plane of the tissue at the point of needle insertion. When the injection device 7 is attached to the skin 99, the extension 138 will protrude against the skin 99 surface resulting in displacement or compression of the skin 99 in this contact area 139. The compression of the skin helps to reduce or eliminate "tenting" of the tissue surface upon needle insertion. In other words, by "preloading" the tissue by compressing it, the extension 138 serves to eliminate further tissue defection or tenting, or results in more reproducible and lesser amount of skin surface deflection or tenting. During actuation of the button 77 from a pre-fire state to first position, the needle 85 advances out of the injection device 7 through the dispense port 82 and/or extension 138 into the skin 99 to start the dispense of drug. For the reasons described above, as the needle 85 advances out of the injection device 7, the tip of the needle 107 does not produce additional boundary displacement 141 (already intentionally induced by the extension 138) in the skin 99 at the contact area 139. Thus the actual needle penetration depth 140 into the skin 99 is better characterized and controlled. Also, the extension, through which the needle passes, compresses the tissue immediately around the needle, which has several advantages. During the injection, the compression of the tissue by the extension 138 in the contact area 139 increases the local density of tissue thus creating a higher pressure zone compared to the surrounding adjacent tissue 99. As injectable enters the skin 99, the fluid will migrate from this high pressure zone 139 to lower pressures areas in the skin 99 which helps to prevent injected fluid or drug from flowing or migrating into the immediate area around the needle/skin puncture site and acts to reduce or minimize fluid leakage (backflow) and/or bleeding from the puncture site. This higher pressure zone also effectively provides the benefit of a much longer injection needle. Experimental data confirms this. In an ultrasound evaluation comparing the subcutaneous deposition depth of a 10 mL fluid bolus (saline) using the injection device 7 with a 5 mm needle depth and an off-the-shelf infusion pump (Freedom 60, RMS) with a butterfly needle extension set (9 mm needle depth), results show that the subcutaneous depth of the 10 mL bolus, post injection was equivalent between the injection device 7 with a 5 mm needle length and the pump with a 9 mm needle length. In all results, bolus position was characterized by distance (Zd) from the skin surface to top edge of bolus. FIG. 103 shows the top edge of the 10 mL subcutaneous bolus using the pump with 9 mm needle length. The Zd distance was measured at 0.44 cm. FIG. 104 shows the top edge of the 10 mL subcutaneous bolus using the injection device 7 with a 5 mm needle length. The Zd distance was measured at 0.42 cm. Thus, a similar depth of the bolus is provided with a needle depth (5 mm) and the tissue displacement structure that is more than 40% shorter than the other tested needle (9 mm) without a tissue displacement structure.

Another advantage of the extension 138 is compression of the tissue in the contact area 139 after the injection has completed. In the post-fired state, the button 77 has popped up alerting the user that the injection device 7 has completed. The needle 85 is fully retracted out of the puncture hole in the skin 99. The dwell time between when the injection device 7 has completed dispense and is removed by the user can be several minutes or more, depending on the environment in which the user is in at the time of completion. For the same reasons described earlier, the compression of the tissue by the extension 138 in the contact area 139 increases the local density of tissue thus creating a higher pressure zone compared to the surrounding adjacent tissue 99. Similar to how a nurse may apply pressure to an injection site with their thumb after injection, this pressure helps close the puncture hole and prevents injected fluid or drug from flowing back up the injection site and acts to reduce or minimize fluid leakage and/or bleeding from the puncture site.

Figure 59:
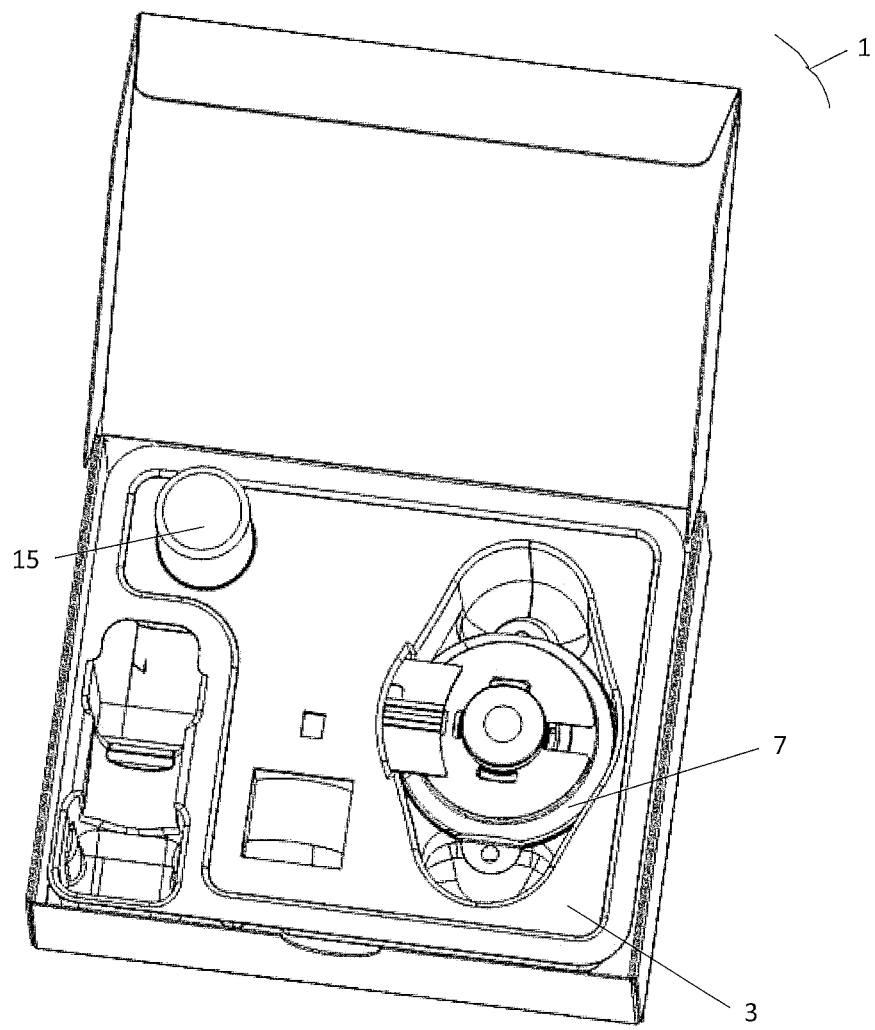
FIG. 59 is a perspective view of a single vial transfer system with the drug vial and injection device installed embodying the present subject matter.
Figure 60:
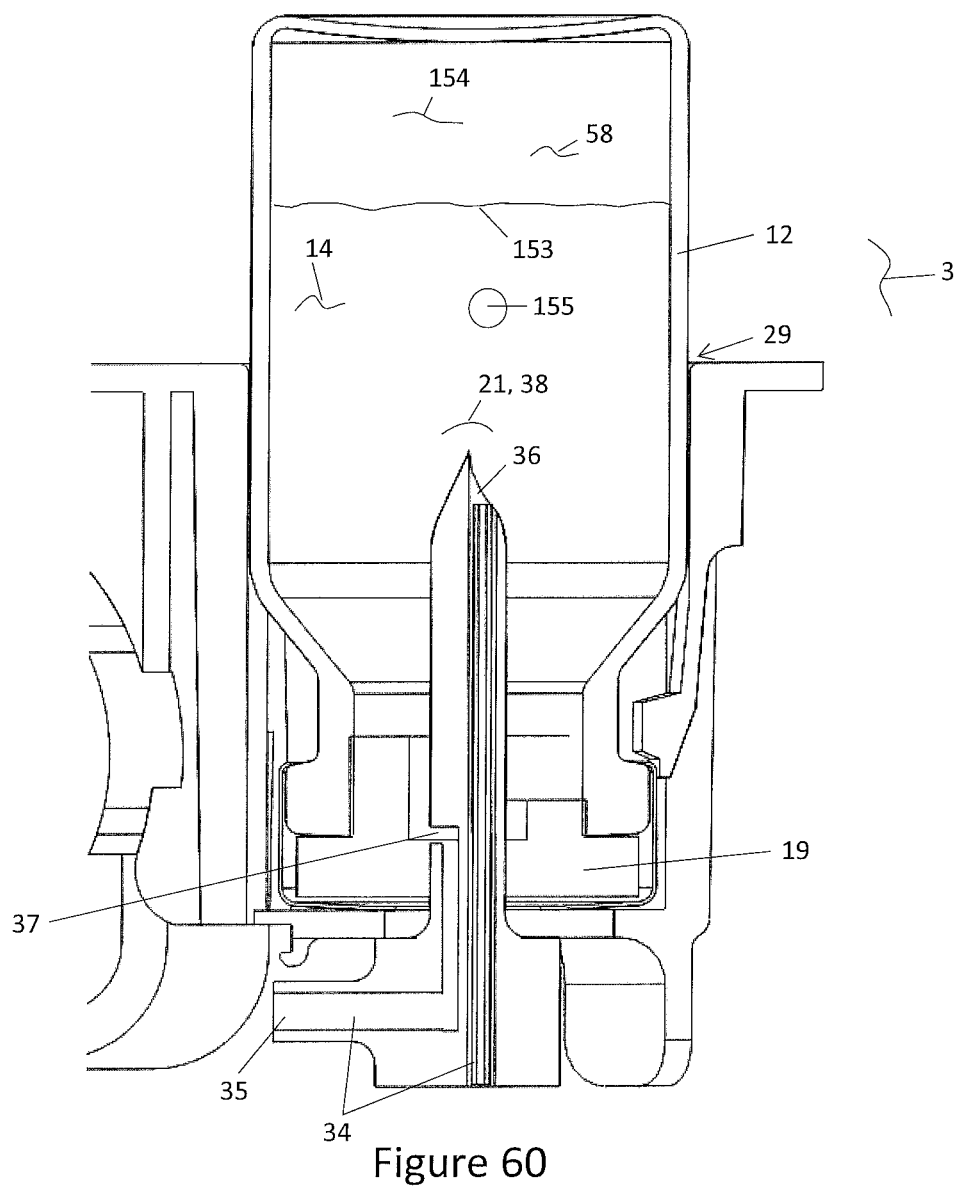
FIG. 60 is a cross-section of FIG. 59 with depicting an aspect of the vial holder area showing the drug vial, a vial access member and an extension member in the down position.

Referring to FIG. 60, the vial access member 21 of the transfer apparatus 3 maybe comprised of multiple lumens, such as multi-lumen tubes 34 to communicate with the internal fluid pathways 35 of the transfer apparatus 3. The vial access member 21 preferably comprises one inlet tube 36 allowing air or fluid to enter the vial 12 and one outlet tube 37 allowing for air or fluid to exit the vial 12. The lumen openings 38 in the vial access member 21 can be oriented so the inlet tube opening 36 is above the output tube opening 37 when the vial is inverted and attached as illustrated, for example, in FIG. 59. This orientation allows for introduction of air or liquid through the upper inlet tube 36 and output of the vial contents 14 through the lower output tube 37. Further, the outlet opening 37 may be positioned near the lower end bottom of the inverted vial 12, adjacent to the septum 19 to encourage the entire contents 14 of the vial 12 to enter the outlet port 37 and be removed from the vial 12. Once the vial 12 is installed in the vial holder docking area 29 in the transfer apparatus 3, the vial access member 21 is able to access the contents 14 of the vial 12. When the transfer apparatus 3 begins to withdraw the contents 14 from the vial 12 through the outlet tube 37, a pressure drop 154 occurs in the vial 12. This pressure drop 154 causes displacement air 58 to be drawn into the vial 12 through the inlet opening 37 of the vial access member 21 to replace the fluid 14 that is being withdrawn. In some cases depending on the amount of injectable 14 in the vial 12, the liquid level 153 in the vial 12 may be above the vial access member 21 and specifically above inlet tube opening 37. When air 58 is drawn into the vial 12 through the inlet opening 37, it creates a bubble 155 in the fluid 14. Buoyancy causes the bubble 155 to migrate to the top of the vial 12 with the existing air 58. In some injectables 14, it is undesirable to introduce air bubbles 155 into the solution. This causes more bubbling, frothing and or foaming within the fluid 14.

Figure 61:
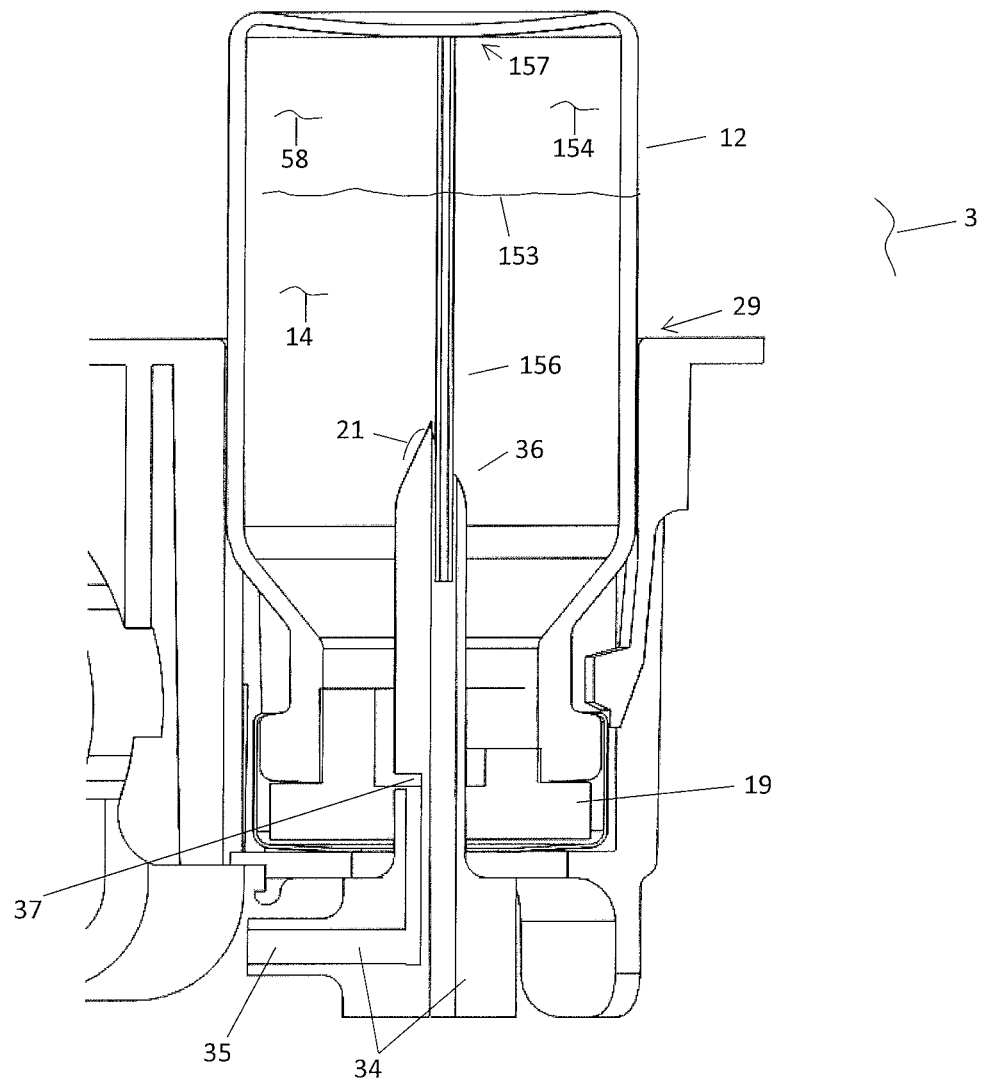
FIG. 61 is a cross-section of FIG. 59 depicting an aspect of the vial holder area showing the drug vial, a vial access member and an extension member in the up position.

Referring to FIG. 61, an extension member 156 could be slideably moveable within the inlet opening 36 of the vial access member 21. The outer diameter of the extension member 156 may be close fitting to the inner diameter of the inlet opening 36. The extension member 156 may have an inner diameter that allows air 58 to pass through it. When air 58 is drawn into the vial 12 through the inlet vent opening 36 due to the pressure drop 154 in the vial 12, the air 58 first pushes the extension member 156 like a piston within the inlet opening 36. The extension member 156 is sufficiently long as to not come out of the inlet opening 36. The extension member 156 continues to slide through the inlet opening 36 until the end of the extension member 156 stops at the top 157 of the vial 12 well above the liquid level in the vial 153. The top of the inverted vial 12 acts as a stop to the extension member 156. The tip of the extension member 156 may be tapered as to not block flow through its inner diameter when in contact with the top of the inverted vial 12. Air 58 continues to travel through the inner diameter of the extension member 156 until all of the fluid 14 in the vial 12 has been withdrawn from the vial 12 through the outlet tube 37. As previously mentioned, the outer diameter of the extension member 156 is close fitting to the inlet opening 36 inner diameter as to not allow air to leak between this interface. The extension member 156 insures that no air 58 is introduced into the liquid 14 within the vial 12 causing bubbles 155.

Figure 62:
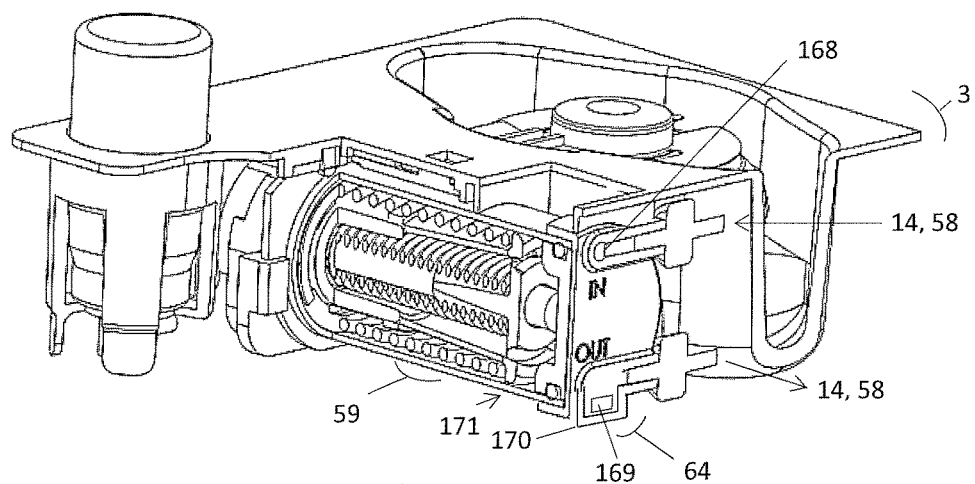
FIG. 62 is a cross-section of FIG. 59 with the box and tray removed and depicting an aspect of the pressure chamber and fluid passageways.

Referring to FIG. 62, the pressure chamber 59 may be configured with an inlet port 168 used to bring fluid 14 and air 58 into the chamber. Additionally, the pressure chamber 59 may be configured with an outlet port 64 used to expel fluid 14 and/or air 58 out of the chamber 59. These ports 168, 64 may be positioned off-center of the pressure chamber 59 to help control the sequence of liquid 14 and air 58 introduction into and/or expulsion from the pressure chamber 59. As previously mentioned, the outlet port 64 of the pressure chamber 59 may be oriented below the inlet port, during the process of expelling the liquid 14 from the pressure chamber 59, all of the liquid 14 is expelled first then the remaining air 58 is expelled last any air in the chamber 59 would be oriented to the top of the pressure chamber 59. Additionally, as shown in FIG. 62, the exit port profile 169 may be configured in a non-circular shape to further encourage the entire liquid contents 14 of the pressure chamber 59 to enter the outlet port 64 and be removed from the pressure chamber 59 prior to removal of air 58 from the pressure chamber 59. Additionally, as shown in FIG. 62, a portion 170 of the outlet port 64 may be positioned below the surface 171 of the pressure chamber 59. This may act as a trap to further encourage the entire liquid contents 14 of the pressure chamber 59 to enter the outlet port 64 and be removed from the pressure chamber 59 prior to removal of air 58 from the pressure chamber 59.

Figure 63:
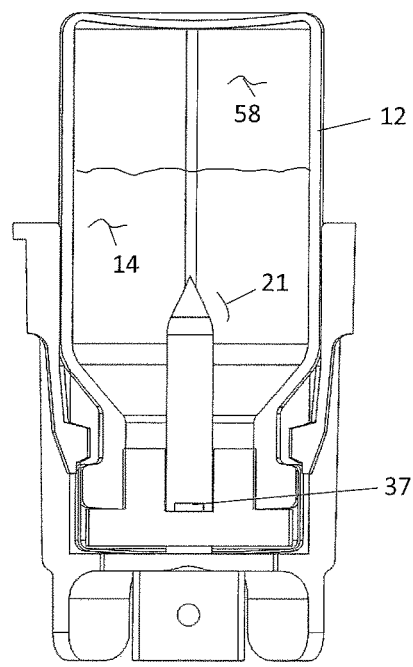
FIG. 63 is a cross-section of FIG. 59 depicting an aspect of the vial holder area showing the drug vial, the vial access member and outlet opening.

Referring to FIG. 63, when liquid 14 is removed from a vial 12 using a vial access member 21, only fluid 14 through the outlet opening 37 is removed until the liquid level 153 drops to the top of the outlet opening 137. At this point, a mixture of liquid 14 and air 58 will be removed. Referring to FIG. 63, the vial access member 21 may additionally have an outlet opening 37 configured in a non-circular shape such that the opening height is reduced and the opening width is increased to further allow for more liquid content 14 of the vial 12 to enter the outlet port 37 and be removed from the vial 12 prior to removal of air 58 from the vial 12.

Figure 64:
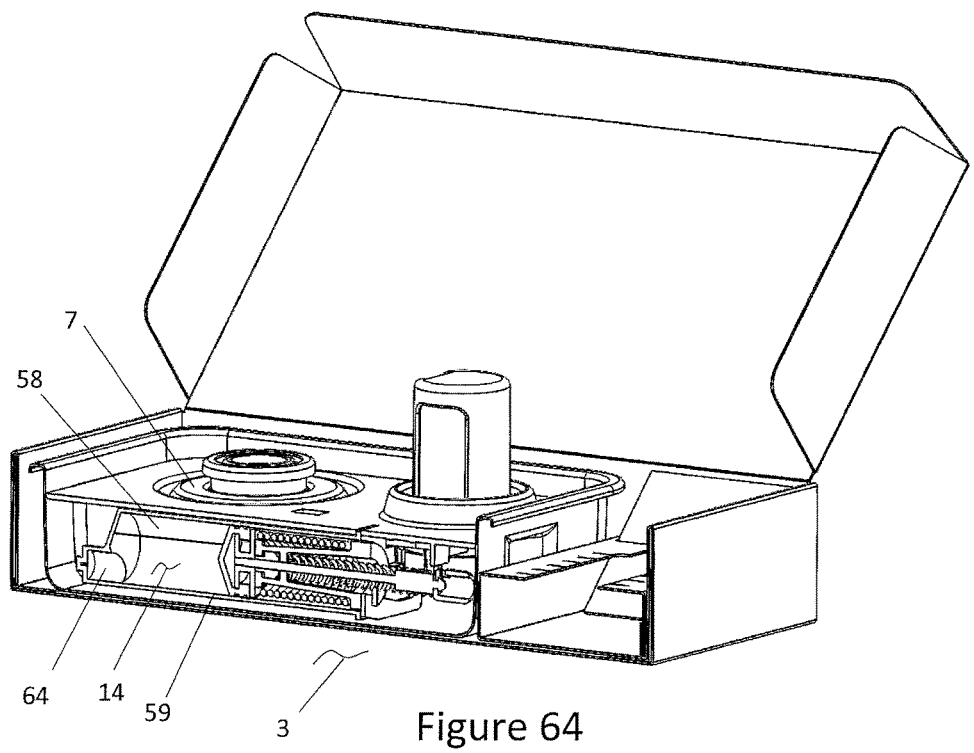
FIG. 64 is a cross-section of a single-vial system including the single vial holder, transfer apparatus and injection device system.
Figure 65:
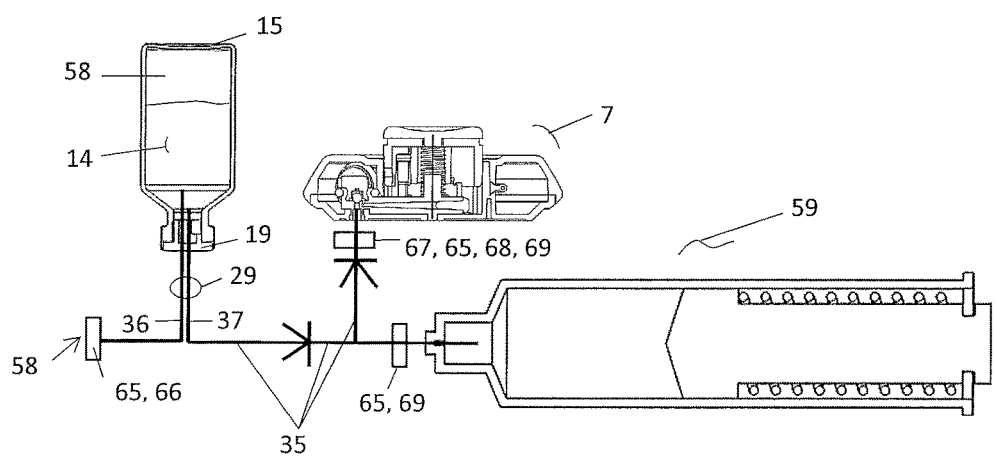
FIG. 65 is a schematic of an alternative embodiment of the single vial transfer system in FIG. 64 with a drug vial, a transfer apparatus with a first variable pressure chamber, an injection device including the fluid pathways with check valves and flow restrictors.

Referring to FIGS. 64 and 65, the combination of hydrophobic 68 and hydrophilic 69 filters in the fluid pathway 35 between the vial 15 and the injection device 7 may preferably allow for filtering of drug 14 and removal of air 58 during the transfer process. These filters may be separate components or combined into one component. Each filter may be constructed from different materials including but not limited to Mixed Cellulose Ester (MCE), Polyvinylidene Difluoride (PVDF), Polytetrafluoroethylene (PTFE), Nylon and polyethersulfone (PES). Each filter may have a range of pore sizes from 0.22 to 3 micron. Each filter may have a coating to make it hydrophilic or hydrophobic.

When administering an injection that is meant to be infused under the skin, a common reaction is infusion site swelling. This reaction is particularly pronounced in single subcutaneous sites where the infusion volume is high and/or the infusion rate is fast. When these infusions are administered with a syringe and needle or administration set, infusion site swelling has no consequence to the injection device. However, as more drugs are being presented in automatic injection devices that are adhered and worn on the body during the infusion, site swelling presents a challenge in keeping the automatic injection device secured to the body. In particular, the lump or bulge formed by the infused solution at the skin surface may dislodge an automatic injection device from the infusion site if the adhesive on the injection device is not properly designed. Accordingly, there exists the need for an automatic injection device with properly designed adhesive that allows for bulging at the injection site without compromising the adherence of the device to the patient.

Figure 66:
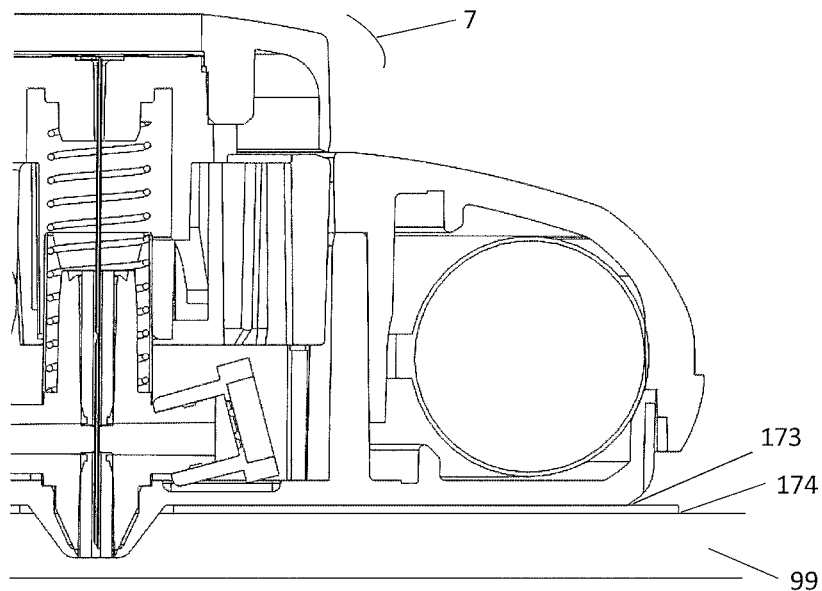
FIG. 66 is a cross-section of FIG. 55 showing adhesive/device and adhesive/skin interfaces.

Referring to FIG. 66, there are two interfaces related to adhering the injection device 7 to the skin 99. The first is the adhesive/device interface 173 and the second is the adhesive/skin interface 174.

Figure 67:
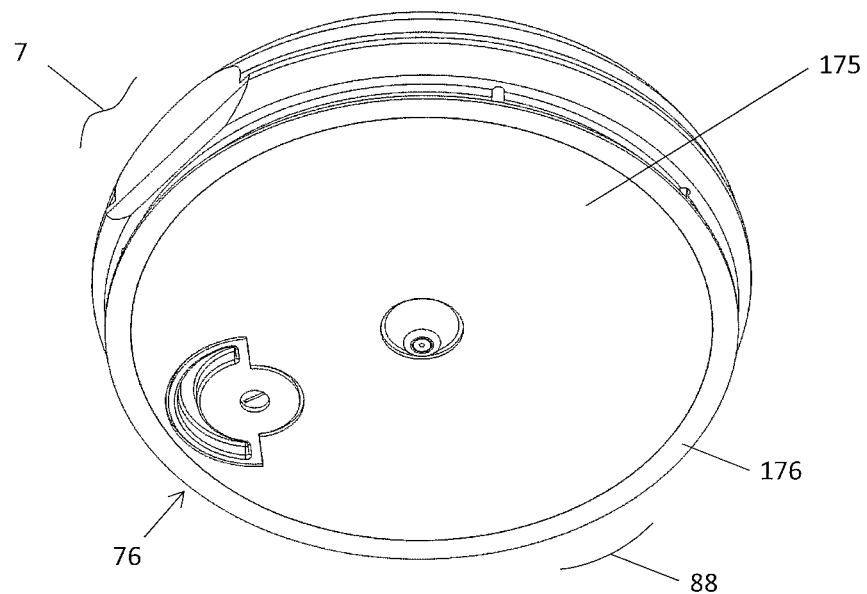
FIG. 67 is a perspective view of the bottom of an injection device showing the different zones of the adhesive.

Referring to FIG. 67, the adhesive 88 could be configured on the injection device 7 with at least two zones. The first zone 175 may include a permanent bond using mechanical or chemical means between the adhesive 88 and the injection device 7 and preferably be positioned within the perimeter of the injection device 7. The second zone 176 may be configured to be detachable or unattached from the injection device 7 and preferably be adjacent and on the outside (e.g., radially outward) of zone 1.

Figure 68:
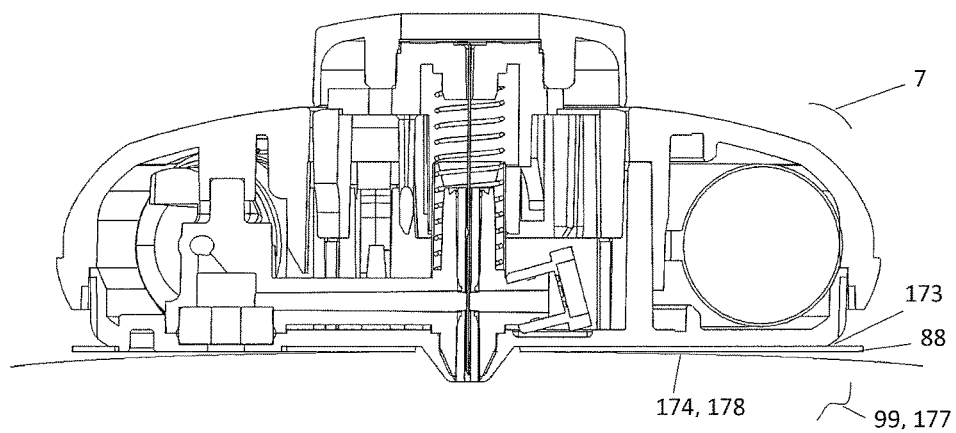
FIG. 68 is a cross-section of FIG. 55 showing bulging tissue on a device with permanently attached adhesive.

Referring to FIG. 68, if the adhesive 88 were completely attached to the bottom 76 of the device 7, during a tissue bulge 177 event the adhesive 88 at the adhesive/skin interface 174 would start to peel from the skin 99 because this interface 174 is weaker than the adhesive/device interface 173. This is demonstrated on a bulging surface in FIG. 68. This may result in the injection device 7 becoming dislodged from the skin surface 99 and falling off the patient.

Figure 69:
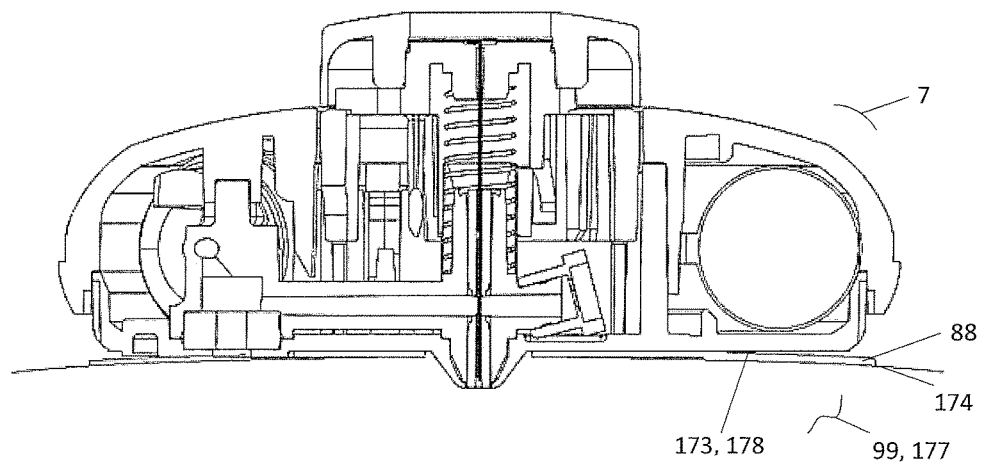
FIG. 69 is a cross-section of FIG. 55 showing bulging tissue on a device with multi-zone attached adhesive.

Referring to FIGS. 67 and 69, instead of permanently attaching the adhesive 88 completely to the bottom 76 of the injection device 7 as shown in FIG. 68, the adhesive 88 could be configured on the injection device 7 with the abovementioned zones 175, 176. During a tissue bulge event 177 in this configuration, the adhesive 88 in zone two 176 would detach from the injection device 7 and be firmly attached to the skin 99 surface at the adhesive/skin interface 174. This would allow for transfer of the peel edge 178 from the adhesive skin interface 174 to the adhesive/device interface 173 effectively creating a strain relief at the adhesive/skin interface. The adhesive/device interface 173 may be designed to be much stronger and prevent injection device 7 separation from the skin surface 99.

When performing self-injections with automatic injection devices, protecting the user from accidental needle sticks is a beneficial requirement for the device. Typically, the needle is retracted within the device before and after use, preventing the user from accessing the needle. However, during the injection, the needle is extended outside of the device. If the automatic injection device were body worn and inadvertently fell off the user during the injection, the needle would be exposed creating a potential needle stick hazard to the user. Accordingly, there exists the need for an automatic injection device with a skin dislodgement sensor to automatically retract a needle if the device becomes dislodged from the skin during the injection.

Figure 70:
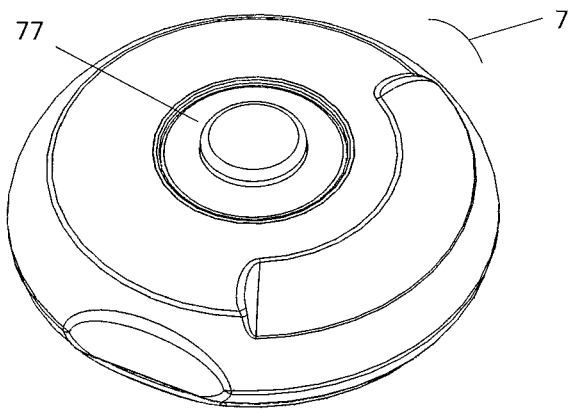
FIG. 70 is a perspective view of the top of an alternative injection device.
Figure 71:
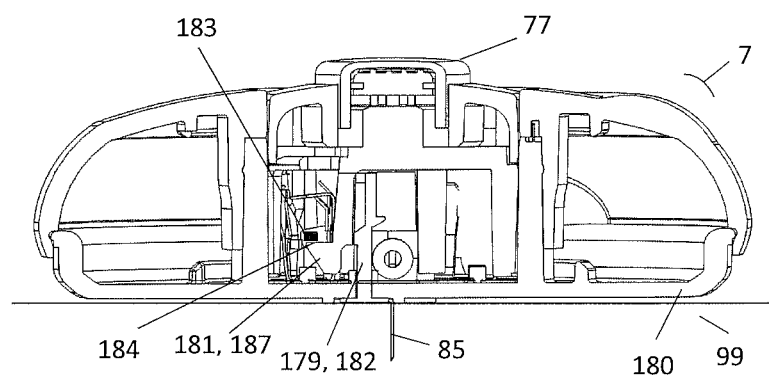
FIG. 71 is a cross-section of FIG. 70 showing a dislodgment sensor non-engaged and the needle locked in the dispense position.
Figure 72:
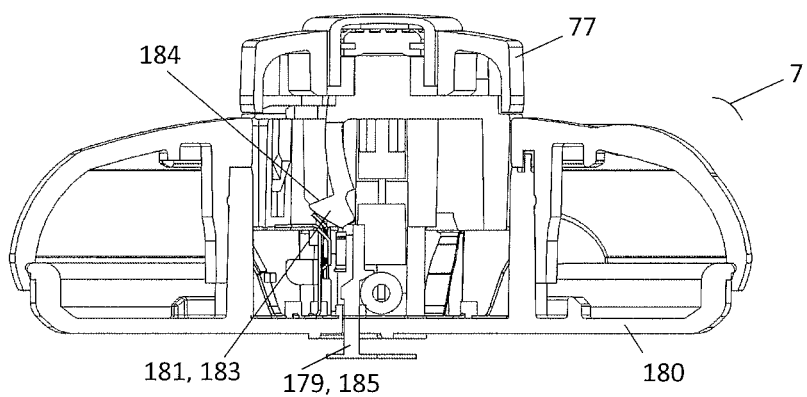
FIG. 72 is a cross-section of FIG. 70 showing a dislodgment sensor engaged and the needle and button retracted to post-fire position.

Referring to FIG. 70-72, a skin dislodgement sensor 179 may be in operative engagement with a flexible latch 181 of the button 77 and slidable within the lower housing 180 of the injection device 7. Referring to FIG. 71, when the injection device 7 is attached to the skin surface 99, the skin dislodgement sensor 179 is forced into a first or up position 182 inside the injection device 7. When the button 77 is actuated to a fired state or second position or dispense position (exposing the needle 85), the flexible latch 181 is forced into a lock position 187 by the skin dislodgement sensor 179 under the latch board 183. The latch board 183 holds the button 77 at the latch board surface 184 on the button 77 down in the fired state or dispense position until the end of dispense. At the end of dispense, the latch board 183 translates away from the latch board surface 184 on the button 77, allowing the button 77 and needle 85 to retract to a post fire position where the needle 85 is contained within the injection device 7. Referring to FIG. 72, in the event that the injection device 7 becomes dislodged from the skin surface 99 during injection, the skin dislodgement sensor 179 extends to a second or down position 185 out of the injection device 7. This allows the flexible latch 181 to spring back to an unlocked position and disengage from the latch board 183. This allows the button 77 and needle 85 to retract to a post fire position where the needle 85 is contained within the injection device 7.

When performing self-injections with a syringe and needle, users may have the need to temporarily stop or pause the injection due to acute pain or irritation at the injection site. This pause in flow of injectable into the injection site, accomplished by removing pressure on the plunger rod of the syringe, helps to reduce the pain at the injection site by allowing the injectable fluid bolus more time to diffuse into the surrounding tissue and thus reducing the local pressure and associated pain and irritation. However, as more drugs are being presented in automatic injection devices, the ability to manually pause these types of automatic systems does not exist. Once an automatic injection device is placed on the skin and the cannula is introduced, there is no way for the user to pause the injection due to pain or irritation at the injection site. Accordingly, there exists a need for a user to be able to pause an automatic injection system.

Figure 73:
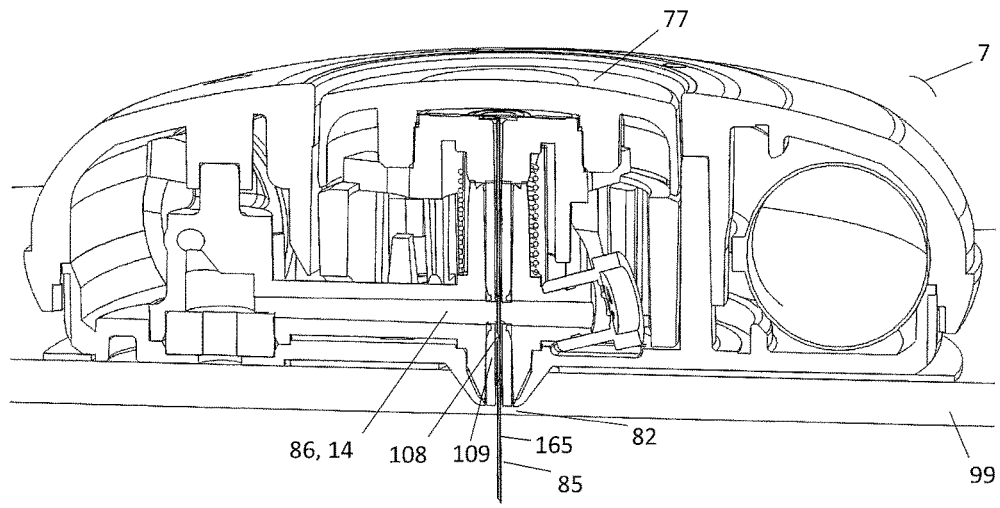
FIG. 73 is a cross-section of FIG. 55 showing an injection device with the button in the first position or pause position.
Figure 74:
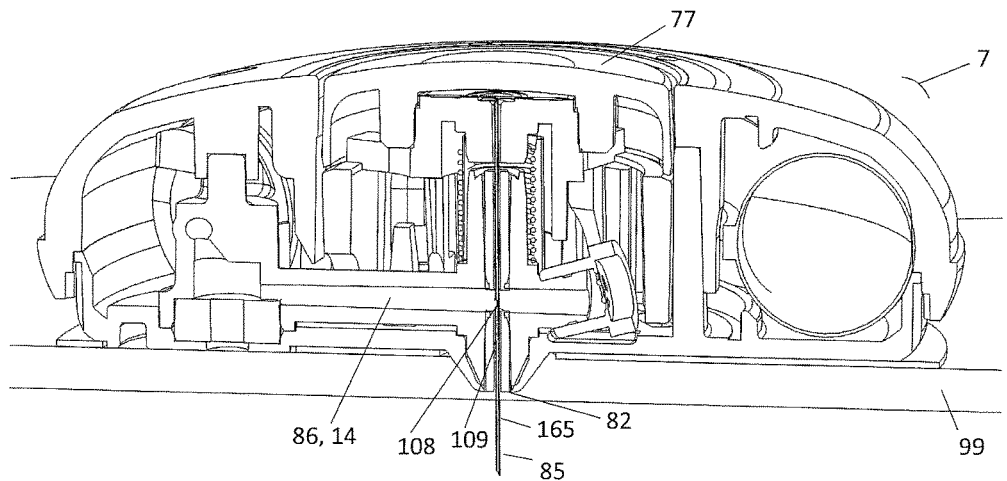
FIG. 74 is a cross-section of FIG. 55 showing an injection device with the button in a second position or dispense position.

Referring to FIGS. 73-74, upon actuation of the button 77, the needle 85 and button 77 travel to a first position or depth as shown in FIG. 73. In this first position or depth, the side-hole 108 is covered by the septum 109 and therefore the internal lumen 165 of the needle 85 is not in communication with the fluid channel 86 of the dispense port 82. The button 77 may be intentionally held in this first position or depth to prevent flow of injectable 14 from the fluid channel 86 into the side-hole 108 of the needle 85 and into the skin 99. As shown in FIG. 74, when the button 77 is released, the needle 85 and button 77 return to a second position or dispense position where the side-hole 108 is exposed to the fluid channel 86 allowing the flow of injectable 14 from the fluid channel 86 into the side-hole 108 of the needle 85 and into the skin 99 until the end of the injection. This action of pushing the button 77 to the first position or depth may be performed as many times a necessary during the entire injection.

Figure 75:
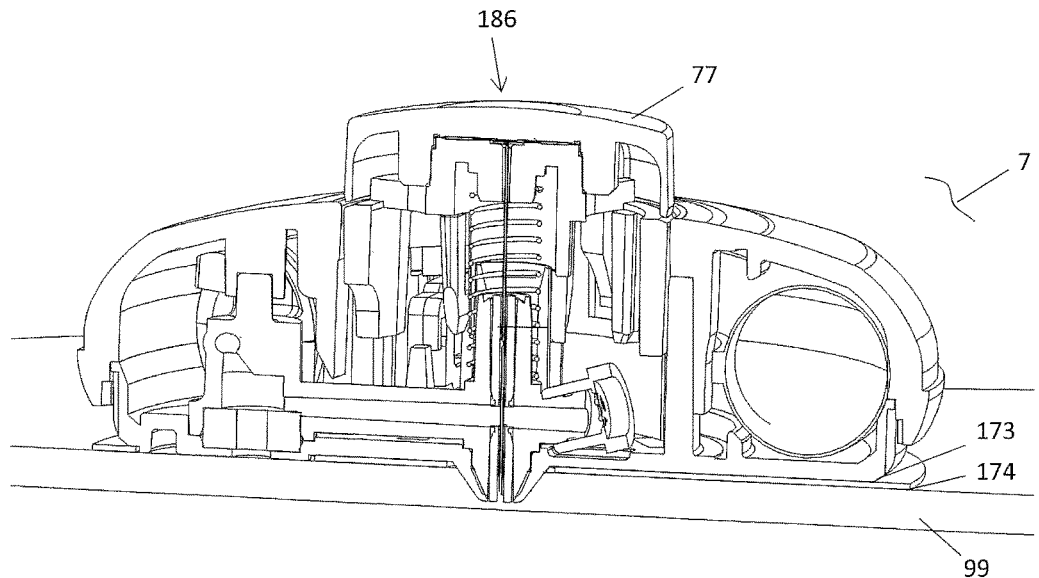
FIG. 75 is a cross-section of FIG. 55 showing an injection device with the needle retracted and the button in the up or pre-fire position.
Figure 76:
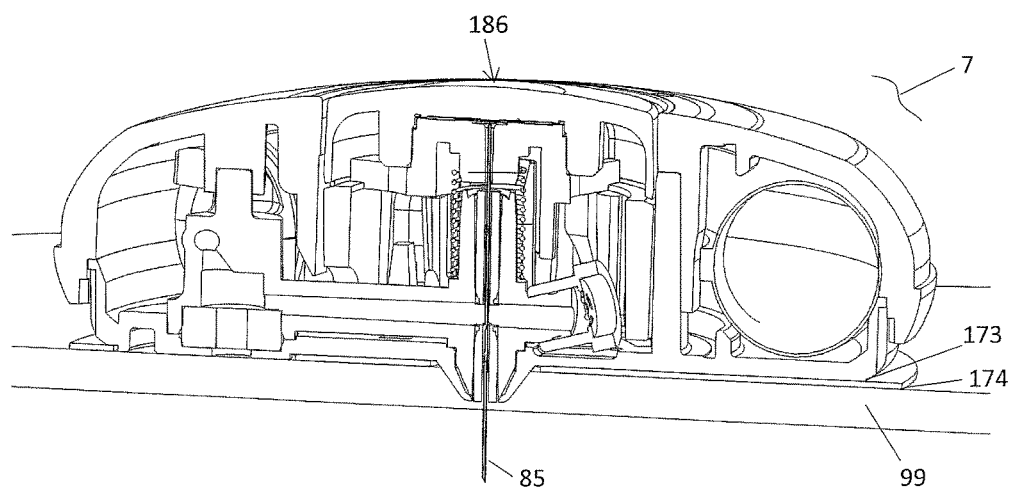
FIG. 76 is a cross-section of FIG. 55 showing an injection device with the button in a second position or dispense position.

Referring to FIGS. 75-76, the button 77 actuation force 186 is the transition load applied to the button 77 required to start displacement of the button 77 and needle 85 from a pre-fire position to a fired state or dispense position. Until this transition load is met, the force 186 applied to the button 77 is transferred directly to the injection device 7. Specifically, this load 186 may be transferred to adhesive skin interface 174 and/or the adhesive device interface 173 resulting in better securement of the injection device 7 to the skin surface 99 prior to actuation of the injection device 7.

Figure 77:
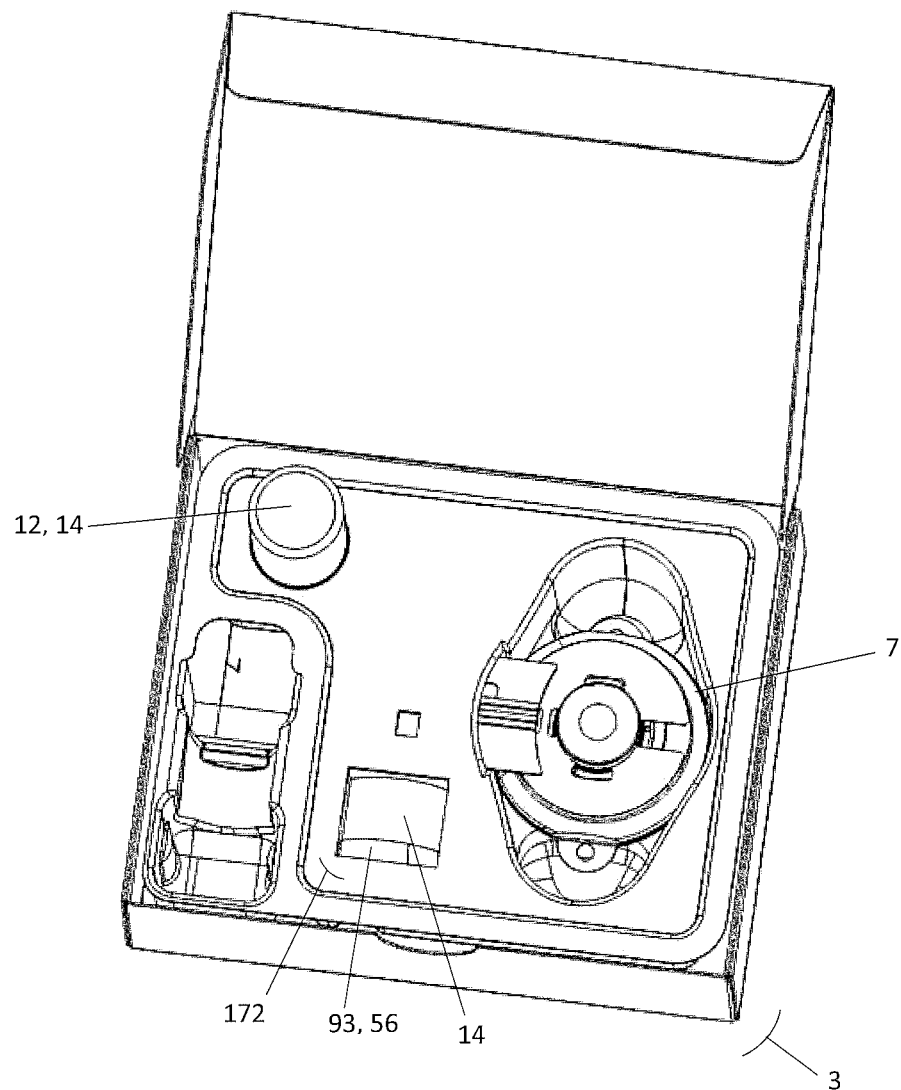
FIG. 77 is a perspective view of a single vial transfer apparatus.

Referring to FIG. 77, an indicator window 172 on the transfer apparatus 3 may be present to show that the transfer of fluid 14 and/or mixing is progressing. This indicator window 172 could be configured in the base of the transfer apparatus 3 and track the movement of the plunger 93 of the pressure chamber 56 within the transfer device 3. The indicator window 172 could be configured with a scale or other means to track the movement of the plunger 93. Alternatively, the plunger 93 could be configured with a different color to make it easy to track its movement in the indicator window 172. The combination of the indicator window 172 and plunger 93 could provide the progress of withdrawing fluid 14 from the vial 12 and filling of the chamber 56. The combination of the indicator window 172 and plunger 93 could also provide the progress of the transfer of fluid 14 from the chamber 56 to the injection device 7.

Figure 78:
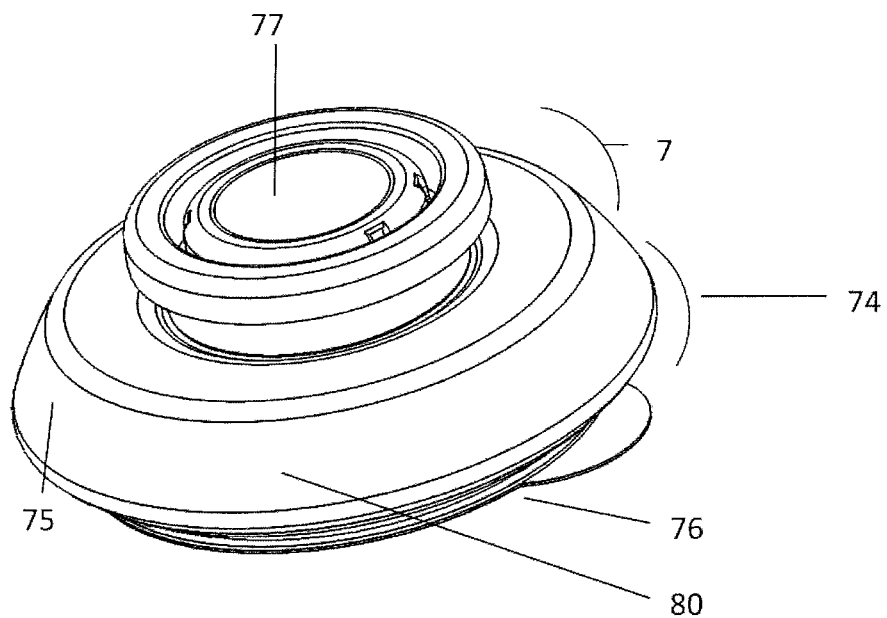
FIG. 78 is a perspective view of an injection device.
Figure 79:
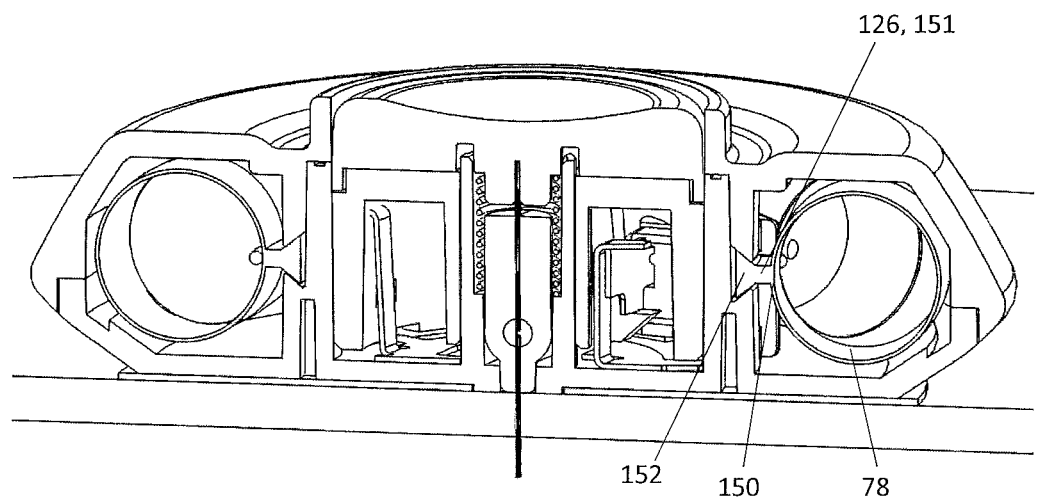
FIG. 79 is a cross-section of FIG. 78 showing an injection device with the button in a second position or dispense position.

Referring to FIG. 78-79, the arcuate expandable member 78 is positioned and/or will preferably expand in length in an arc shape. In the illustrated embodiment, the arc shape is induced by providing a less resilient area for example a thicker or relatively heavy wall thickness zone 126 which will result in less deflection of the expandable member in that zone and result in formation of an expanded arc shape. This heavy wall thickness zone 126 may be configured in any shape that will allow for the arc shape in the expandable member 78 during expansion. A preferred configuration for the heavy wall thickness zone 126 is to minimize its thickness or attachment 150 in the circumferential direction on the expandable member 78 wall and maximize the radial thickness or projection 151 away from the expandable member 78. This serves to urge the expandable member 78 to expand in an arc shape but also maximizes the amount of material along the circumference that is unaffected by the heavy wall thickness zone 126 for expansion. Additional features including but not limited to a T-shape may be configured to the end of the radial projection 152 to help urge the expandable member 78 into an arc shape.

Figure 80:
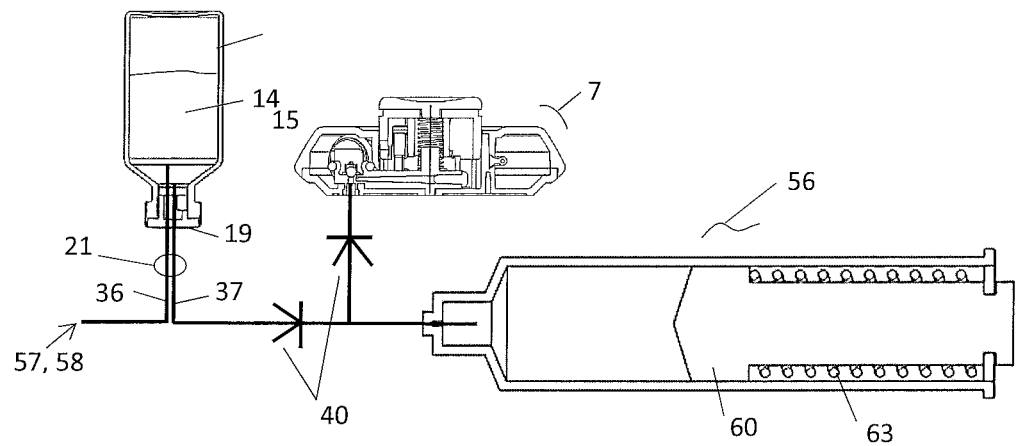
FIG. 80 is a schematic of an alternative embodiment of the single vial transfer system in FIG. 64 with a drug vial, a transfer apparatus with a first variable pressure chamber, an injection device including the fluid pathways with check valves and flow restrictors.

Referring to FIG. 80, the volume of the pressure chamber 56 could be set to be larger than the total fluid volume 14 in the vial 15 so that additional air 58 is drawn into chamber 56 from the vial 15. This additional air 58 could be helpful in insuring that all of the liquid 14 is removed from the vial 15 and removal or clearing of residual liquid 14 in the fluid pathways 35 between the vial 15 and the chamber 56. Additionally, during transfer of the liquid 14 from the chamber 56 to the injection device 7, the additional air may be useful in the removal or clearing of residual liquid 14 in the fluid pathways 35 between the chamber 56 and the injection device 7.

Figure 81:
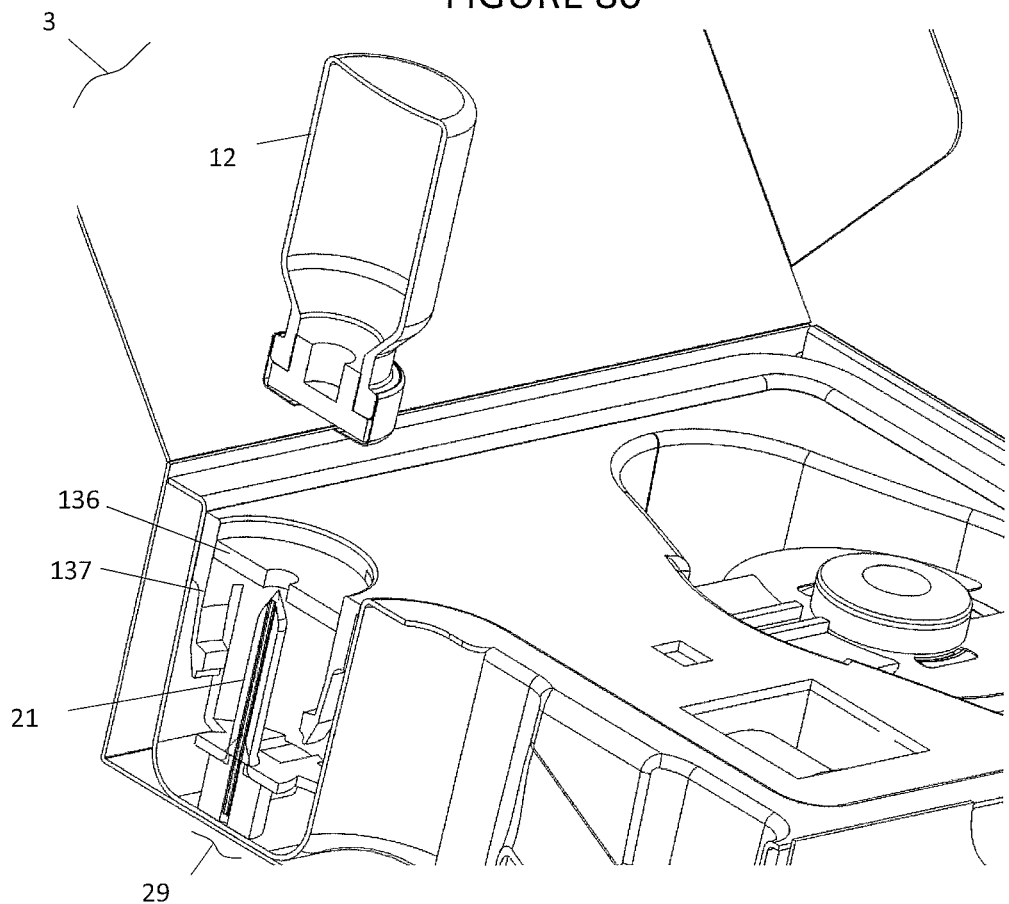
FIG. 81 is a cross-section of FIG. 77 depicting an aspect of the vial receiving area.

Referring to FIG. 81, the transfer apparatus 3 comprises a vial holder docking area 29 that may include an elongated vial access member or piercing member 21. This vial holder docking area 29 may include a vial access protector 136. The vial access protector 136 is locked and held in a first position above the vial access member 21 by locking fingers 137 within the vial holder docking area 29 prior to insertion of the vial 12 or vial holder to cover the vial access member 21 and prevent inadvertent vial access member stick by the user. When the vial 12 or vial holder is inserted into the vial holder docking area 29, the vial 12 or vial holder displaces the locking fingers 137 and unlocks the vial access protector 136. Once unlocked, the vial access protector 136 is movably slidable within the vial holder docking area 29 with the the vial 12 or vial holder.

Figure 82:
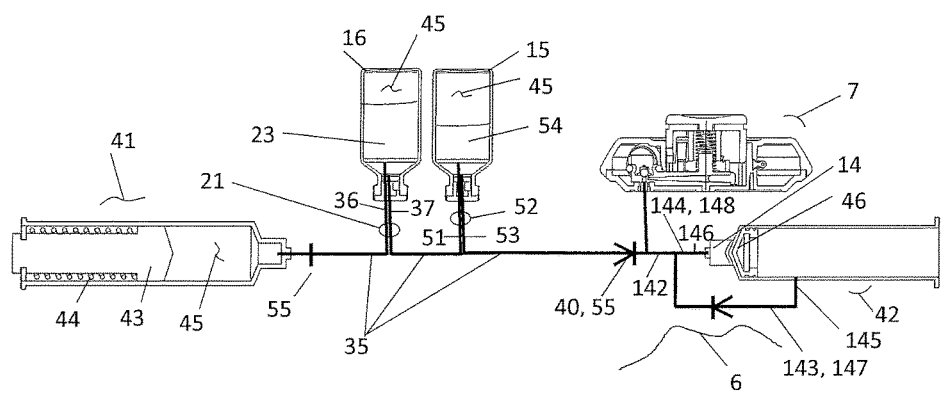
FIG. 82 is a schematic of a dual vial transfer system with a first vial, a second vial, a transfer apparatus with a first and second variable pressure chambers and injection device including the fluid pathways.

Referring to FIG. 82, flow restrictors 55 may be used in the fluid pathway 35 to control and/or delay the transfer time and/or increase the mixing time. Small lumen tubing could be used at any point in the flow path 35 to restrict flow and increase the time of mixing/transfer for times up to an hour or more. One method to control and/or delay the transfer time and/or increase mixing time between the second pressure chamber 42 and the injection device 7 is by the use of multi-lumen fluid pathways 142 between the second pressure chamber 42 and injection device 7. Each lumen 143, 144 of the fluid pathway 142 is attached to a specific location 145, 146 on the second pressure chamber 42, preferably spaced apart along the travel of the piston and has an internal diameter 147, 148 sized to provide for a specific flow rate through that lumen 143, 144 based on the pressure within the second pressure chamber 42. Initially as the second pressure chamber piston 46 starts its advance in the chamber 42, the fluid mixture 14 is dispensed through all of the lumens 143, 144 in the fluid pathway 142 to the injection device 7. Once the piston passes over an attachment point 145 between a lumen 143 and the pressure chamber 42, the flow of fluid through that lumen 143 stops and fluid 14 is forced through the remaining lumen 144. Multiple lumens and attachment points could be positioned along the pressure chamber. The final lumen 144 available from flow of fluid 14 could be sized with an internal diameter 148 that is very small. Accordingly, the flow rate would be very low, increasing the time to transfer the fluid 14 from the chamber 42 to the injection device 7. This delay of transfer allows for increase mixing time.

Figure 83:
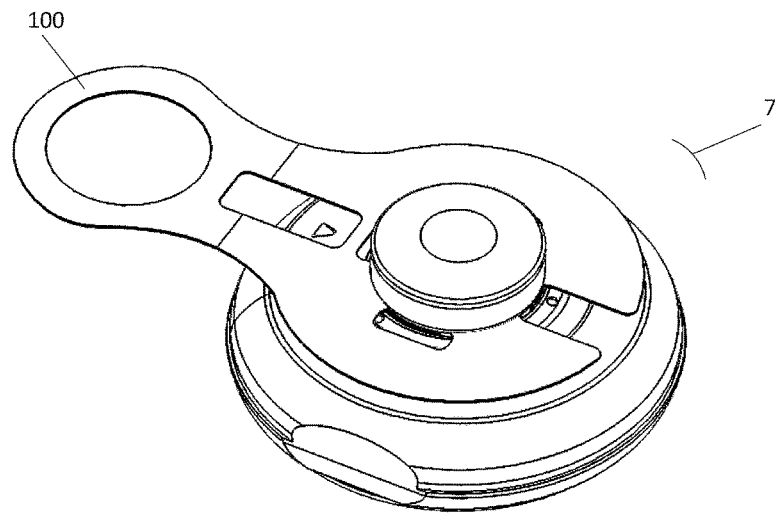
FIG. 83 is a perspective view of an injection device with the attached safety sleeve.

Referring to FIG. 83, a safety, such as a safety pin or safety sleeve 100 may be configured to allow for removal from the injection device 7 in any direction to release the injection device 7 to be ready to fire (inject).

Figure 84:
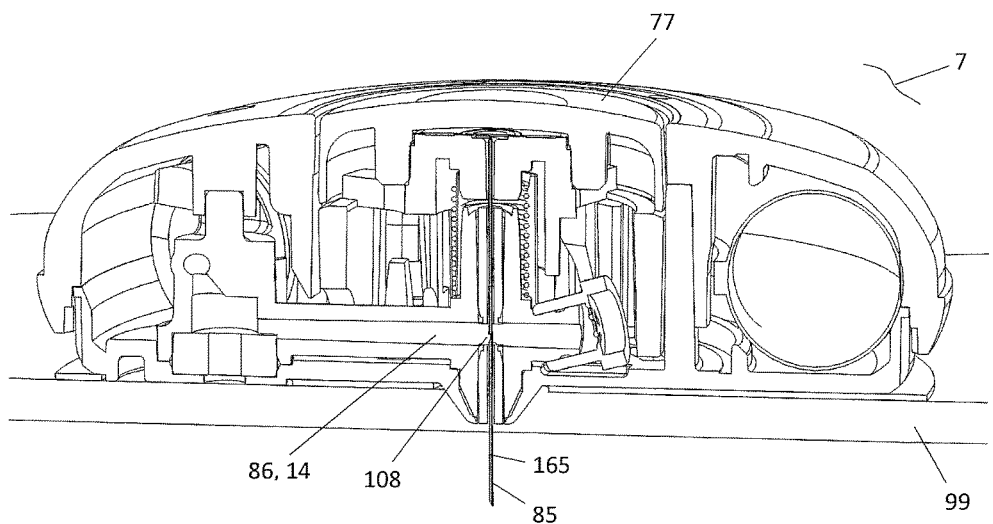
FIG. 84 is a cross-section of FIG. 55 showing an injection device with the button in second position or dispense position.

Referring to FIG. 84, the injection device 7 includes a needle 85 with a side-hole 108 that allows for fluid communication between the fluid channel 86 and the skin 99 once the button 77 is fully depressed in the injection device 7. This starts dispense of the injectable 14. The inner diameter 165 of the needle 85 is significant in controlling the rate of dispense from the injection device 7. Referencing the Hagen-Poiseuille equation for fluid flowing in a pipe, the flow rate through a pipe is directly proportional to the radius of the pipe to the fourth power. Thus, small variations in the inner diameter 165 of the needle 85 result in large variations in flow through the needle 85, especially as the inner diameter 165 gets smaller. The needle 85 in the injection device 7 may range from 21G to 34G (Stubs Iron Wire Gauge System) in various wall thickness configurations. This range corresponds to an inner diameter 165 range of 0.021" to 0.003", recognizing that there is manufacturing variation or tolerance with the needle inner diameter 165 in any given needle size. This is based on needle size and can have an inner diameter variation as much as ±0.00075". To limit the range of the inner diameter 165 within any given needle size and resulting variation in flow, the needle 85 may be modified prior to assembly into the injection device 7. This modification could include crimping, flattening or rolling the needle to a new, prescribed effective inner diameter 165 over a portion of the length of the needle 85 from a circular shape to a non-circular shape. This has the advantage of allowing for specific delivery rate control from the injection device 7.

Figure 85:
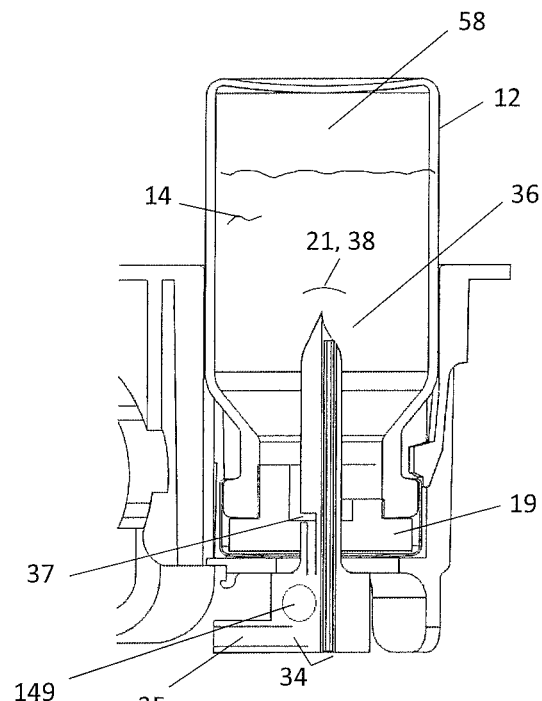
FIG. 85 is a cross-section of FIG. 59 depicting an aspect of the vial holder area showing the drug vial, vial access member and angle sensor in the open position.
Figure 86:
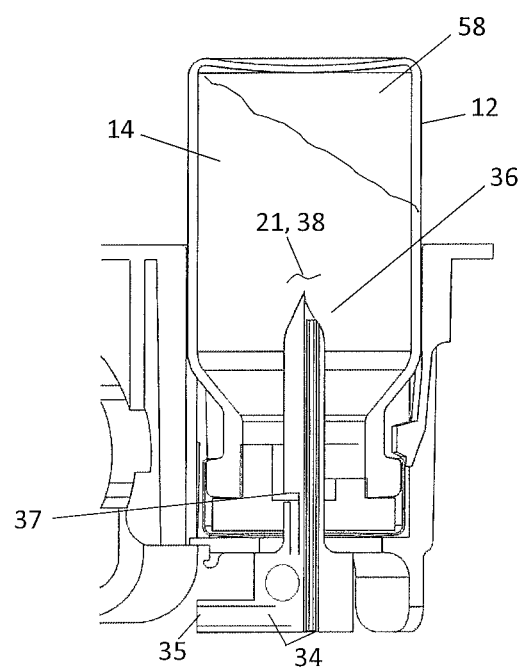
FIG. 86 is a cross-section of FIG. 59 depicting an aspect of the vial holder area showing the drug vial, vial access member and angle sensor in the closed position.

Referring to FIGS. 85-86, the lumen openings 38 in the vial access member 21 can be oriented to allow for introduction of pressurized air or liquid through the upper inlet tube 36 and output of the vial contents 14 through the lower output tube 37. Further, the outlet opening 37 may be positioned near the bottom of the inverted vial 12, adjacent to the septum 19 to encourage the entire contents 14 of the vial 12 to enter the outlet port 37 and be removed from the vial 12. The preferred sequence for removal of the contents 14 from the vial 12 is first all of the fluid 14 in the vial 12 and then the air 58 from the vial 12. This is achieved with the current embodiment when the orientation of the transfer apparatus 3 is oriented as shown in FIGS. 85-86. Based on the geometry of the vial access member 21 within the vial 12, this sequence of all fluid 23 then air 58 removal is achieved up to transfer apparatus 3 angles of +/−45 degrees from horizontal. Beyond this angle, there is the possibility that air 58 is introduced before or during fluid 14 removal from the vial 12. An angle sensor 149 may be positioned in or around the vial access member 21 to sense the angle of the transfer apparatus 3. It may have direct communication with either or both of the lumen openings 38 and/or each or both of the inlet tube 37 and output tube 36. In the current embodiment as shown in FIG. 85, when the transfer apparatus 3 is at an angle less than 45 degrees, the sensor 149 allows fluid communication between the outlet port 37 and the fluid pathways 35. As shown in FIG. 86, if the transfer apparatus 3 were tilted to an angle greater than 45 degrees, the sensor 149 may rotate or translate to a new position to shut off the fluid communication between the outlet port 37 and the fluid pathways 35.

Figure 87:
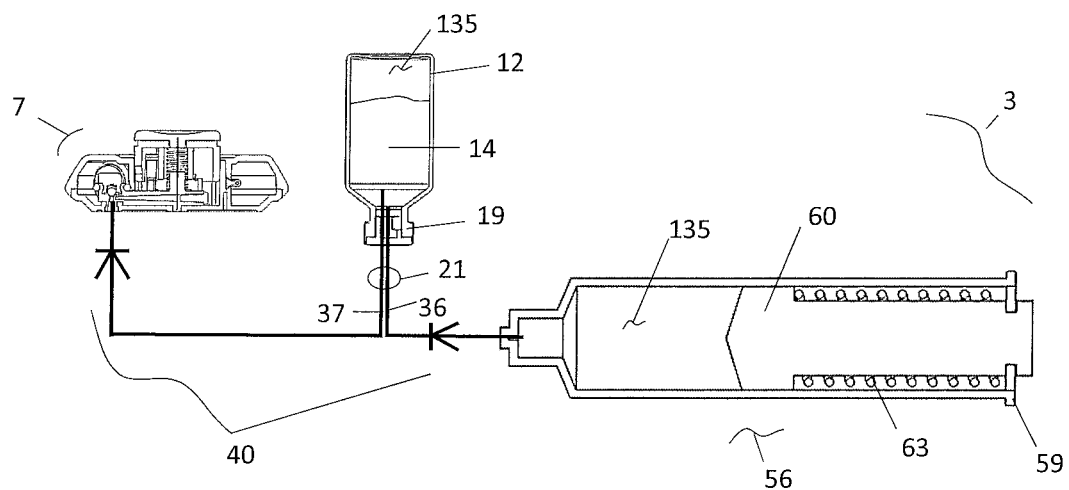
FIG. 87 is a schematic of an alternative embodiment of the single vial transfer system with a drug vial, a transfer apparatus with a first variable pressure chamber and an injection device including the fluid pathways with check valves.

Referring to FIG. 87, an alternative transfer apparatus 3 within a single vial system that does not perform mixing but only transfers fluid 14 from a single vial 12 to the injection device 7 is provided. This alternative transfer apparatus 3 includes a vial 12, a variable volume pressure chamber 56 and fluid pathways 35 to direct the contents 14 from the vial 12 into the injection device 7. The inlet tube 36 of the vial access member 21 is connected to the variable volume pressure chamber 56 with fluid pathways 35. The outlet tube 37 of the vial access member 21 is connected to the injection device 7 through fluid pathways pressure chamber 56.

Referring to FIG. 87, the full insertion of the vial 12 into the transfer apparatus 3 by the user causes the introduction of the vial access member 21 through the septum 19 of the vial 12 to access the contents 14 of the vial 12. This also triggers the release of the pressure chamber trigger 59. The plunger 60 is in a retracted position and the pressure chamber 56 is full of air 135. The pressure release trigger 59 releases the plunger 60 within the pressure chamber 56 connected to a dispense spring 63. The dispense spring 63 advances the plunger 60 and displaces air 135 from the pressure chamber 56 into the single vial 12 though the inlet tube 36. Air 135 entering the vial 12 displaces the fluid 14 out of the vial 12 through the outlet tube 37 into the injection device 7. This continues until all of the fluid 14 is displaced out vial 12 into the injection device 7. Check valves 40 could be employed to prevent fluid 14 from going back into the vial 12 or fluid 14 from going back into the pressure chamber 56.

Syringe Contents Transfer

The present subject matter is directed, in part, to a disposable, one-time-use apparatus and methods for preferably transferring, upon user initiation, the injectable contents of one or more standard syringes into an injection device and preferably simultaneously pressurizing the injection device for subsequent automated injection into a subject. The apparatus and method described herein may be of any suitable detailed configuration, but is preferably configured to transfer the contents of a syringe into an injection device. The apparatus and method may employ any of the features or aspects described above, alone or in combination with the features or aspects described below and/or show in the attached figures. Also, the apparatus may be configured to allow the user to select a dose volume to be transferred to the injection device and subsequently delivered to the subject. The apparatus may further be configured to filter the contents for removal of particulate or drug particles before transfer into the injection device, and may include a sterile filter for filtering any displacement air captured in the syringe or syringes. The apparatus may further be configured with one-way valves to only allow the user to transfer injectable from the syringe into injection device. Also, the apparatus may further be configured with one-way valves to prevent pressurized injectable in the injection device from flowing back into the apparatus at the filling port. The apparatus may also include a lockout to prevent the user from removing the injection device prior to drug transfer or from activating the injection device until the device has been removed from the transfer apparatus.

At the time of use, the user inserts the filled syringe into the syringe receiving area. The user depresses the syringe plunger or piston to manually transfer the injectable through the transfer apparatus into the injection device. This simultaneously charges the injection device (e.g., expanding and pressurizing the expandable member or balloon by introducing the injectable thereinto under pressure) so that the injection device is ready for automated injection into a subject upon user activation.

Figure 88:
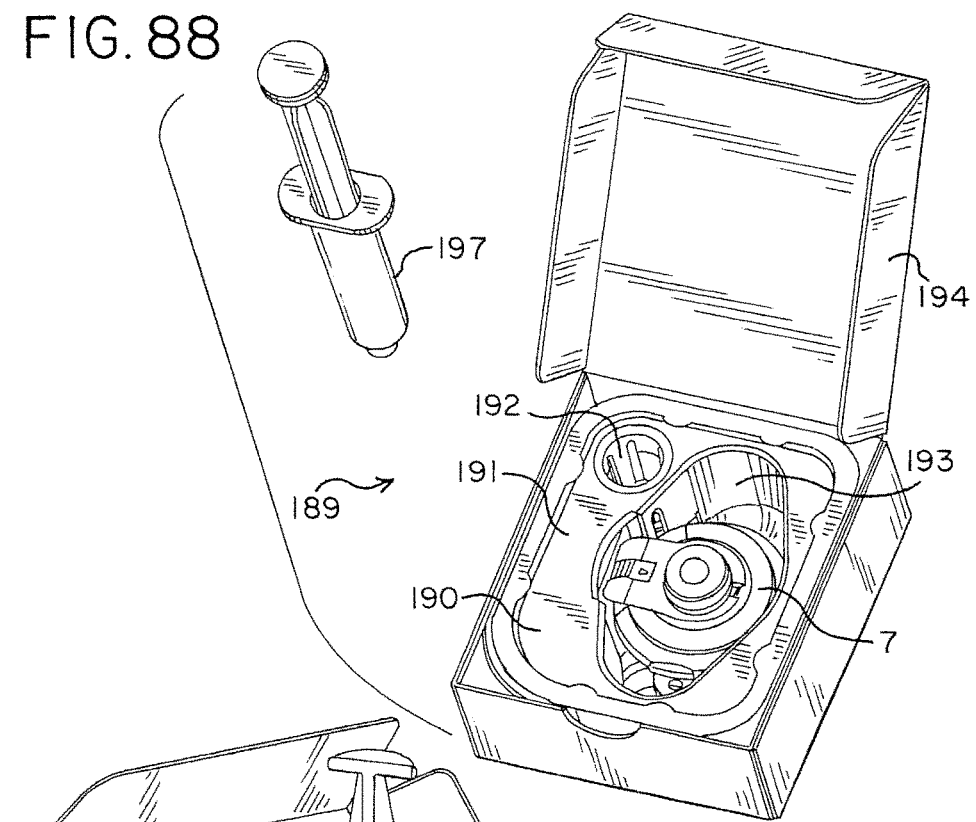
FIG. 88 is a perspective view of a transfer device, with an associated injection device, embodying the present subject matter for use in transferring the contents of a syringe, also shown, into the injection device.
Figure 89:
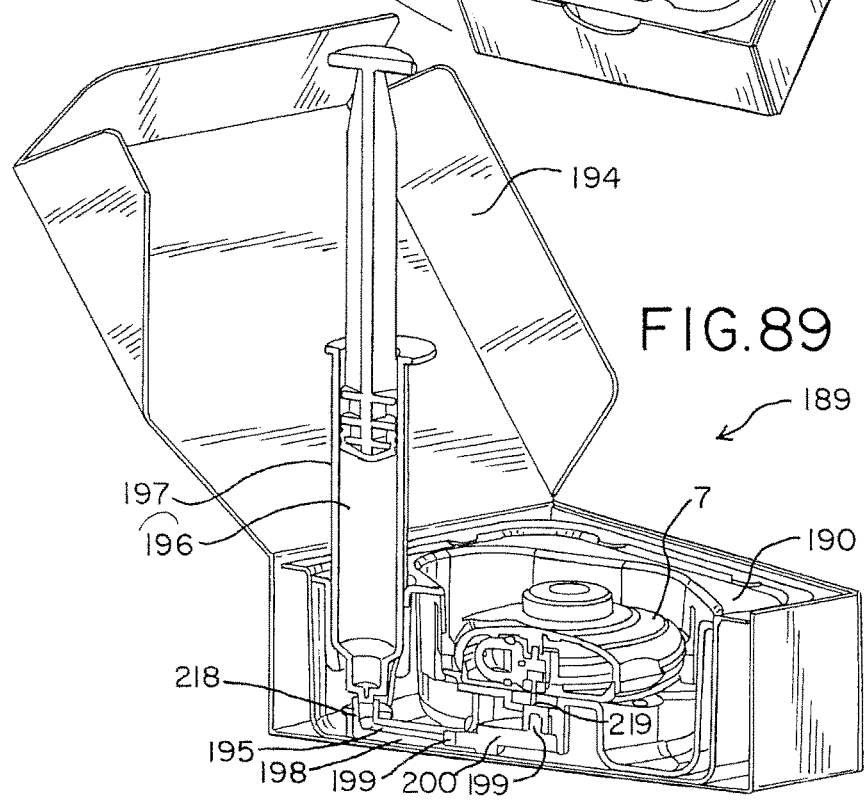
FIG. 89 is a vertical cross-sectional view take through the transfer and injection device with the syringe located in a docking station on the transfer device.

Referring to FIGS. 88-90, the disposable, one-time use, manual syringe transfer and injection system 189 may comprise a transfer apparatus 190 and injection device 7. Referring to FIG. 88, the transfer apparatus 190 has, among other features, an outer housing or base 191 of rigid molded plastic or other suitable material and defines a syringe docking area or first receiving station 192 for receiving a syringe such as a standard syringe and an injection device docking station or second receiving station 193 (for removable injection devices such as an injection device as previously described in detail above). In the illustrated structure, the syringe docking station 192, which may be in the form of a cylindrical recess, and injection device docking station 193 are spaced apart, such as at opposite ends of the transfer apparatus housing 191. As in earlier embodiments and with the same benefit, the transfer apparatus 190 may have an outer housing 191 that is integrated into the packaging 194 of the system.

Referring to FIGS. 89-90, the transfer apparatus 190 has at least one fluid pathway 195 extending from a syringe connector port at one end 218, such as a female luer syringe connector within the cylindrical recess, and a port or outlet 219 at another end such as in the injection device docking station for mating or connecting to an inlet of the injection device. The fluid pathway 195 may be a single pathway or include an array of internal fluid pathways 195, as required to perform any transfer of the injectable 196 and conveying or transferring it from the syringe 197 in the syringe docking area 192 to the injection device 7 in the injection device docking station 193. The fluid pathway(s) 195 may include flexible or rigid conduits or tubing 198 that form all or part of the pathway. The fluid pathway(s) 195 may also include check valves, such as a check ball 199, to control fluid flow from the syringe to the injection device and to prevent backflow; one or more filters 200, such as submicron filter membrane to filter the injectable 196 during transfer to the injection device 7. The filter 200 may have other characteristics also, such as being hydrophilic to block air from flowing to the injection device 7, or hydrophobic to connect the flow path to a vent passageway and prevent fluid flow through the vent passageway, flow restrictors or other means to convey, control and/or direct the drug 196 from the syringe 197 through transfer apparatus 190, into the injection device 7.

Injectable Warming

A significant portion of injectable biopharmaceutical drugs require cold storage conditions (typically 2-8° C.) for long-term stability. These drugs must be maintained at this lower temperature until the time of use or risk therapeutic failure due to a lack of potency. Presently, at the time of usage, patients are required to remove the drug from the refrigerator and allow it to naturally warm to ambient or room temperature, which can typically range from about 15 to about 32° C., before administering. Depending on the drug container, e.g., packaged or unpackaged vial or prefilled syringe, this process may take up to one-half hour or more. If the drug/device is not allowed to warm, there are a number of potential problems. First, the drug viscosity can increase by a factor of three or more because of the cold solution temperature, making the fluid more difficult to inject through a small needle into a patient. Second, if the device is electronically driven, a cold battery can have a significantly lower energy and may not function as well as desired. Third, a cold drug is significantly more painful for the patient into whom it is injected. Also, users or patients may not be comfortable allowing their injection devices to remain out and in the open for warming for an extended period of time because of concerns about child safety, concerns that they might forget about it, and/or desires to go about their business when they simply don't want to wait for 30 minutes or more to leave their home.

A number of devices are currently being marketed for active heating of refrigerated drug/device combinations. Actively heating the drug solution using a heater, e.g., electrical heater, or other technique (at temperatures above room temperature) may add cost to the product and may result in overheating and subsequent degradation of the drug, representing an additional expense and complication for the user. Thus, a passive system and method that quickly, reliably and safely warm cold or chilled injectables, allowing the user to conveniently use it promptly, right out of the refrigerator, would be very beneficial for the reasons outlined above.

Figure 92:
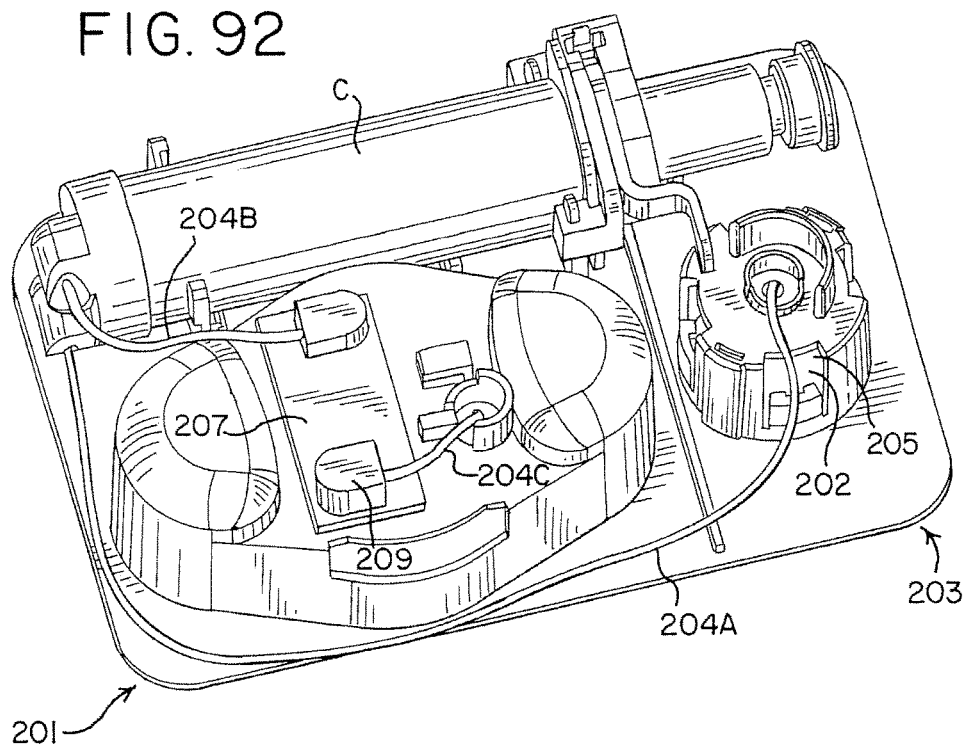
FIG. 92 is a perspective view of the underside of the transfer device of FIG. 91, illustrating some of the fluid contacting surfaces and flow paths that can contact the injectable during transfer and contribute to elevating the temperature of a chilled injectable.

In accordance with further aspects of the present subject matter, referring FIGS. 91 and 92 as well as the other figures, for illustrative purposes only, passive heat transfer can take place from the room-temperature transfer device 203 and injection device 206 structure and from the environment 201, including from room or ambient temperature gas the cold injectable 202. The heat transfer may take place in the transfer device 203 (or the other transfer/injection devices described herein), within the fluid pathways (generally designated 204) between, for example, the vial 205 or syringe and the injection device 206, by contact with room or ambient temperature gas, and within the injection device. Fluid pathways 204 may consist of tubes, conduits, filters, check valves or other components capable of carrying fluid and, more specifically, may optionally be made of or in direct conductive contact with material having high thermal conductivity. Such high thermal conductivity material may be a metal such as copper, stainless steel, aluminum or other metal, or non-metal material with high thermal conductivity, that is compatible with temporary contact with the particular fluid. The fluid pathways may also be configured to enhance or maximize heat-transferring contact between the fluid and the flow path. This may be achieved by maximizing or enlarging the surface of the flow path in contact with the fluid and, more particularly, maximizing or enlarging the ratio of fluid path surface area to unit volume of fluid, such as by increasing the length or reducing the cross-sectional area of the flow path. Also, the fluid pathways may be configured to enhance heat transfer by providing a flow path that has a relatively large high thermal conductivity mass or is contact with a relatively large high thermal conductivity mass. In particular, and as one non-limiting example, the total mass of the material that makes up the flow path, such as high thermal conductivity material, and/or is in direct heat-conductive contact with a flow path, may be substantially equal to or greater than the total mass of the fluid being transferred so as to afford rapid and sufficient heat transfer rate and capacity.

The mass of the heat conductive flow path or contacting material is not the only factor that may be considered in elevating drug temperature during transfer. For example, as mentioned above, the fluid flow path could be configured so that the ratio of the surface area contacting the fluid to a unit volume of fluid is sufficiently large so as to effect all or a portion of the desired heat transfer. Such a flow path could be configured to afford substantial heat transfer, even with a non-metallic flow path material, although high heat transfer material such as a metal or a material having a heat transfer rate comparable to metal may provide greater or faster heat transfer. Separately, or in addition, the flow path could be configured so that work is done (or energy is expended) on the drug or other fluid in the flow path, which would cause additional heating of the fluid. This is still considered passive heating, as no electrical heating source is required and no heating at a temperature above ambient room temperature is used. For example, a relatively long flow path of very small cross-sectional size or diameter would provide a relatively large surface area and enhance conduction between the surface of the flow path and the drug or other fluid flowing therewithin. Such a system may also tend to increase the frictional or shear forces exerted on the fluid, which would serve to increase fluid temperature. To flow liquid at a sufficient flow rate through such an elongated, small diameter flow path may also require significant pressurization of the fluid, such as by mechanical pump or pneumatic pressurization, which would also tend to raise the temperature of the fluid. These various features (flow path material, mass of fluid flow path and contacting material, fluid flow path surface area, and energy expended on fluid during flow through the flow path) may be used separately or in different combinations to obtain the desired heat transfer.

Further, one additional feature that can aid in heat transfer and raising chilled drug temperature is the use of near room or ambient temperature gas to effect the fluid transfer and flow. In other words, the use of gas at room temperature or higher to force the drug or other fluid to flow though the flow path may also contribute to heat transfer and temperature rise. More specifically, the injection of nearly room temperature gas into a drug vial to force the drug therefrom will result is some amount of heat transfer from the gas to the liquid drug. If the gas is also bubbled or otherwise passed through the vial contents, heat transfer from the room temperature gas to the fluid will be further enhanced. The injection of gas from a variable volume pressure chamber into a vial to force fluid from the vial is described earlier with reference to FIGS. 9 and 10. The use of pre-filled pressurized gas cylinders as the motive force for moving injectable through a transfer system is also described in U.S. Provisional Patent Application Ser. No. 62/138,762 filed Mar. 26, 2015, which is hereby incorporated by reference in its entirety. The present drug transfer and injection systems, as described in any of the examples or embodiments above, may use one or more of these heat transfer features, alone or in combination, to raise the temperature of a chilled drug.

Figure 93:
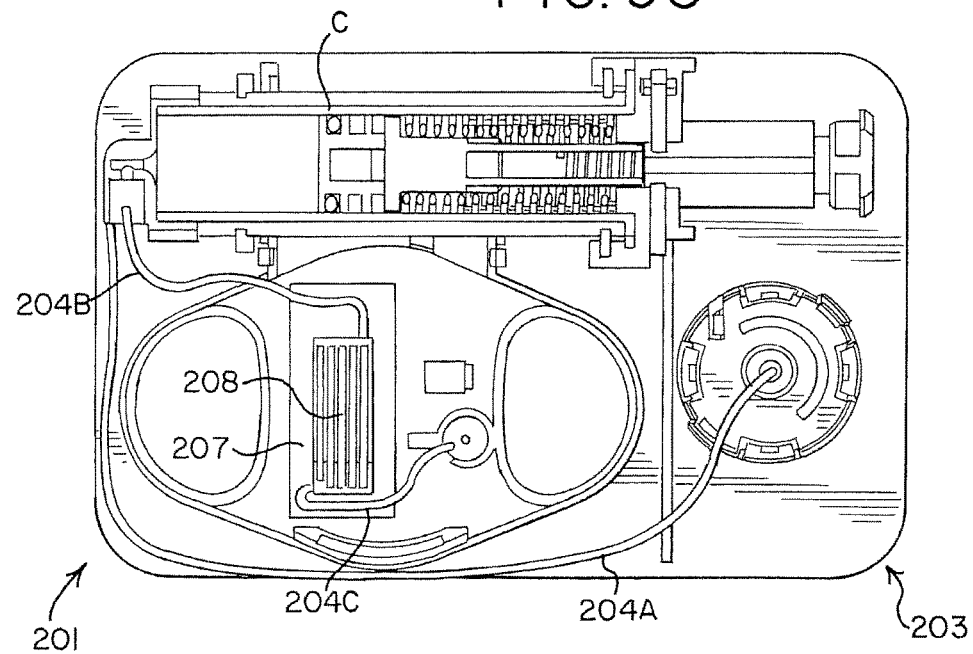
FIG. 93 is a horizontal cross sectional view of the transfer device of FIG. 92 illustrating some of the fluid passageways through which an injectable moves during transfer to an injection device and associated passageway surfaces that contact the injectable and contribute to conductive heat transfer.

For example, ambient or room temperature is typically about 15-32° C., such as about 18-22° C. or about 20° C. Referring to FIGS. 92-93, in an ambient temperature passive transfer device 203, refrigerated injectable 202 of a selected volume (typically about 2-8° C., or about 4-5° C.) can be transferred from the vial 205 or syringe through the fluid pathways 204 and heat exchanging elements and structures 207 within the transfer device 203 to the injection device 206 in a transfer time of from approximately 0.05 to up to 3 minutes or more. During this time, the refrigerated injectable, solution or other fluid 202 can absorb enough heat energy from the ambient temperature fluid pathways 204, from the ambient temperature gas (if used) driving the fluid and from the ambient temperature heat exchanging elements 207 in the transfer device 203 and from the ambient temperature injection device 206 to reach a temperature within about 5° C. or less of ambient or room temperature. The temperature increase may be in the range of at least 5-15° C., such as at least about 10-15° C. For example, a temperature increase from about 4.5° C. to about 13-18° C. or about 16-18° C. in about 80 seconds or less, such as about 30-60 seconds may be achieved. This assumes that the injectable 202 may be aqueous based, such as based on saline or distilled water, although some light oils may be used with other drugs. The quantity of such injectable 202 for a single dose in accordance with the present subject matter may range up to about 50 cc. Typically the range for a single dose may be between about 2 cc and 50 cc and may be less than about 5 cc, depending on the injectable and physician prescription. The injectable viscosity may vary with the type of injectable and the temperature. For example, the injectable may have a viscosity up to about 100 cP.

Referring to FIGS. 92-93, the heat exchange between the ambient environment 201 and the cold injectable drug, solution or other fluid 202 in the transfer device 203 may happen in a number of ways. For example, heat energy may be transferred to the chilled injectable fluid 202 from the transfer device 203 through direct conduction within the fluid pathways 204 between the surface of the pathways and the fluid. The fluid pathways 204 may be configured with a relatively small diameter, and/or extended or long length to enlarge or maximize the amount of room temperature material surface area of the transfer and/or injection devices in contact with the cold fluid or solution 202. For example only, the fluid flow pathway 204 could have a total length from about 0.5 inches to about 5 inches (1.7-12.7 cm), an inner diameter between about 0.01 and 0.1 inches (0.25-2.54 mm) and optionally an inner diameter in the range of 0.01-0.05 inches (0.25-1.2 mm), preferably about 0.05 inches (1.2 mm). This range of flow path diameters (or equivalent cross-sectional areas if the flow pathway is not circular) is applicable to all of the embodiments described above. As noted earlier, longer flow path length and smaller inner diameter (or cross-sectional size) provide more surface area for heat transfer from the ambient environment to fluid flowing through the pathway. The equivalent cross-sectional areas for a non-circular flow path are substantially as follows:

| Circular ID | Equivalent Area |
| --- | --- |
| 0.1 inch | 0.00785 square inches |
| 2.54 mm | 5.064 square millimeters |
| 0.05 inch | 0.00196 square inches |
| 1.27 mm | 1.266 square millimeters |
| 0.01 inch | 0.0000785 square inches |
| 0.254 mm | 0.0506 square millimeters |

Heat energy may also be transferred to the cold fluid 202 through convection from the introduction of room temperature air, such as venting or displacement air, during the withdrawal of fluid 202 from the vial 205 or syringe. The materials of the fluid pathways 204 may be comprised of or in direct contact with thermally conductive metal materials to allow for more effective heat exchange between the environment 201 and the cold fluid 202, such materials including aluminum, copper, and stainless steel or other material, with a thermal conductivity coefficient of about 45-385 W/mK. Fluid pathways 204 may also be comprised of thermally conductive polymers with enhanced thermal conductivity coefficient, such as 1-100 W/mK. Further, as described earlier, heat energy may be transferred to the cold fluid 202 through the kinetic energy, friction and shear forces associated with moving fluid during the transfer process.

Referring to FIGS. 92-93, the fluid pathway, generally identified by reference number 204, is illustrated for purposes of description in the form of tubing, but could also be in preformed fluid flow paths molded as part of the transfer device, or in such other form as may be preferred. As illustrated, flow path section 204A extends from a vial loading station or port to a transfer or pressure chamber C. Fluid or drug flow path section 204B extends from the pressure chamber C to an inlet into the heat exchanging member 207, which is optional. The heat conducting member 207 may comprise a large mass 207 of any of the abovementioned metals or plastics with geometries 208 so as to maximize the ratio of fluid surface area to volume, and may be part of or in contact with materials in the fluid pathway 204. Heat exchanging member 207 may include plural flow paths (see FIG. 93) or a serpentine flow path, for example, to enhance contact between the fluid and the surface of the heat transfer member. The transfer device 203 may also contain additional heat exchanging elements 207 to enhance the heat exchange between the cold fluid 202 and the environment 201. Metal or plastic meshes and/or filters 209 at room temperature may be positioned within the fluid pathway 204 to enhance the heat exchange between the cold fluid 202 and the environment 201. The cold fluid 202 could also be passed through a matrix of heat conductive material such as a matrix formed of stainless steel balls or other small elements within the fluid pathway that allow a high surface area-to-mass contact with the fluid. From the heat exchanger or conductor 207, fluid flow path 204C extends to an inlet or fill port for filling an injection device, such as the injection device described in detail above.

Figure 100:
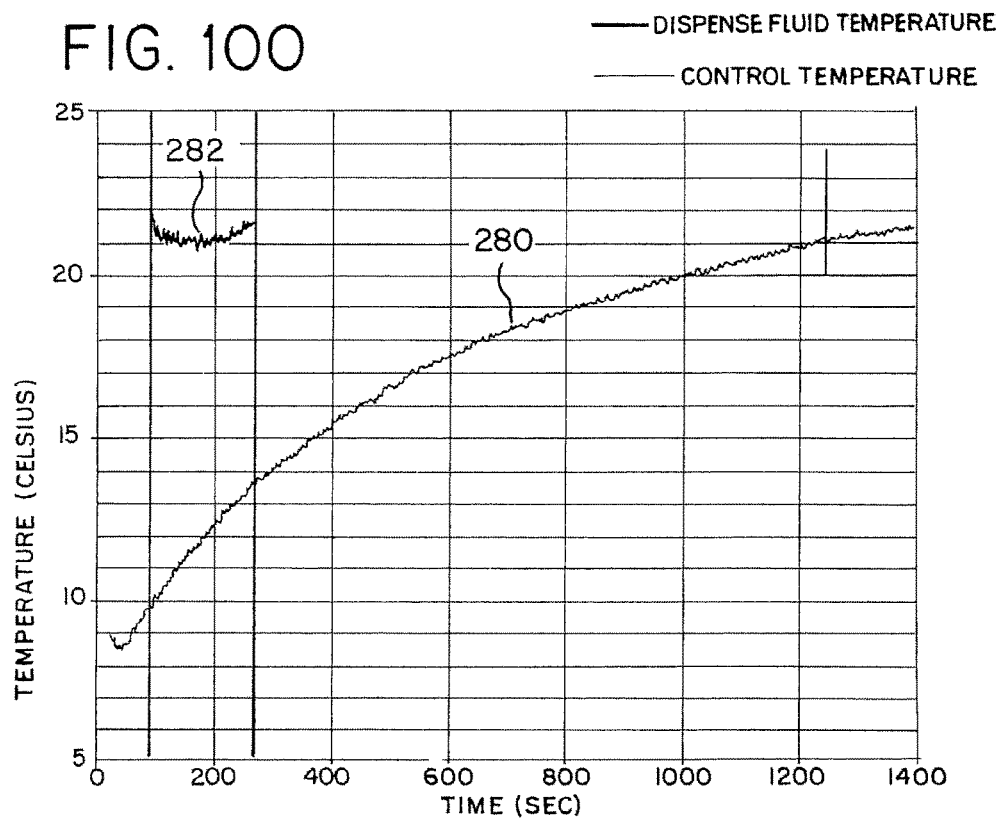
FIG. 100 is a graph illustrating chilled drug warming employing one of the transfer and injection devices disclosed herein.
Figure 101:
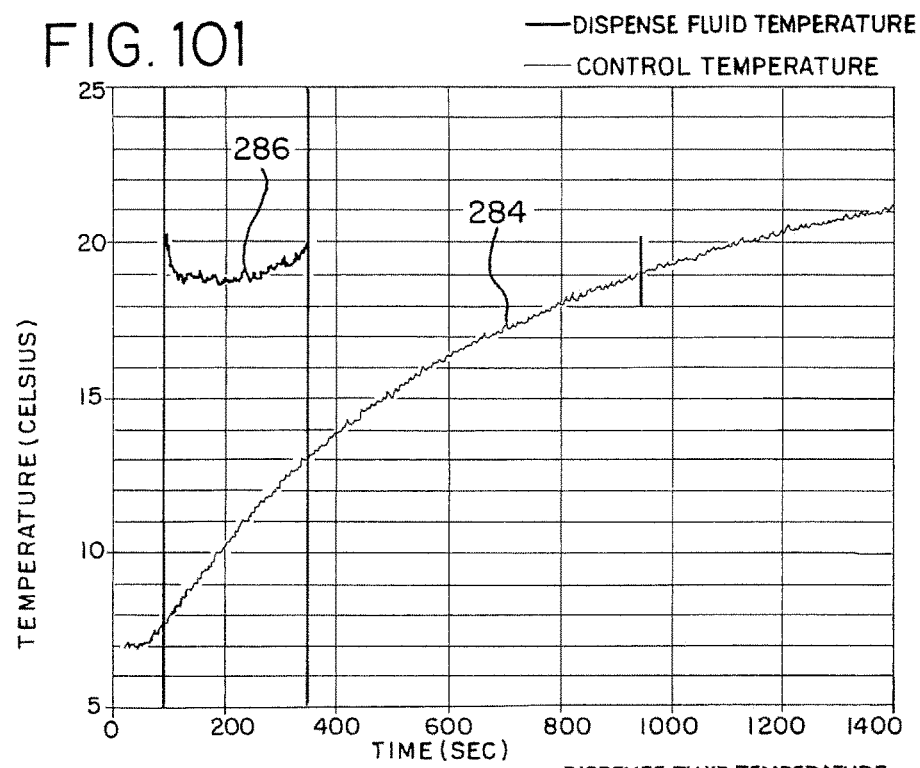
FIG. 101 is another graph illustrating chilled drug warming employing another of the transfer and injection devices of the present application.
Figure 102:
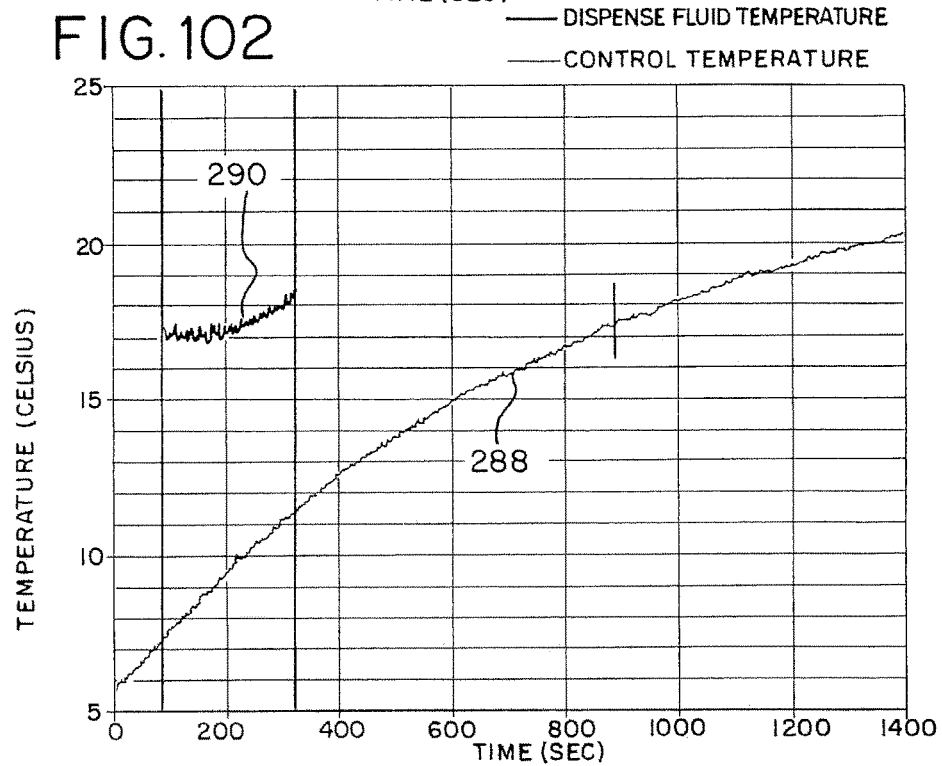
FIG. 102 is yet another graph illustrating chilled drug warming employing another of the transfer and injection devices of the present application.

FIGS. 100-102 are graphs depicting data from certain testing regarding the warming of chilled fluid as it flows through a transfer system and into an injection device similar to that shown in one of the above described transfer and injection devices. FIG. 100 shows the warming of chilled aqueous-based fluid, such as distilled water, as compared to unaided room temperature warming temperature of a like fluid. The test was conducted with a transfer device similar to the transfer device 203 shown in FIGS. 91-93, and injection device 206 similar to that shown in FIGS. 68-76. The transfer device 203 provides for heat transfer from the environment 201 to the cold or chilled fluid 202 contained within the vial 205 as it transferred from the vial 205 to the injection device 206 through fluid pathways 204, resulting in warming of the cold solution 202 to near room temperature in significantly less time than unaided warming of the vial and reducing the time that a patient has to wait to give themselves an injection.

Drugs that require cold storage must normally be allowed to warm to room temperature before administration. The transfer and injection devices described herein provide for relatively prompt warming of the fluid after removal from a refrigerator and without the wait required for unaided warming of a drug vial at room temperature. More specifically, FIG. 100 shows two datasets or graphs, 280 and 282, with temperature (° C.) on the Y axis and time (seconds) on the X-axis. The first dataset or graph 280 represents the unaided warming of the aqueous-based fluid contents of a standard glass vial 205 with the fluid contents 202 starting at or near a range of 2-8° C. The vial contained a simulated single injectable dose of 4 cc of fluid having a room temperature viscosity of about 8 cP. The vial 205 was removed from the refrigerator and a temperature monitoring system was inserted into the vial to monitor the temperature of the solution. Therefore, the vial was used as a control comparison to generally model or represent a standard chilled drug vial or a prefilled injection system (e.g., a prefilled syringe) which the user is instructed to remove from the refrigerator and let set (such as on a counter top) to gradually warm to room temperature before use. FIG. 100, graph 280, shows such a normal first-order warming of the solution as a function of time. As can be seen from the graph 280, from the time of removal from the refrigerator, approximately 20 minutes (1200 seconds) was required for the temperature of the fluid in the vial to rise to 21° C., with an average ambient room temperature of about 23.8° C.

The second dataset or graph 282 in FIG. 100 is derived from a second vial 205 of cold aqueous-based fluid 202 of the same volume transferred and dispensed from the transfer device similar to 203 (but without the heat exchanger 207) and injection device 206. Briefly, this attempted to generally model the expected procedure followed by a patient, including transfer of the injectable from a vial, through the transfer apparatus and into the injection device, and dispensing from the injection device. The transfer device employed a PVC fluid flow tubing 204 having an ID of about 0.05 inches (1.3 mm), a flow path length from the vial to the rigid plastic pressure chamber C of about 4.86 inches (12.3 cm), a flow path length from the pressure chamber C to a filter (not shown) of about 1.0 inches (2.54 cm) and from the filter into the expandable chamber or bladder in the injection device 206 of about 0.5 inches (1.27 cm). As explained earlier, the pressure chamber C is for effecting movement of the fluid from the vial, through the transfer apparatus and into the expandable member or bladder 78 of the injection device 206. Dispensing from the injection device is through a 30 gauge needle.

Referring to FIG. 100, the second vial 205 with cold fluid 202 at 2-8° C. is removed from the refrigerator at time=0. The vial 205 is inserted into the transfer device 203 to start the automatic transfer. The cold fluid 202 is transferred from the vial 205 through the fluid pathways 204, the pressure chamber C and into the injection device 206. Once the transfer is complete, the solution is dispensed from the injection device 206. A temperature monitoring system measures the output stream temperature of the fluid being dispensed from the injection device 206. In FIG. 100, this dispense starts at about t=80 seconds and is completed at about t=270 seconds. The fluid temperature is measured through the entire dispense process as shown in FIG. 100.

As can be seen in FIG. 100, as a result of transfer through the transfer device 203 and into the injection device 206, both of which start at ambient room temperatures of about 23.8° C., the temperature of the dispensing fluid has already reached about 21° C. within about 80 seconds from removal from the refrigerator. Continued measurement shows that the dispensed solution is between 21 and 22° C. for the entire period of dispense from beginning to end. As compared to the simulated standard chilled vial or chilled prefilled system, the time saved for the patient with the present system is about 18 minutes. The rate of temperature increase in the transfer apparatus and injection device are, on average, greater than about 10 times the rate of temperature increase using unaided ambient heating. This should contribute significantly to patient compliance, as the steps with the present system are relatively continuous and without long delays. In contrast, allowing a vial to sit on a counter for 20 minutes until it warms (as in the unaided ambient warming procedure) invites patient forgetfulness or distraction, which can easily result in a missed or untimely treatment or injection.

Testing was also done to simulate the system of FIGS. 88-90, and is reflected in FIG. 101. As shown there, the manual syringe system 189 also provides for heat transfer to the injectable 196 in the syringe 197 and as it transferred from the syringe and into the injection device 7 through fluid pathways 195, allowing chilled drug or other solution to reach near-room temperature prior to dispensing from the injection device. FIG. 101 shows two datasets or graphs 284 and 286 with temperature (° C.) on the Y axis and time (seconds) on the X-axis. The first graph 284 is from a standard glass vial 205 with cold aqueous-based fluid 202 of the same volume and viscosity (4 cc, 8 cP) as employed in the data reported in FIG. 100, at or near a range of 2-8° C. when removed from a refrigerator. The vial 205 is removed and a temperature monitoring system is inserted into the vial to monitor the temperature of the solution. This is the control and simulates a prefilled system injection system in which the user is instructed to remove from the refrigerator and let set out to warm to room temperature before use. FIG. 101 graph 294 shows a normal first-order warming of the solution as a function of time, and shows that warming by exposure to a room temperature of about 24.2° C. (such as by simply sitting on a counter top in the room) required about 23 minutes.

The second dataset or graph 286 in FIG. 101 is based on the removal of injectable 196 from a second vial 204 of cold fluid 202 of like volume and viscosity transferred and dispensed from the manual syringe system 189 and injection device 7, both of which start at ambient room temperature of about 24.2° C. Referring to FIG. 101, a room temperature standard syringe 197 of rigid plastic material is used to withdraw cold injectable fluid 196 from a second vial 205 at 2-8° C., removed from the refrigerator at about time t=0. The syringe with injectable fluid 196 is inserted into the manual syringe system 189 to start the manual transfer. In FIG. 89, the cold injectable 196 is transferred from the syringe 197 through the fluid pathways 195 into the injection device 7. The solution or fluid is transferred through standard PVC tubing having an ID of about 0.050 inches (1.3 mm) and a flow path length of about 3 inches (7.6 cm), from the syringe to the injection device and into the expandable member or bladder 78 of the injection device. In actual applications, the flow path could also include check valves, filters, and the like.

After the transfer is complete, the solution is dispensed from the injection device 7. A temperature monitoring system measures the output stream temperature of the fluid being dispensed from the injection device 7. As seen in FIG. 101, this dispensing starts at about 80 seconds after removal of the vial from the refrigerator. The dispensed fluid temperature is measured through the entire dispense process as shown in FIG. 101, which dispense is completed at about 350 seconds (5.8 minutes).

As can be seen in FIG. 101, the fluid or solution is near room temperature even at the beginning of dispense from the injection device and is between about 19° C. and 20° C. during the entire injection. The equivalent start of dispense at the same temperature (19-20° C.) with the unaided warming of a simulated prefilled system compared to the present embodiment results in a time savings using the current system of approximately 13 minutes.

Referring to FIGS. 88-90, a repeated test was performed on an injectable fluid 196 in a syringe (not a vial) stored in a refrigerator. FIG. 102 shows two datasets or graphs 288 and 290 with temperature (° C.) on the Y axis and time (seconds) on the X-axis. The first dataset or graph 288 is from a standard rigid plastic syringe 197 with aqueous-based injectable fluid 196 (4 cc volume, 8 cP viscosity), such as distilled water, stored in a refrigerator at or near a range of 2-8° C. The syringe 197 with injectable fluid 196 is removed and a temperature monitoring system is inserted into the syringe to monitor the temperature of the solution. This is the control and simulates a prefilled system injection system in which the user is instructed to remove from the refrigerator and let it set out, such as on a counter top, to warm to room temperature before use. In FIG. 102, the first dataset or graph 298, shows a normal first-order warming of the solution as a function of time.

The second dataset or graph 290 is derived the removal of a second standard rigid plastic syringe 197 with aqueous-based injectable fluid or solution 196 of like volume transferred and dispensed using the manual syringe system 189 and injection device 7, both starting at ambient room temperature of about 24.2° C. Referring to FIG. 102, the second syringe 197 with injectable 196 is removed from the refrigerator at t=0. The syringe with injectable 196 is inserted into the manual syringe system 189 to start the manual transfer. As shown in FIG. 89, the cold injectable 196 is transferred from the syringe 197 through the fluid pathways 195 into the injection device 7. The general dimensions are as described earlier for the use of this system. After the transfer is complete, the solution is dispensed from the injection device 7. A temperature monitoring system measures the output stream temperature of the fluid being dispensed from the injection device 7. In FIG. 102, this dispense starts at about t=80 seconds. The fluid temperature is measured through the entire dispense process as shown in FIG. 102, and is between about 17° C. and 18° C. during the entire dispense, which is completed at about 5 minutes after removal of the chilled syringe from a refrigerator. The equivalent start of dispense at about the same temperature (17-18° C.) with the unaided warming of a simulated prefilled system compared to the current embodiment results in a time saving of about 13 minutes for the current system.

Radiofrequency Compliance Monitoring

According to the National Council on Patient Information and Education (NCPIE), "Lack of medication adherence is America's other drug problem". Lack of medication adherence (filling/refilling prescriptions on time) and compliance (taking prescriptions on time or as prescribed) by the patient complicates what otherwise can be a normal progression back to good health. Further, lack of medication adherence and compliance adds significant cost to an already burdened health care system with additional medical costs and doctor's visits as well as extended hospital stays. Thus, the success of a medication in the treatment of a condition relies on whether the prescription was filled and regularly taken as instructed. Currently, this is the responsibility of the patient alone. However, even well intentioned patients may accidently forget to take the medication or intentionally stop when the symptoms of their condition start to improve. Thus, a mechanism to alert the patient, the prescriber, the healthcare provider or another third party participant when non-compliance or non-adherence is occurring would be very beneficial to permit intervention or reminder for the reasons outlined above.

In accordance with further aspects of the present subject matter, when administering an injection with an automatic injection device, it is desirable to know when the prescription for the injection device was initially filled or refilled as well as whether the injection device was used properly and on time. While many prescription drugs are tracked at the time they are filled by the patient using specialized labeling, there are limited options to confirm if the patient actually took the medication. As more drugs are being presented in injection devices, the ability to automatically track prescription initiation currently has limited usage. Further, the ability to automatically track whether the injection device was used properly does not exist.

As described herein, automatic tracking both for adherence and compliance is accomplished wirelessly using RF (radio frequency) techniques installed within or in cooperative association the transfer and/or injection devices described herein. Current technology allows for the use of radio-frequency identification (RFID) to transfer data, for the purposes of automatically identifying and tracking tags or microcircuit chips attached to objects. As used herein, RF or RFID or RF tags or RF chips are used comprehensively and interchangeably and are intended to include wireless electronic tags or chips for transmitting data/information using any suitable wireless communication protocol or technology, such as Bluetooth or any other wireless technology.

RF tags or chips may be active or passive. While both types use RF energy communicate between a tag or transponder and a reader, the method of powering the tags is different. Active RFID uses an internal power source (such as a battery) within or associated with the tag to continuously power the tag and its RF communication circuitry, whereas passive RFID relies on RF energy transferred from the reader to the tag to power the tag. In the present subject matter, the injection device or the transfer package may include an RFID tag, may optionally include a power source for the tag and be read or received by an external reader. In one embodiment, the RF tag or chip is removably associated with the injection device such that it can be physically removed from the injection device when the injection device is used. This allows for the subsequent disposal of the injection device free of the limitations or restrictions that might apply if the tag or chip remained as part of the injection device after its use.

Figure 94:
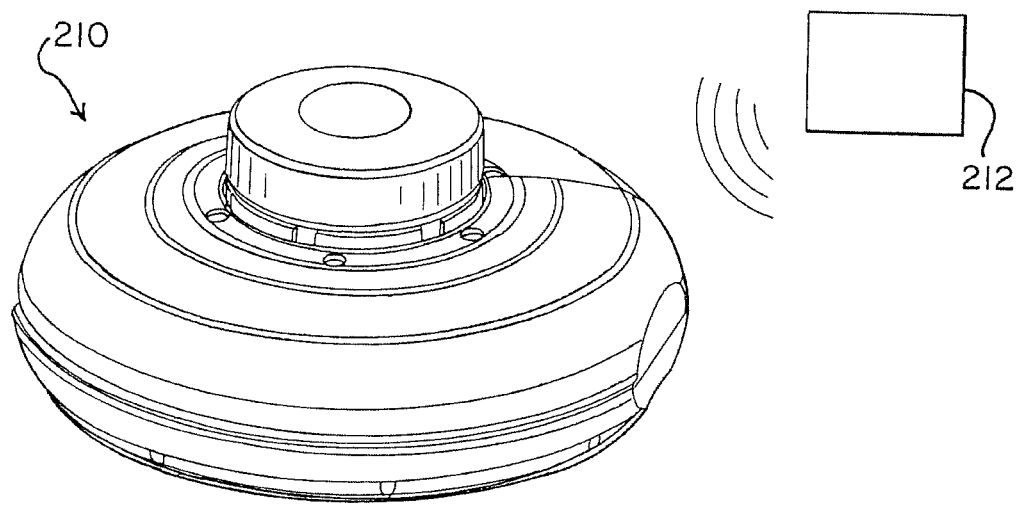
FIG. 94 is a perspective view of an injection device including an Rf tag and a tag reader or interrogator.
Figure 95:
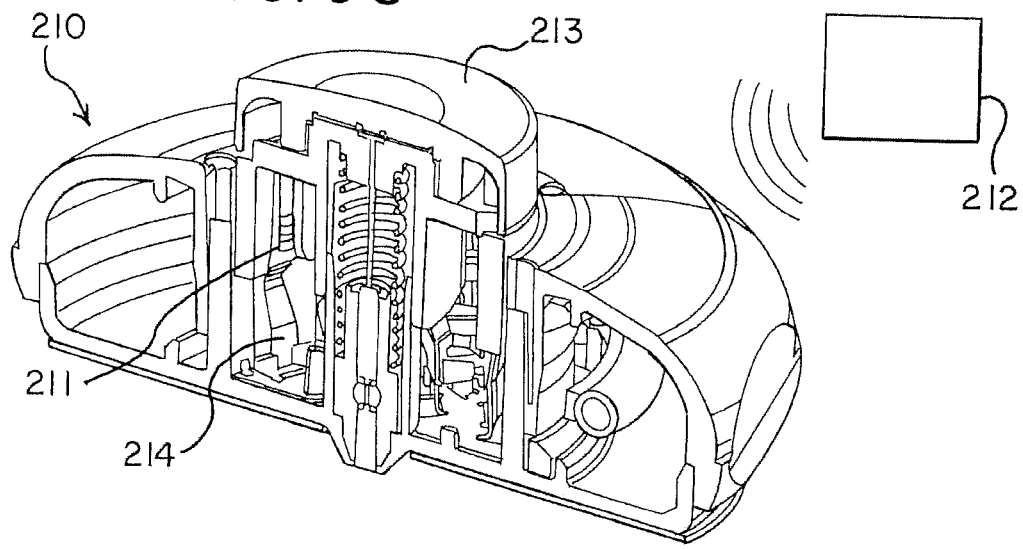
FIG. 95 is similar to FIG. 94, but shows the injection device in cross section.

Referring to FIGS. 94-95, the injection device 210 may include an RF tag or chip 211 to monitor the injection device 210 status. For example, the RF tag 211 may broadcast to an external reader 212 (if active) or present (if passive, read by an external reader 212) information or status—such as "the injection device 210 has been prescribed," "the injection device 210 has been removed from its packaging," and "the injection device 210 has been actuated" and/or "the injection device 210 has completed its dose." The RF tag reader could also be associated with or in communication with an on-site or off-site data collection facility, such as by wireless or hardwired connection to allow recordation and compilation of information regarding compliance.

Referring to FIGS. 94-95, an RF tag 211 may be used to monitor whether the injection device 210 has been activated or has initiated or completed its dose. The injection device 210 may include an active or passive RF tag or chip 211 at any suitable location. As shown below, when used internally of the injection device, the RF tag or chip 211 may be attached to the button 213 and in slideable communication with the spring tabs 214 during the first and second positions of the button 213. While the RF tag 211 is in slideable communication with the spring tabs 214, the RF tag 211 may broadcast (if active) or present (if passive, read by an external reader 212) a first state to include an unused status. In the event the injection device 210 is activated, the button 213 is depressed to the dispense position. At the end of the dispense period, the button 213 is unlocked from the second depth or dispense position (shown in FIG. 95) to move up to a final position or post fire position. At this post-fire position, the RF tag 211 may no longer be in contact with the spring tabs 214, thus allowing for a change in state (second state) of the RF tag 211. In this second state, the RF tag 211 may broadcast (if active) or present (if passive, read by an external reader 212) a second state to include a used status. Alternatively the RF tag 211 may be deformed or altered in such a way upon use of the injection device that, upon interrogation, the RF tag 211 presents a 'used' signature. For instance, if the RF tag consists of two coils joined by a conductor, the initial signature of the tag 211 would be the 'dual coil' signature. Once the tag 211 has been used, if the conductor joining the two coils is broken, then the two independent coils produce a different signature.

Location of the RF tab or chip outside of the injection device may be desired for regulatory and/or disposability reasons. For example, the RF tag or chip 211 also may be associated with the transfer device or with another part of the system, such as for example, safety sleeve or pull tab 100 (see FIG. 83), to activate the tag or chip at a selected point or points in the operation of the transfer device and/or injection device. An active RF tag or chip could, for example, be located on the safety sleeve and configured so that removal of the safety sleeve to start the injection process closes a contact between a long shelf-life battery and the tag or chip transmitter.

In other words, the RF chip or tag may have two states, a standby or off state and an active, or transmitting, state. The state may be changed by making or breaking a contact. Making contact could be achieved, for example, by configuring the contacts on safety release or pull tab 100 so that they remain in a spaced apart relation when the pull tab is in position on the injection device, and so that they come together to contact one another when the pull tab is removed from the injection device to start the injection. Further, different actions associated with the use of the transfer and/or injection device could be employed to make or break contact. For example, a previously inactive RF tag or chip could be activated by closing a contact between a battery and the chip or tag transmitter when one action is taken, such as when a vial is inserted into the transfer device, and deactivated by another action, such as by breaking such contact after use of injection device.

Figure 96:
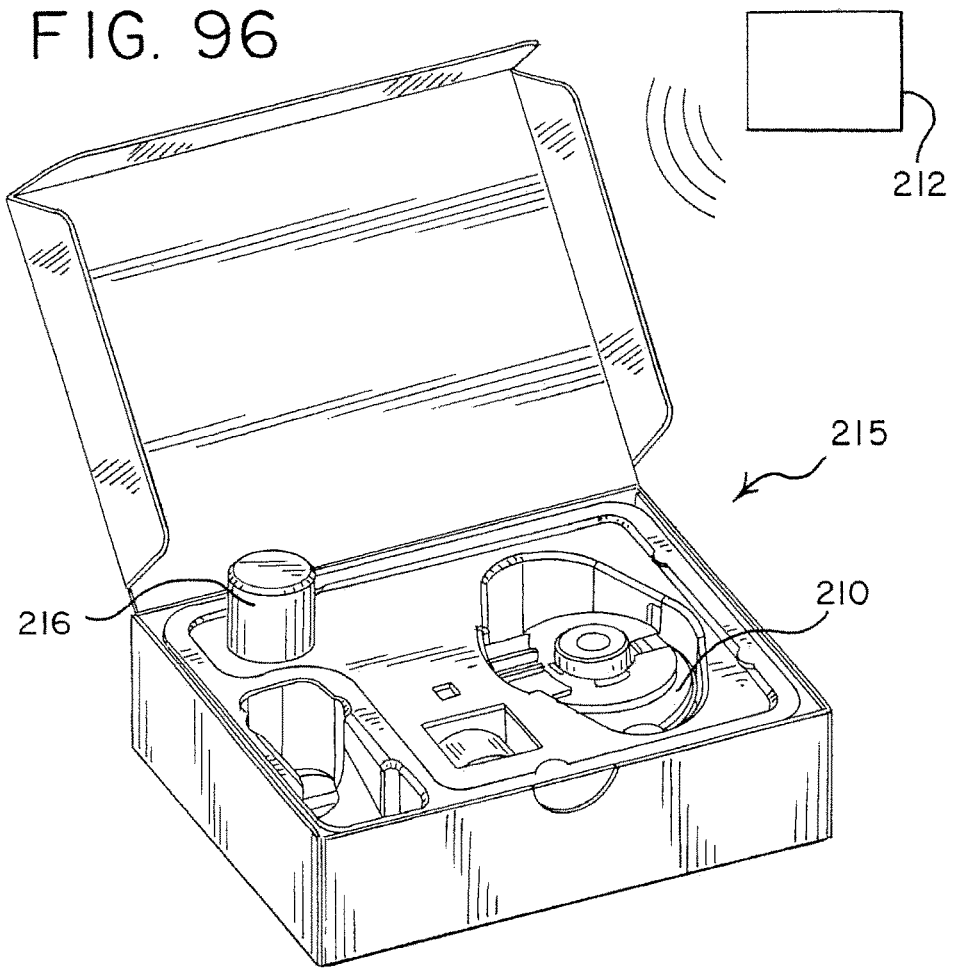
FIG. 96 is a perspective view of a transfer apparatus for transferring an injectable from a prefilled source, such as a vial, to an associated injection device in combination with an Rf reader.
Figure 97:
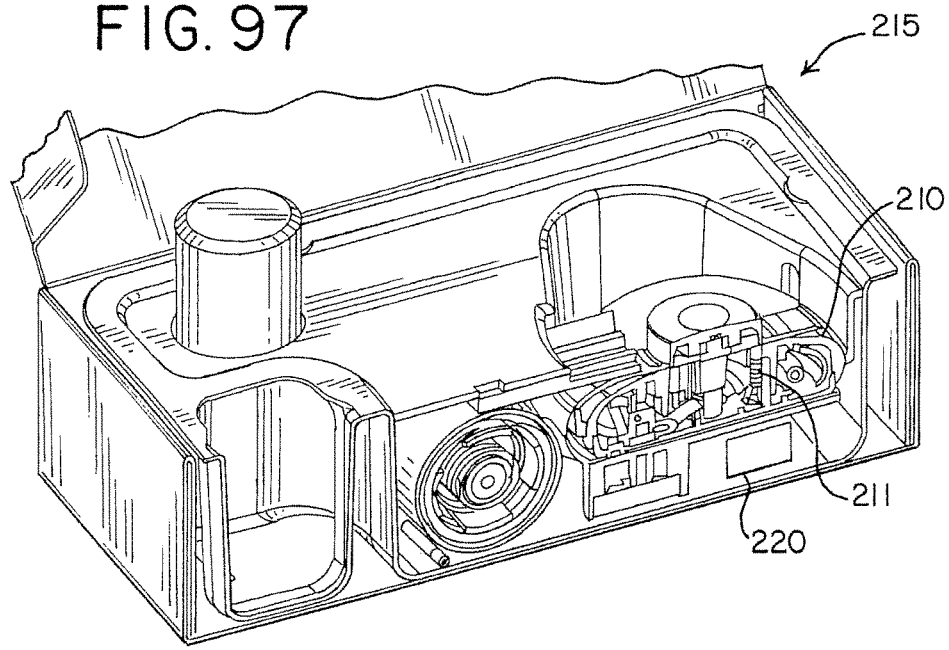
FIG. 97 is a cross-sectional view of the transfer apparatus and injection device of FIG. 96.
Figure 98:
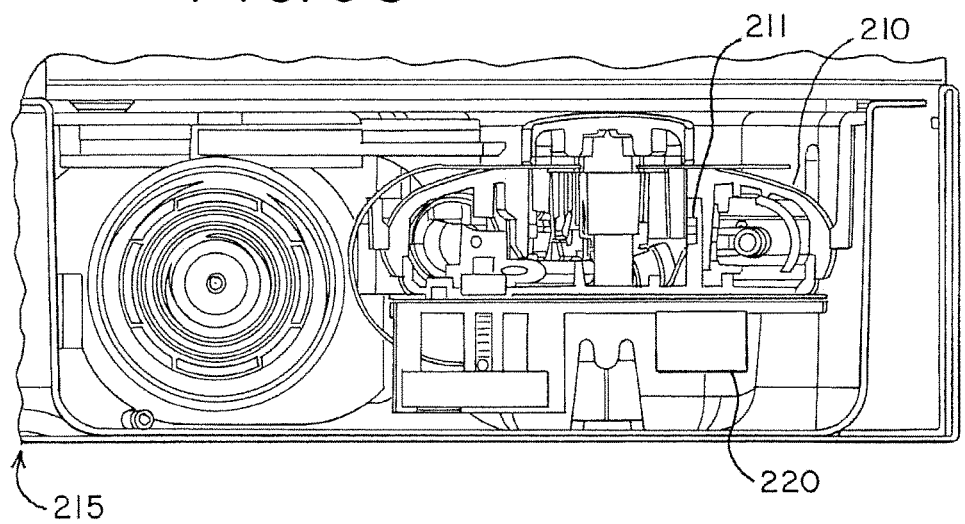
FIG. 98 is an enlarged view of a portion of the cross-section of FIG. 97 viewed from a different angle.

Referring to FIGS. 96-98, for further example, the transfer device 215 may include an RF tag 211 to track the usage of the transfer package 215. For example, the RF tag 211 may broadcast to an external reader 212 (if active) or present (if passive, read by an external reader 212) information such as—the transfer package 215 has been opened, the vial 216 has been inserted, the transfer package 215 has been actuated, and/or the injector 210 has been removed from the transfer package 215. Referring to FIGS. 97-98, in another embodiment, the transfer device 215 may include provisions for reading an RF tag 211 within the injection device 206. For instance, in the existing transfer packages 215, the active RF transmission could occur once the vial/syringe/cartridge 216 is inserted into the transfer device 215, or once the locking blade 217 is retracted, or once the injector 210 is removed. An advantage of mounting the active transmitter 220 in the transfer device 215 is there is more room for mounting and/or power supply, and the transmitter 220 does not need to reside on the injector 210.

Figure 99:
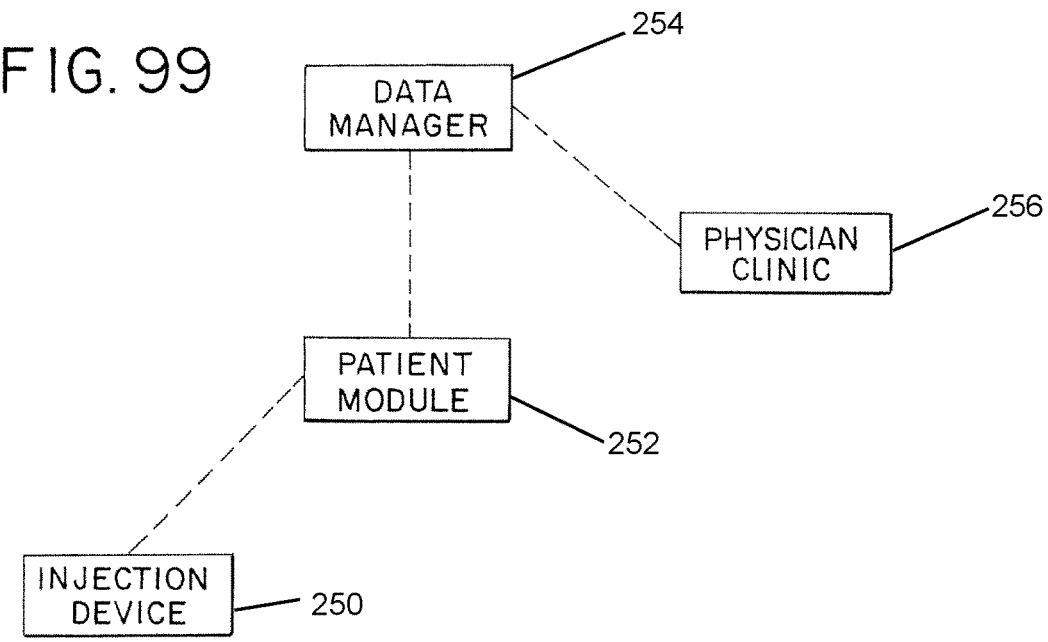
FIG. 99 is a block diagram/flow chart, illustrating a system employing the present subject matter for monitoring patient compliance.

The RF tag or chip 211 may transmit or communicate data associated with the transfer or injection device—in addition to use information. For example, the tag or chip may be configured, with memory storage capacity, to transmit the type of injection device, lot number, fluid quantity administered, drug identification and other relevant information. FIG. 99 diagrammatically illustrates one system that may be employed with the present subject matter. As shown there, the RF tag or chip 250 may be of the active type, and when activated actively transmits the pertinent information to a local Patient Module 252 located within the vicinity of the patient and injection device. For example, the Patient Module could be a wall-mounted or desktop device located in the patient's home for receiving the monitoring information transmitted by the RF tag or chip associated with the injection device and/or transfer device. The Patient Module could also be a cellular telephone or the like.

The Patient Module could include a memory that maintains data such as patient identification and related information. The Patient Module, in turn, communicates in an appropriate manner, such WIFI, cellular communication, telephone, hard wire link or other, with a Data Manager 254, which could be any appropriate data network or Cloud storage arrangement for receiving and/or storing data received from the Patient Module indicating injection device status and/or usage in association with the particular identifying patient information. The Data Manager would be accessible by medical personnel responsible for the monitoring of the patient's use of the injection device and patient compliance with any prescribed injection regimen. The Data Manager could also be configured to automatically relay patient compliance information to the appropriate medical personnel, such as a particular physician or clinic 256.

Other aspects of a compliance monitoring apparatus, system and method and use with an injection device such as described herein are shown in FIGS. 105-109. As illustrated there, the system may include a wireless, e.g., Bluetooth, source, such as a battery powered sending unit such as a microchip, indicated at 262 in FIGS. 107 and 108. The sending unit may be mounted in any suitable location, and can be associated with or attached to a part of the injection device (an/or transfer device) in a manner so that it can be detached from the injection device or transfer device at the time of disposal—allowing most of the injection device or transfer device structure to be recycled, as electronic circuitry and electronic chips are typically not similarly recyclable.

Figure 108:
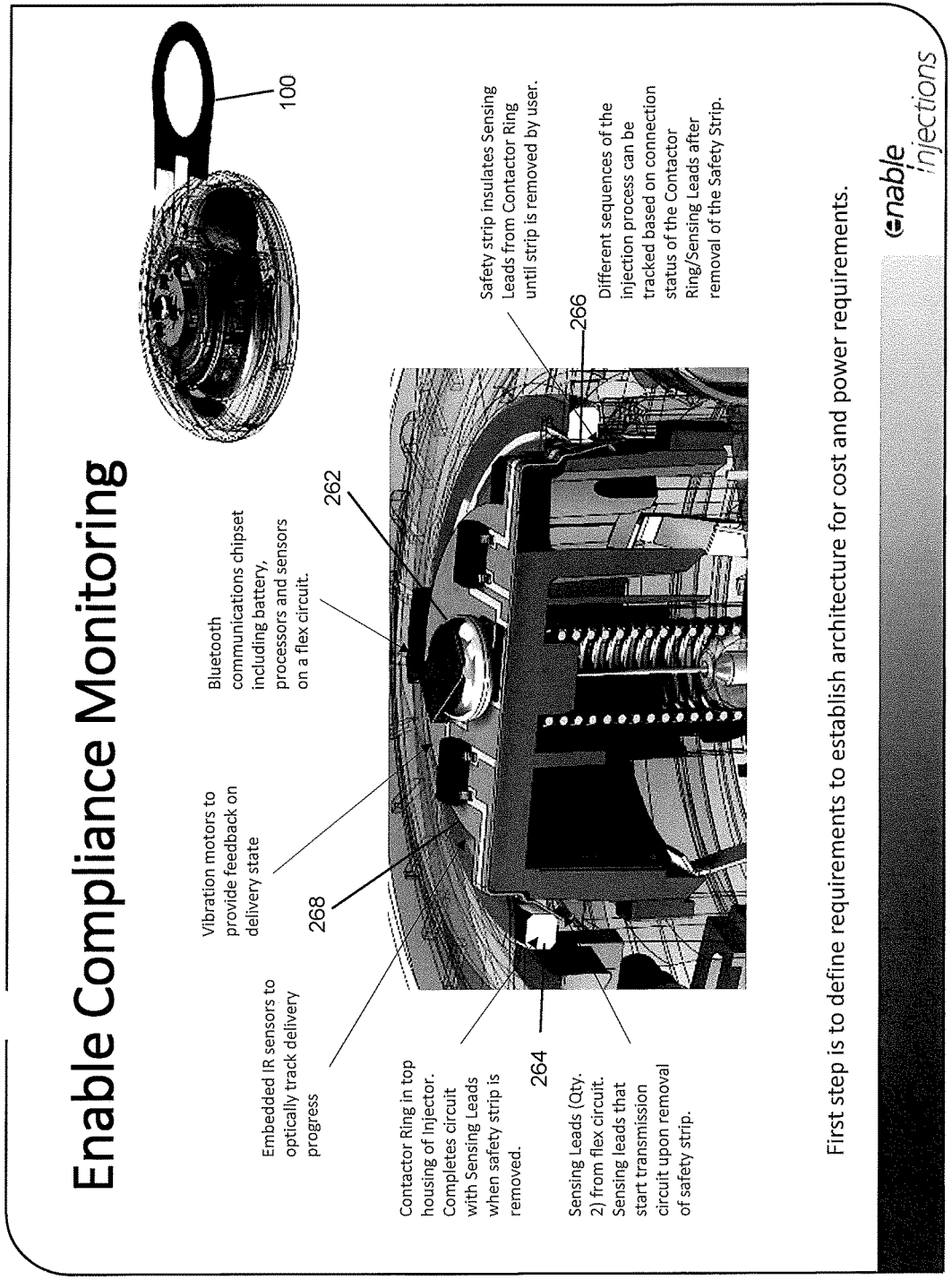
FIG. 108 shows yet further aspects of a compliance monitoring system in connection with a cross-sectional view of an injection device as described herein.
Figure 109:
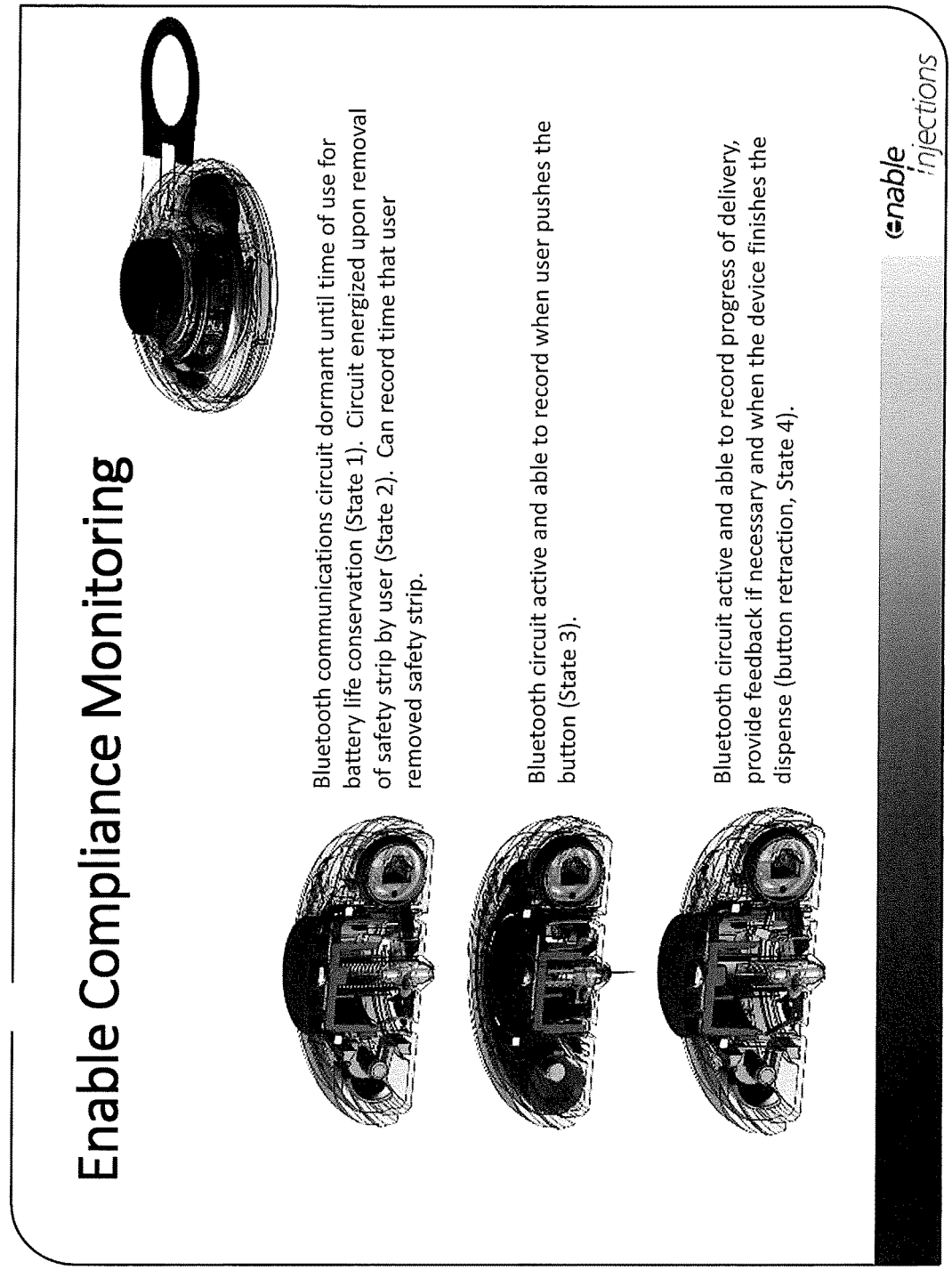
FIG. 109 Illustrates compliance monitoring with an injection device as described herein with cross-sectional views illustrating the compliance status in different stages of injection device usage.

In addition, with reference to FIG. 108, a contactor ring 264 is provided in the top of the of the injection device housing and is prevented from making contact with sensing leads 266 (which are attached to the injection device button) when the safety strip 100 is installed (as illustrated in FIG. 83). When the safety strip 100 is removed, the contactor ring 264 of the housing makes contact with the sensing leads 266 of the button. Different sequences of the injection process may then be tracked based on the connection status between the contactor ring and the sensing leads (i.e. position of the contactor ring 264 with respect to the sensing leads 266). Infrared sensors 268 may also be embedded in the injection device to optically track delivery progress, such as by, for example, monitoring of the position of, or amount of injectable fluid in, expandable member of the injection device.

The present subject matter has been described in terms of specific embodiments for purposes of illustration only, and not limitation. It is to be understood that the scope of the subject matter is not limited to only the illustrated embodiments or equivalents thereof but has broader application in embodiments of varying configuration and use some of which may be readily apparent upon reading this description and others only after some study and/or development.

What is claimed is:

1. A medication injection device comprising:
   a housing having a skin-facing surface configured to contact a user's skin;
   a skin displacement structure extending from and surrounded by the skin-facing surface, said skin displacement structure including an injection needle aperture positioned therein and defining an injection needle aperture opening;
   an injection needle that slidably extends out of the injection needle aperture opening and beyond the skin displacement structure, wherein the injection needle is movable from an initial retracted position to an injection position extending to a selected subcutaneous depth for injection and back to a final retracted position after an injection is complete;
   said injection needle aperture containing a septum that is positioned within the skin displacement structure, where the septum contacts and guides the injection needle as it slidably extends;
   the skin displacement structure serving to compress tissue around the injection needle aperture opening and thereby creating a tissue pressure zone around the injection needle aperture opening having higher pressure than in tissue outwardly of the tissue pressure zone, the medication injection device being configured to maintain the tissue pressure zone after the needle returns to the final retracted position.

2. The medication injection device of claim 1 wherein the injection needle is extendable through the injection needle aperture sufficiently to extend not more than about 5 mm into tissue when the skin-facing surface is placed in contact with the user's skin.

3. The medication injection device of claim 2 in which the injection needle extends to a subcutaneous depth of about 5 mm and generates a medication bolus depth of about 0.4 cm-about 0.45 cm.

4. The medication injection device of claim 1 wherein the injection needle is extendable through the injection needle aperture sufficiently to extend a selected subcutaneous distance into tissue, the selected subcutaneous distance providing substantially similar medication bolus depth as an injection needle extending substantially twice the selected depth in an absence of skin displacement.

5. The medication injection device of claim 1 wherein the skin displacement structure is configured to form an extension contact area within a user's skin, said extension contact area having a generally concave profile containing a point of needle insertion.

6. The medication injection device of claim 5 wherein the extension contact area extends radially outwards from the point of needle insertion.

7. The medication injection device of claim 6 wherein the point of needle insertion is centrally located within the concave profile of the extension contact area.

8. The mediation injection device of claim 1 wherein the skin displacement structure includes a tip having a generally planar skin contact surface including the injection needle aperture opening.

9. The medication injection device of claim 1 wherein the skin displacement structure compresses tissue surrounding and extending radially outwards from the injection needle aperture opening when the skin-facing surface is in contact with the user's skin.

10. The medication injection device of claim 1 wherein the skin-facing surface includes adhesive that is configured to secure the medication injection device to the user's skin.

* * * * *